US012703742B2

(12) United States Patent
Han et al.

(10) Patent No.: US 12,703,742 B2
(45) Date of Patent: Aug. 11, 2026

(54) BIFUNCTIONAL ANTAGONISTS OF ACTIVIN AND TUMOR NECROSIS FACTOR ALPHA AND USES THEREOF

(71) Applicants: Hq Han, Westlake Village, CA (US); Xiaolan Zhou, Newbury Park, CA (US)

(72) Inventors: Hq Han, Westlake Village, CA (US); Xiaolan Zhou, Newbury Park, CA (US)

( * ) Notice: Subject to any disclaimer, the term of this patent is extended or adjusted under 35 U.S.C. 154(b) by 625 days.

(21) Appl. No.: 18/033,333

(22) PCT Filed: Oct. 22, 2021

(86) PCT No.: PCT/US2021/056272

§ 371 (c)(1),
(2) Date: Apr. 22, 2023

(87) PCT Pub. No.: WO2022/087426

PCT Pub. Date: Apr. 28, 2022

(65) Prior Publication Data

US 2023/0391863 A1 Dec. 7, 2023

Related U.S. Application Data

(60) Provisional application No. 63/113,918, filed on Nov. 15, 2020, provisional application No. 63/104,765, filed on Oct. 23, 2020.

(51) Int. Cl.

| | |
|---|---|
| ***A61K 39/395*** | (2006.01) |
| ***A61K 38/17*** | (2006.01) |
| ***A61P 9/12*** | (2006.01) |
| ***A61P 11/00*** | (2006.01) |
| ***A61P 19/08*** | (2006.01) |
| ***C07K 14/71*** | (2006.01) |
| ***C07K 16/22*** | (2006.01) |
| ***C07K 16/24*** | (2006.01) |
| *A61K 39/00* | (2006.01) |

(52) U.S. Cl.

CPC .......... *C07K 16/241* (2013.01); *A61K 38/179* (2013.01); *A61K 39/3955* (2013.01); *A61P 9/12* (2018.01); *A61P 11/00* (2018.01); *A61P 19/08* (2018.01); *C07K 14/71* (2013.01); *C07K 16/22* (2013.01); *A61K 2039/505* (2013.01); *C07K 2317/31* (2013.01); *C07K 2317/76* (2013.01); *C07K 2317/92* (2013.01); *C07K 2319/30* (2013.01); *C07K 2319/32* (2013.01)

(58) Field of Classification Search

CPC .............. A61K 39/3955; A61K 38/179; C07K 16/241; C07K 14/71

See application file for complete search history.

(56) References Cited

U.S. PATENT DOCUMENTS

| | | | |
|---|---|---|---|
| 8,163,896 B1 | 4/2012 | Bentwich | |
| 2008/0292628 A1 | 11/2008 | Hui | |
| 2015/0125450 A1* | 5/2015 | Goldenberg ....... | A61K 47/6889 530/387.3 |
| 2016/0326241 A1* | 11/2016 | Auer .................... | C07K 16/244 |
| 2018/0252728 A1 | 9/2018 | Georgantas, III et al. | |
| 2020/0179531 A1 | 6/2020 | Hawthorne et al. | |

FOREIGN PATENT DOCUMENTS

| | | |
|---|---|---|
| WO | 2018009732 | 1/2018 |
| WO | 2020187711 | 9/2020 |

OTHER PUBLICATIONS

Hamang Matthew J et al: "The Roles of Activin A and Bin Liver Inflammation and Fibrosis", May 1, 2019 (May 1, 2019), Dept of Biology, Master Thesis, Purdue University.

Kiagiadaki Foteini et al: "Activin-A causes Hepatic stellate cell activation via the induction of TNF[alpha] and TGF [beta] in Kupffer cells", Biochimica et Biophysica Acta. Molecular Basis of Disease., vol. 1864, No. 3, Mar. 1, 2018 (Mar. 1, 2018), pp. 891-899.

Sato Atsushi et al., "Involvement of the TNF and FasL Produced by CD11b Kupffer Cells/Macrophages in CC14-Induced Acute Hepatic Injury", PLOS ONE, vol. 9, No. 3, Mar. 25, 2014 (Mar. 25, 2014), p. e92515.

Zhou Xiaolan et al: "Reversal of Cancer Cachexia and Muscle Wasting by ActRIIB Antagonism Leads to Prolonged Survival", Cell, vol. 142, No. 4, Aug. 20, 2010 (Aug. 20, 2010), pp. 531-543.

Kudryashova Tatiana et al.: "Inhibitory Antibodies against Activin A and TGF-[beta] Reduce Self-Supported, but Not Soluble Factors-Induced Growth of Human Pulmonary Arterial Vascular Smooth Muscle Cells in Pulmonary Arterial Hypertension", International Journal of Molecular Sciences, vol. 19, No. 10, Oct. 1, 2018 (Oct. 1, 2018), p. 2957.

Jiang Lingling et al: "Antagonistic effects of activin A and TNF-[alpha] on the activation of L929 fibroblast cells via Smad3-independent signaling", Scientific Reports, Nov. 26, 2020 (Nov. 26, 2020).

Blonska, M. et al., Restoration of NF-kappaB activation by tumor necrosis factor alpha receptor complex-targeted MEKK3 in receptor-interacting protein-deficient cells, Molecular and cellular biology, 2004, 24(24), 10757-10765.

Shen J. et al., Single variable domain-IgG fusion: a novel recombinant approach to Fc domain-containing bispecific antibodies, Journal of Biological Chemistry, 2006, vol. 281, No. 16, p. 10706-10714, p. 10713.

(Continued)

*Primary Examiner* — Xiaozhen Xie

(74) *Attorney, Agent, or Firm* — Craig A Crandall, APC; Craig A Crandall

(57) ABSTRACT

This invention disclosure provides novel bifunctional antagonistic polypeptides comprising at least one TNF-α binding domain and at least one Activin-binding domain, which are highly capable of sequestering TNF-α and Activin or Activin-related ligand in parallel. Also provided are pharmaceutical compositions of such bifunctional polypeptide antagonists and their uses to treat various complex disease conditions, whose pathogenesis involve the activation of both TNF-α-mediated NF-κB signaling pathway and Activin-mediated Smad2/3 signaling pathway.

7 Claims, 12 Drawing Sheets

Specification includes a Sequence Listing.

(56) References Cited

OTHER PUBLICATIONS

Torres M. et al., The immunoglobulin constant region contributes to affinity and specificity, Trends in immunology, 2008, vol. 29, No. 2, p. 91-97, pp. 93-94.
Badri H. et al., Optimization of radiation dosing schedules for proneural glioblastoma, J Math Bio, 2016, vol. 72, N. 5, pp. 1301-1336.
Baylot V. et al., TCTP Has a Crucial Role in the Different Stages of Prostate Cancer Malignant Progression, Results Probl Cell Differ, 2017, vol. 64, pp. 255-261.
Muller S. et al., Spliceosomal peptide P140 for immunotherapy of systemic lupus erythematosus: results of an early phase II clinical trial, Arthritis & Rheumatism: Official Journal of the American College of Rheumatology, 2008, vol. 58, No. 12, p. 3873-3883, p. 3874.

* cited by examiner

TNF-Binding Polypeptide
(Fusion Partner A)

Linker

Activin-Binding Polypeptide
(Fusion Partner B)

SEQUENCE LISTING

```
<160> NUMBER OF SEQ ID NOS: 93

<210> SEQ ID NO 1
<211> LENGTH: 190
<212> TYPE: PRT
<213> ORGANISM: Homo sapiens

<400> SEQUENCE: 1

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr
            180                 185                 190


<210> SEQ ID NO 2
<211> LENGTH: 235
<212> TYPE: PRT
<213> ORGANISM: Homo sapiens

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
```

```
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235


<210> SEQ ID NO 3
<211> LENGTH: 242
<212> TYPE: PRT
<213> ORGANISM: Homo sapiens

<400> SEQUENCE: 3

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Ser Cys Glu
    50                  55                  60

Asp Ser Thr Tyr Thr Gln Leu Trp Asn Trp Val Pro Glu Cys Leu Ser
65                  70                  75                  80

Cys Gly Ser Arg Cys Ser Ser Asp Gln Val Glu Thr Gln Ala Cys Thr
                85                  90                  95

Arg Glu Gln Asn Arg Ile Cys Thr Cys Arg Pro Gly Trp Tyr Cys Ala
            100                 105                 110

Leu Ser Lys Gln Glu Gly Cys Arg Leu Cys Ala Pro Leu Arg Lys Cys
        115                 120                 125

Arg Pro Gly Phe Gly Val Ala Arg Pro Gly Thr Glu Thr Ser Asp Val
    130                 135                 140

Val Cys Lys Pro Cys Ala Pro Gly Thr Phe Ser Asn Thr Thr Ser Ser
145                 150                 155                 160
```

```
Thr Asp Ile Cys Arg Pro His Gln Ile Cys Asn Val Val Ala Ile Pro
                165                 170                 175

Gly Asn Ala Ser Met Asp Ala Val Cys Thr Ser Thr Ser Pro Thr Arg
            180                 185                 190

Ser Met Ala Pro Gly Ala Val His Leu Pro Gln Pro Val Ser Thr Arg
        195                 200                 205

Ser Gln His Thr Gln Pro Thr Pro Glu Pro Ser Thr Ala Pro Ser Thr
    210                 215                 220

Ser Phe Leu Leu Pro Met Gly Pro Ser Pro Pro Ala Glu Gly Ser Thr
225                 230                 235                 240

Gly Asp


<210> SEQ ID NO 4
<211> LENGTH: 240
<212> TYPE: PRT
<213> ORGANISM: Homo sapiens

<400> SEQUENCE: 4

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Pro Cys Ala Pro Gly Thr Phe Ser Asn Thr Thr Ser Ser Thr Asp
145                 150                 155                 160

Ile Cys Arg Pro His Gln Ile Cys Asn Val Val Ala Ile Pro Gly Asn
                165                 170                 175

Ala Ser Met Asp Ala Val Cys Thr Ser Thr Ser Pro Thr Arg Ser Met
            180                 185                 190

Ala Pro Gly Ala Val His Leu Pro Gln Pro Val Ser Thr Arg Ser Gln
        195                 200                 205

His Thr Gln Pro Thr Pro Glu Pro Ser Thr Ala Pro Ser Thr Ser Phe
    210                 215                 220

Leu Leu Pro Met Gly Pro Ser Pro Pro Ala Glu Gly Ser Thr Gly Asp
225                 230                 235                 240


<210> SEQ ID NO 5
<211> LENGTH: 145
<212> TYPE: PRT
<213> ORGANISM: Homo sapiens

<400> SEQUENCE: 5

Ile Tyr Pro Ser Gly Val Ile Gly Leu Val Pro His Leu Gly Asp Arg
```

```
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys
145


<210> SEQ ID NO 6
<211> LENGTH: 110
<212> TYPE: PRT
<213> ORGANISM: Homo sapiens

<400> SEQUENCE: 6

Glu Thr Gln Glu Cys Leu Phe Phe Asn Ala Asn Trp Glu Lys Asp Arg
1               5                   10                  15

Thr Asn Gln Thr Gly Val Glu Pro Cys Tyr Gly Asp Lys Asp Lys Arg
            20                  25                  30

Arg His Cys Phe Ala Thr Trp Lys Asn Ile Ser Gly Ser Ile Glu Ile
        35                  40                  45

Val Lys Gln Gly Cys Trp Leu Asp Asp Ile Asn Cys Tyr Asp Arg Thr
    50                  55                  60

Asp Cys Val Glu Lys Lys Asp Ser Pro Glu Val Tyr Phe Cys Cys Cys
65                  70                  75                  80

Glu Gly Asn Met Cys Asn Glu Lys Phe Ser Tyr Phe Pro Glu Met Glu
                85                  90                  95

Val Thr Gln Pro Thr Ser Asn Pro Val Thr Pro Lys Pro Pro
            100                 105                 110


<210> SEQ ID NO 7
<211> LENGTH: 110
<212> TYPE: PRT
<213> ORGANISM: Homo sapiens

<400> SEQUENCE: 7

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
```

```
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110


<210> SEQ ID NO 8
<211> LENGTH: 315
<212> TYPE: PRT
<213> ORGANISM: Homo sapiens

<400> SEQUENCE: 8

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Glu Asp Glu Asp Gln Asp
    290                 295                 300

Tyr Ser Phe Pro Ile Ser Ser Ile Leu Glu Trp
305                 310                 315


<210> SEQ ID NO 9
<211> LENGTH: 315
```

```
<212> TYPE: PRT
<213> ORGANISM: Homo sapiens

<400> SEQUENCE: 9

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Gln Ser Cys Val Val Asp
65                  70                  75                  80

Gln Thr Gly Ser Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Glu Asp Glu Asp Gln Asp
    290                 295                 300

Tyr Ser Phe Pro Ile Ser Ser Ile Leu Glu Trp
305                 310                 315


<210> SEQ ID NO 10
<211> LENGTH: 288
<212> TYPE: PRT
<213> ORGANISM: Homo sapiens

<400> SEQUENCE: 10

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30
```

```
Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285
```

```
<210> SEQ ID NO 11
<211> LENGTH: 110
<212> TYPE: PRT
<213> ORGANISM: Artificial
<220> FEATURE:
<223> OTHER INFORMATION: Modified human ActRIIB ECD

<400> SEQUENCE: 11

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Asp Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Ile Asn Cys Tyr Asp Arg Gln
    50                  55                  60

Glu Cys Val Ala Thr Lys Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110
```

<210> SEQ ID NO 12
<211> LENGTH: 110
<212> TYPE: PRT
<213> ORGANISM: Artificial
<220> FEATURE:
<223> OTHER INFORMATION: Modified human ActRIIB ECD

<400> SEQUENCE: 12

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Tyr Gly Asp Lys Asp Lys Arg
            20                  25                  30

Arg His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Ala Pro Thr
            100                 105                 110
```

<210> SEQ ID NO 13
<211> LENGTH: 107
<212> TYPE: PRT
<213> ORGANISM: Artificial
<220> FEATURE:
<223> OTHER INFORMATION: Modified human ActRIIB ECD

<400> SEQUENCE: 13

```
Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Asp Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr
            100                 105
```

<210> SEQ ID NO 14
<211> LENGTH: 109
<212> TYPE: PRT
<213> ORGANISM: Artificial
<220> FEATURE:
<223> OTHER INFORMATION: Modified human ActRIIA ECD

<400> SEQUENCE: 14

```
Gly Ala Ile Leu Gly Arg Ser Glu Thr Gln Glu Cys Leu Phe Tyr Asn
1               5                   10                  15

Ala Asn Trp Glu Leu Glu Arg Thr Asn Gln Thr Gly Val Glu Pro Cys
            20                  25                  30

Glu Gly Glu Lys Asp Lys Arg Leu His Cys Tyr Ala Thr Trp Arg Asn
```

```
        35                  40                  45

Ile Ser Gly Ser Ile Glu Ile Val Lys Lys Gly Cys Trp Leu Asp Asp
    50                  55                  60

Phe Asn Cys Tyr Asp Arg Thr Asp Cys Val Glu Thr Glu Glu Asn Pro
65                  70                  75                  80

Gln Val Tyr Phe Cys Cys Cys Glu Gly Asn Met Cys Asn Glu Lys Phe
                85                  90                  95

Ser Tyr Phe Pro Glu Met Glu Val Thr Gln Pro Thr Ser
            100                 105


<210> SEQ ID NO 15
<211> LENGTH: 451
<212> TYPE: PRT
<213> ORGANISM: Homo sapiens

<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Val Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 16
<211> LENGTH: 121
<212> TYPE: PRT
<213> ORGANISM: Homo sapiens

<400> SEQUENCE: 16

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120


<210> SEQ ID NO 17
<211> LENGTH: 214
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45
```

```
Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105


<210> SEQ ID NO 19
<211> LENGTH: 450
<212> TYPE: PRT
<213> ORGANISM: Artificial
<220> FEATURE:
<223> OTHER INFORMATION: Chimeric Anti-TNF-alpha antibody heavy chain
      amino acid sequence

<400> SEQUENCE: 19

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30
```

-continued

```
Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

```
    450


<210> SEQ ID NO 20
<211> LENGTH: 120
<212> TYPE: PRT
<213> ORGANISM: Artificial
<220> FEATURE:
<223> OTHER INFORMATION: Chimeric Anti-TNF-alpha antibody heavy chain
      variable region amino acid sequence

<400> SEQUENCE: 20

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser
        115                 120


<210> SEQ ID NO 21
<211> LENGTH: 214
<212> TYPE: PRT
<213> ORGANISM: Artificial
<220> FEATURE:
<223> OTHER INFORMATION: Chimeric Anti-TNF-alpha antibody light chain
      amino acid sequence

<400> SEQUENCE: 21

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

```
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 22
<211> LENGTH: 107
<212> TYPE: PRT
<213> ORGANISM: Artificial
<220> FEATURE:
<223> OTHER INFORMATION: Chimeric Anti-TNF-alpha antibody light chain
      variable region amino acid sequence

<400> SEQUENCE: 22

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Met Ser Gly Ile Pro Ser Arg Phe Ser Gly
    50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105


<210> SEQ ID NO 23
<211> LENGTH: 229
<212> TYPE: PRT
<213> ORGANISM: Artificial
<220> FEATURE:
<223> OTHER INFORMATION: Humanized Anti-TNF-alpha antibody heavy chain
      amino acid sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Ala Ala
225


<210> SEQ ID NO 24
<211> LENGTH: 118
<212> TYPE: PRT
<213> ORGANISM: Artificial
<220> FEATURE:
<223> OTHER INFORMATION: Humanized Anti-TNF-alpha antibody heavy chain
      variable region amino acid sequence

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Val Phe Thr Asp Tyr
            20                  25                  30

Gly Met Asn Trp Val Arg Gln Ala Pro Gly Lys Gly Leu Glu Trp Met
        35                  40                  45

Gly Trp Ile Asn Thr Tyr Ile Gly Glu Pro Ile Tyr Ala Asp Ser Val
    50                  55                  60

Lys Gly Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Arg Ser Tyr Ala Met Asp Tyr Trp Gly Gln Gly Thr
            100                 105                 110

Leu Val Thr Val Ser Ser
        115


<210> SEQ ID NO 25
<211> LENGTH: 214
<212> TYPE: PRT
<213> ORGANISM: Artificial
<220> FEATURE:
<223> OTHER INFORMATION: Humanized Anti-TNF-alpha antibody light chain
      amino acid sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 26
<211> LENGTH: 107
<212> TYPE: PRT
<213> ORGANISM: Artificial
<220> FEATURE:
<223> OTHER INFORMATION: Humanized Anti-TNF-alpha antibody light chain
      variable region amino acid sequence

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Phe Leu Tyr Ser Gly Val Pro Tyr Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Leu
                85                  90                  95

Thr Phe Gly Gln Gly Thr Lys Val Glu Ile Lys
            100                 105


<210> SEQ ID NO 27
<211> LENGTH: 456
<212> TYPE: PRT
<213> ORGANISM: Homo sapiens

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 28
```

```
<211> LENGTH: 126
<212> TYPE: PRT
<213> ORGANISM: Homo sapiens

<400> SEQUENCE: 28

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ala Ala Gly Gly Asn Tyr Tyr Tyr Tyr Gly
            100                 105                 110

Met Asp Val Trp Gly Gln Gly Thr Thr Val Thr Val Ser Ser
        115                 120                 125


<210> SEQ ID NO 29
<211> LENGTH: 215
<212> TYPE: PRT
<213> ORGANISM: Homo sapiens

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 30
<211> LENGTH: 108
<212> TYPE: PRT
<213> ORGANISM: Homo sapiens

<400> SEQUENCE: 30

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys
            100                 105
```

<210> SEQ ID NO 31
<211> LENGTH: 452
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220
```

```
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Val Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 32
<211> LENGTH: 122
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser
        115                 120
```

```
<210> SEQ ID NO 33
<211> LENGTH: 213
<212> TYPE: PRT
<213> ORGANISM: Homo sapiens

<400> SEQUENCE: 33

Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 34
<211> LENGTH: 106
<212> TYPE: PRT
<213> ORGANISM: Homo sapiens

<400> SEQUENCE: 34

Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu
            100                 105
```

<210> SEQ ID NO 35
<211> LENGTH: 453
<212> TYPE: PRT
<213> ORGANISM: Homo sapiens

<400> SEQUENCE: 35

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380
```

```
Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
    450


<210> SEQ ID NO 36
<211> LENGTH: 126
<212> TYPE: PRT
<213> ORGANISM: Homo sapiens

<400> SEQUENCE: 36

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser
        115                 120                 125


<210> SEQ ID NO 37
<211> LENGTH: 215
<212> TYPE: PRT
<213> ORGANISM: Homo sapiens

<400> SEQUENCE: 37

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 38
<211> LENGTH: 108
<212> TYPE: PRT
<213> ORGANISM: Homo sapiens

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 39
<211> LENGTH: 576
<212> TYPE: PRT
<213> ORGANISM: Artificial
<220> FEATURE:
<223> OTHER INFORMATION: A109 Heavy chain amino acid sequence

<400> SEQUENCE: 39

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
```

-continued

```
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Glu Thr Gln Glu Cys Leu Phe Phe Asn Ala Asn Trp Glu Lys
465                 470                 475                 480

Asp Arg Thr Asn Gln Thr Gly Val Glu Pro Cys Tyr Gly Asp Lys Asp
                485                 490                 495

Lys Arg Arg His Cys Phe Ala Thr Trp Lys Asn Ile Ser Gly Ser Ile
            500                 505                 510

Glu Ile Val Lys Gln Gly Cys Trp Leu Asp Asp Ile Asn Cys Tyr Asp
        515                 520                 525

Arg Thr Asp Cys Val Glu Lys Lys Asp Ser Pro Glu Val Tyr Phe Cys
    530                 535                 540
```

```
Cys Cys Glu Gly Asn Met Cys Asn Glu Lys Phe Ser Tyr Phe Pro Glu
545                 550                 555                 560

Met Glu Val Thr Gln Pro Thr Ser Asn Pro Val Thr Pro Lys Pro Pro
                565                 570                 575


<210> SEQ ID NO 40
<211> LENGTH: 575
<212> TYPE: PRT
<213> ORGANISM: Artificial
<220> FEATURE:
<223> OTHER INFORMATION: A201 Heavy chain amino acid sequence

<400> SEQUENCE: 40

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Ala Ile Leu Gly Arg Ser Glu Thr Gln Glu Cys Leu Phe
465                 470                 475                 480

Tyr Asn Ala Asn Trp Glu Leu Glu Arg Thr Asn Gln Thr Gly Val Glu
                485                 490                 495

Pro Cys Glu Gly Glu Lys Asp Lys Arg Leu His Cys Tyr Ala Thr Trp
            500                 505                 510

Arg Asn Ile Ser Gly Ser Ile Glu Ile Val Lys Lys Gly Cys Trp Leu
        515                 520                 525

Asp Asp Phe Asn Cys Tyr Asp Arg Thr Asp Cys Val Glu Thr Glu Glu
    530                 535                 540

Asn Pro Gln Val Tyr Phe Cys Cys Cys Glu Gly Asn Met Cys Asn Glu
545                 550                 555                 560

Lys Phe Ser Tyr Phe Pro Glu Met Glu Val Thr Gln Pro Thr Ser
                565                 570                 575


<210> SEQ ID NO 41
<211> LENGTH: 781
<212> TYPE: PRT
<213> ORGANISM: Artificial
<220> FEATURE:
<223> OTHER INFORMATION: A110 Heavy chain amino acid sequence

<400> SEQUENCE: 41

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Asn Cys Trp Leu Arg Gln Ala Lys Asn Gly Arg Cys Gln
465                 470                 475                 480

Val Leu Tyr Lys Thr Glu Leu Ser Lys Glu Glu Cys Cys Ser Thr Gly
                485                 490                 495

Arg Leu Ser Thr Ser Trp Thr Glu Glu Asp Val Asn Asp Asn Thr Leu
            500                 505                 510

Phe Lys Trp Met Ile Phe Asn Gly Gly Ala Pro Asn Cys Ile Pro Cys
        515                 520                 525

Lys Glu Thr Cys Glu Asn Val Asp Cys Gly Pro Gly Gln Ser Cys Val
    530                 535                 540
```

```
Val Asp Gln Thr Gly Ser Pro Arg Cys Val Cys Ala Pro Asp Cys Ser
545                 550                 555                 560

Asn Ile Thr Trp Lys Gly Pro Val Cys Gly Leu Asp Gly Lys Thr Tyr
                565                 570                 575

Arg Asn Glu Cys Ala Leu Leu Lys Ala Arg Cys Lys Glu Gln Pro Glu
            580                 585                 590

Leu Glu Val Gln Tyr Gln Gly Arg Cys Lys Lys Thr Cys Arg Asp Val
        595                 600                 605

Phe Cys Pro Gly Ser Ser Thr Cys Val Val Asp Gln Thr Asn Asn Ala
    610                 615                 620

Tyr Cys Val Thr Cys Asn Arg Ile Cys Pro Glu Pro Ala Ser Ser Glu
625                 630                 635                 640

Gln Tyr Leu Cys Gly Asn Asp Gly Val Thr Tyr Ser Ser Ala Cys His
                645                 650                 655

Leu Arg Lys Ala Thr Cys Leu Leu Gly Arg Ser Ile Gly Leu Ala Tyr
            660                 665                 670

Glu Gly Lys Cys Ile Lys Ala Lys Ser Cys Glu Asp Ile Gln Cys Thr
        675                 680                 685

Gly Gly Lys Lys Cys Leu Trp Asp Phe Lys Val Gly Arg Gly Arg Cys
    690                 695                 700

Ser Leu Cys Asp Glu Leu Cys Pro Asp Ser Lys Ser Asp Glu Pro Val
705                 710                 715                 720

Cys Ala Ser Asp Asn Ala Thr Tyr Ala Ser Glu Cys Ala Met Lys Glu
                725                 730                 735

Ala Ala Cys Ser Ser Gly Val Leu Leu Glu Val Lys His Ser Gly Ser
            740                 745                 750

Cys Asn Ser Ile Ser Glu Asp Thr Glu Glu Glu Glu Glu Asp Glu Asp
        755                 760                 765

Gln Asp Tyr Ser Phe Pro Ile Ser Ser Ile Leu Glu Trp
    770                 775                 780


<210> SEQ ID NO 42
<211> LENGTH: 781
<212> TYPE: PRT
<213> ORGANISM: Artificial
<220> FEATURE:
<223> OTHER INFORMATION: A301 Heavy chain amino acid sequence

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Asn Cys Trp Leu Arg Gln Ala Lys Asn Gly Arg Cys Gln
465                 470                 475                 480

Val Leu Tyr Lys Thr Glu Leu Ser Lys Glu Glu Cys Cys Ser Thr Gly
                485                 490                 495

Arg Leu Ser Thr Ser Trp Thr Glu Glu Asp Val Asn Asp Asn Thr Leu
            500                 505                 510

Phe Lys Trp Met Ile Phe Asn Gly Gly Ala Pro Asn Cys Ile Pro Cys
        515                 520                 525

Lys Glu Thr Cys Glu Asn Val Asp Cys Gly Pro Gly Lys Lys Cys Arg
    530                 535                 540

Met Asn Lys Lys Asn Lys Pro Arg Cys Val Cys Ala Pro Asp Cys Ser
```

```
545                 550                 555                 560

Asn Ile Thr Trp Lys Gly Pro Val Cys Gly Leu Asp Gly Lys Thr Tyr
                565                 570                 575

Arg Asn Glu Cys Ala Leu Leu Lys Ala Arg Cys Lys Glu Gln Pro Glu
            580                 585                 590

Leu Glu Val Gln Tyr Gln Gly Arg Cys Lys Lys Thr Cys Arg Asp Val
        595                 600                 605

Phe Cys Pro Gly Ser Ser Thr Cys Val Val Asp Gln Thr Asn Asn Ala
    610                 615                 620

Tyr Cys Val Thr Cys Asn Arg Ile Cys Pro Glu Pro Ala Ser Ser Glu
625                 630                 635                 640

Gln Tyr Leu Cys Gly Asn Asp Gly Val Thr Tyr Ser Ser Ala Cys His
                645                 650                 655

Leu Arg Lys Ala Thr Cys Leu Leu Gly Arg Ser Ile Gly Leu Ala Tyr
            660                 665                 670

Glu Gly Lys Cys Ile Lys Ala Lys Ser Cys Glu Asp Ile Gln Cys Thr
        675                 680                 685

Gly Gly Lys Lys Cys Leu Trp Asp Phe Lys Val Gly Arg Gly Arg Cys
    690                 695                 700

Ser Leu Cys Asp Glu Leu Cys Pro Asp Ser Lys Ser Asp Glu Pro Val
705                 710                 715                 720

Cys Ala Ser Asp Asn Ala Thr Tyr Ala Ser Glu Cys Ala Met Lys Glu
                725                 730                 735

Ala Ala Cys Ser Ser Gly Val Leu Leu Glu Val Lys His Ser Gly Ser
            740                 745                 750

Cys Asn Ser Ile Ser Glu Asp Thr Glu Glu Glu Glu Glu Asp Glu Asp
        755                 760                 765

Gln Asp Tyr Ser Phe Pro Ile Ser Ser Ile Leu Glu Trp
    770                 775                 780


<210> SEQ ID NO 43
<211> LENGTH: 754
<212> TYPE: PRT
<213> ORGANISM: Artificial
<220> FEATURE:
<223> OTHER INFORMATION: A304 Heavy chain amino acid sequence

<400> SEQUENCE: 43

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
```

```
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Gly Asn Cys Trp Leu Arg Gln Ala Lys Asn Gly Arg Cys Gln
465                 470                 475                 480

Val Leu Tyr Lys Thr Glu Leu Ser Lys Glu Glu Cys Cys Ser Thr Gly
                485                 490                 495

Arg Leu Ser Thr Ser Trp Thr Glu Glu Asp Val Asn Asp Asn Thr Leu
            500                 505                 510

Phe Lys Trp Met Ile Phe Asn Gly Gly Ala Pro Asn Cys Ile Pro Cys
        515                 520                 525

Lys Glu Thr Cys Glu Asn Val Asp Cys Gly Pro Gly Lys Lys Cys Arg
    530                 535                 540

Met Asn Lys Lys Asn Lys Pro Arg Cys Val Cys Ala Pro Asp Cys Ser
545                 550                 555                 560
```

```
Asn Ile Thr Trp Lys Gly Pro Val Cys Gly Leu Asp Gly Lys Thr Tyr
                565                 570                 575

Arg Asn Glu Cys Ala Leu Leu Lys Ala Arg Cys Lys Glu Gln Pro Glu
            580                 585                 590

Leu Glu Val Gln Tyr Gln Gly Arg Cys Lys Lys Thr Cys Arg Asp Val
        595                 600                 605

Phe Cys Pro Gly Ser Ser Thr Cys Val Val Asp Gln Thr Asn Asn Ala
    610                 615                 620

Tyr Cys Val Thr Cys Asn Arg Ile Cys Pro Glu Pro Ala Ser Ser Glu
625                 630                 635                 640

Gln Tyr Leu Cys Gly Asn Asp Gly Val Thr Tyr Ser Ser Ala Cys His
                645                 650                 655

Leu Arg Lys Ala Thr Cys Leu Leu Gly Arg Ser Ile Gly Leu Ala Tyr
            660                 665                 670

Glu Gly Lys Cys Ile Lys Ala Lys Ser Cys Glu Asp Ile Gln Cys Thr
        675                 680                 685

Gly Gly Lys Lys Cys Leu Trp Asp Phe Lys Val Gly Arg Gly Arg Cys
    690                 695                 700

Ser Leu Cys Asp Glu Leu Cys Pro Asp Ser Lys Ser Asp Glu Pro Val
705                 710                 715                 720

Cys Ala Ser Asp Asn Ala Thr Tyr Ala Ser Glu Cys Ala Met Lys Glu
                725                 730                 735

Ala Ala Cys Ser Ser Gly Val Leu Leu Glu Val Lys His Ser Gly Ser
            740                 745                 750

Cys Asn


<210> SEQ ID NO 44
<211> LENGTH: 576
<212> TYPE: PRT
<213> ORGANISM: Artificial
<220> FEATURE:
<223> OTHER INFORMATION: A410 Heavy chain amino acid sequence

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Glu Thr Arg Glu Cys Ile Tyr Tyr Asn Ala Asn Trp Glu Leu
465                 470                 475                 480

Glu Arg Thr Asn Gln Ser Gly Leu Glu Arg Cys Glu Gly Glu Gln Asp
                485                 490                 495

Lys Arg Leu His Cys Tyr Ala Ser Trp Arg Asn Ser Ser Gly Thr Ile
            500                 505                 510

Glu Leu Val Lys Lys Gly Cys Trp Leu Asp Asp Phe Asn Cys Tyr Asp
        515                 520                 525

Arg Gln Glu Cys Val Ala Thr Glu Glu Asn Pro Gln Val Tyr Phe Cys
    530                 535                 540

Cys Cys Glu Gly Asn Phe Cys Asn Glu Arg Phe Thr His Leu Pro Glu
545                 550                 555                 560

Ala Gly Gly Pro Glu Val Thr Tyr Glu Pro Pro Pro Thr Ala Pro Thr
                565                 570                 575
```

<210> SEQ ID NO 45
<211> LENGTH: 576
<212> TYPE: PRT
<213> ORGANISM: Artificial
<220> FEATURE:
<223> OTHER INFORMATION: A401 Heavy chain amino acid sequence

<400> SEQUENCE: 45

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
```

```
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Glu Thr Arg Glu Cys Ile Tyr Tyr Asn Ala Asn Trp Glu Leu
465                 470                 475                 480

Glu Arg Thr Asn Gln Ser Gly Leu Glu Arg Cys Glu Gly Asp Gln Asp
                485                 490                 495

Lys Arg Leu His Cys Tyr Ala Ser Trp Arg Asn Ser Ser Gly Thr Ile
            500                 505                 510

Glu Leu Val Lys Lys Gly Cys Trp Leu Asp Asp Ile Asn Cys Tyr Asp
        515                 520                 525

Arg Gln Glu Cys Val Ala Thr Lys Glu Asn Pro Gln Val Tyr Phe Cys
    530                 535                 540

Cys Cys Glu Gly Asn Phe Cys Asn Glu Arg Phe Thr His Leu Pro Glu
545                 550                 555                 560

Ala Gly Gly Pro Glu Val Thr Tyr Glu Pro Pro Pro Thr Ala Pro Thr
                565                 570                 575


<210> SEQ ID NO 46
<211> LENGTH: 576
<212> TYPE: PRT
<213> ORGANISM: Artificial
<220> FEATURE:
<223> OTHER INFORMATION: A404 Heavy chain amino acid sequence

<400> SEQUENCE: 46

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Glu Thr Arg Glu Cys Ile Tyr Tyr Asn Ala Asn Trp Glu Leu
465                 470                 475                 480

Glu Arg Thr Asn Gln Ser Gly Leu Glu Arg Cys Tyr Gly Asp Lys Asp
                485                 490                 495

Lys Arg Arg His Cys Tyr Ala Ser Trp Arg Asn Ser Ser Gly Thr Ile
            500                 505                 510

Glu Leu Val Lys Lys Gly Cys Trp Leu Asp Asp Phe Asn Cys Tyr Asp
        515                 520                 525

Arg Gln Glu Cys Val Ala Thr Glu Glu Asn Pro Gln Val Tyr Phe Cys
    530                 535                 540

Cys Cys Glu Gly Asn Phe Cys Asn Glu Arg Phe Thr His Leu Pro Glu
545                 550                 555                 560

Ala Gly Gly Pro Glu Val Thr Tyr Glu Pro Pro Pro Thr Ala Pro Thr
                565                 570                 575
```

<210> SEQ ID NO 47

<211> LENGTH: 573
<212> TYPE: PRT
<213> ORGANISM: Artificial
<220> FEATURE:
<223> OTHER INFORMATION: A407 Heavy chain amino acid sequence

<400> SEQUENCE: 47

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Glu Thr Arg Glu Cys Ile Tyr Tyr Asn Ala Asn Trp Glu Leu
465                 470                 475                 480

Glu Arg Thr Asn Gln Ser Gly Leu Glu Arg Cys Glu Gly Glu Gln Asp
                485                 490                 495

Lys Arg Leu His Cys Tyr Ala Ser Trp Arg Asn Ser Ser Gly Thr Ile
            500                 505                 510

Glu Leu Val Lys Lys Gly Cys Trp Asp Asp Asp Phe Asn Cys Tyr Asp
        515                 520                 525

Arg Gln Glu Cys Val Ala Thr Glu Glu Asn Pro Gln Val Tyr Phe Cys
    530                 535                 540

Cys Cys Glu Gly Asn Phe Cys Asn Glu Arg Phe Thr His Leu Pro Glu
545                 550                 555                 560

Ala Gly Gly Pro Glu Val Thr Tyr Glu Pro Pro Pro Thr
                565                 570


<210> SEQ ID NO 48
<211> LENGTH: 562
<212> TYPE: PRT
<213> ORGANISM: Artificial
<220> FEATURE:
<223> OTHER INFORMATION: A710 amino acid sequence

<400> SEQUENCE: 48

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175
```

```
Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Glu Thr Gln Glu Cys Leu Phe Phe Asn Ala Asn Trp
    450                 455                 460

Glu Lys Asp Arg Thr Asn Gln Thr Gly Val Glu Pro Cys Tyr Gly Asp
465                 470                 475                 480

Lys Asp Lys Arg Arg His Cys Phe Ala Thr Trp Lys Asn Ile Ser Gly
                485                 490                 495

Ser Ile Glu Ile Val Lys Gln Gly Cys Trp Leu Asp Asp Ile Asn Cys
            500                 505                 510

Tyr Asp Arg Thr Asp Cys Val Glu Lys Lys Asp Ser Pro Glu Val Tyr
        515                 520                 525

Phe Cys Cys Cys Glu Gly Asn Met Cys Asn Glu Lys Phe Ser Tyr Phe
    530                 535                 540

Pro Glu Met Glu Val Thr Gln Pro Thr Ser Asn Pro Val Thr Pro Lys
545                 550                 555                 560

Pro Pro
```

<210> SEQ ID NO 49
<211> LENGTH: 562
<212> TYPE: PRT

<213> ORGANISM: Artificial
<220> FEATURE:
<223> OTHER INFORMATION: A711 amino acid sequence

<400> SEQUENCE: 49

```
Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
```

```
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Glu Thr Arg Glu Cys Ile Tyr Tyr Asn Ala Asn Trp
    450                 455                 460

Glu Leu Glu Arg Thr Asn Gln Ser Gly Leu Glu Arg Cys Glu Gly Glu
465                 470                 475                 480

Gln Asp Lys Arg Leu His Cys Tyr Ala Ser Trp Arg Asn Ser Ser Gly
                485                 490                 495

Thr Ile Glu Leu Val Lys Lys Gly Cys Trp Leu Asp Asp Phe Asn Cys
            500                 505                 510

Tyr Asp Arg Gln Glu Cys Val Ala Thr Glu Glu Asn Pro Gln Val Tyr
        515                 520                 525

Phe Cys Cys Cys Glu Gly Asn Phe Cys Asn Glu Arg Phe Thr His Leu
    530                 535                 540

Pro Glu Ala Gly Gly Pro Glu Val Thr Tyr Glu Pro Pro Pro Thr Ala
545                 550                 555                 560

Pro Thr


<210> SEQ ID NO 50
<211> LENGTH: 562
<212> TYPE: PRT
<213> ORGANISM: Artificial
<220> FEATURE:
<223> OTHER INFORMATION: A713 amino acid sequence

<400> SEQUENCE: 50

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190
```

```
Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Glu Thr Arg Glu Cys Ile Tyr Tyr Asn Ala Asn Trp
    450                 455                 460

Glu Leu Glu Arg Thr Asn Gln Ser Gly Leu Glu Arg Cys Glu Gly Asp
465                 470                 475                 480

Gln Asp Lys Arg Leu His Cys Tyr Ala Ser Trp Arg Asn Ser Ser Gly
                485                 490                 495

Thr Ile Glu Leu Val Lys Lys Gly Cys Trp Leu Asp Asp Ile Asn Cys
            500                 505                 510

Tyr Asp Arg Gln Glu Cys Val Ala Thr Lys Glu Asn Pro Gln Val Tyr
        515                 520                 525

Phe Cys Cys Cys Glu Gly Asn Phe Cys Asn Glu Arg Phe Thr His Leu
    530                 535                 540

Pro Glu Ala Gly Gly Pro Glu Val Thr Tyr Glu Pro Pro Pro Thr Ala
545                 550                 555                 560

Pro Thr
```

<210> SEQ ID NO 51
<211> LENGTH: 562
<212> TYPE: PRT
<213> ORGANISM: Artificial
<220> FEATURE:
<223> OTHER INFORMATION: A714 amino acid sequence

<400> SEQUENCE: 51

```
Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
```

```
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Glu Thr Arg Glu Cys Ile Tyr Tyr Asn Ala Asn Trp
    450                 455                 460

Glu Leu Glu Arg Thr Asn Gln Ser Gly Leu Glu Arg Cys Tyr Gly Asp
465                 470                 475                 480

Lys Asp Lys Arg Arg His Cys Tyr Ala Ser Trp Arg Asn Ser Ser Gly
                485                 490                 495

Thr Ile Glu Leu Val Lys Lys Gly Cys Trp Leu Asp Asp Phe Asn Cys
            500                 505                 510

Tyr Asp Arg Gln Glu Cys Val Ala Thr Glu Glu Asn Pro Gln Val Tyr
        515                 520                 525

Phe Cys Cys Cys Glu Gly Asn Phe Cys Asn Glu Arg Phe Thr His Leu
    530                 535                 540

Pro Glu Ala Gly Gly Pro Glu Val Thr Tyr Glu Pro Pro Pro Thr Ala
545                 550                 555                 560

Pro Thr


<210> SEQ ID NO 52
<211> LENGTH: 559
<212> TYPE: PRT
<213> ORGANISM: Artificial
<220> FEATURE:
<223> OTHER INFORMATION: A715 amino acid sequence

<400> SEQUENCE: 52

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205
```

```
Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Glu Thr Arg Glu Cys Ile Tyr Tyr Asn Ala Asn Trp
    450                 455                 460

Glu Leu Glu Arg Thr Asn Gln Ser Gly Leu Glu Arg Cys Glu Gly Glu
465                 470                 475                 480

Gln Asp Lys Arg Leu His Cys Tyr Ala Ser Trp Arg Asn Ser Ser Gly
                485                 490                 495

Thr Ile Glu Leu Val Lys Lys Gly Cys Trp Asp Asp Asp Phe Asn Cys
            500                 505                 510

Tyr Asp Arg Gln Glu Cys Val Ala Thr Glu Glu Asn Pro Gln Val Tyr
        515                 520                 525

Phe Cys Cys Cys Glu Gly Asn Phe Cys Asn Glu Arg Phe Thr His Leu
    530                 535                 540

Pro Glu Ala Gly Gly Pro Glu Val Thr Tyr Glu Pro Pro Pro Thr
545                 550                 555


<210> SEQ ID NO 53
<211> LENGTH: 561
<212> TYPE: PRT
<213> ORGANISM: Artificial
<220> FEATURE:
<223> OTHER INFORMATION: A716 amino acid sequence

<400> SEQUENCE: 53

Ile Tyr Pro Ser Gly Val Ile Gly Leu Val Pro His Leu Gly Asp Arg
1               5                   10                  15
```

```
Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430
```

```
Leu Ser Pro Gly Lys Gly Gly Gly Gly Ser Gly Gly Gly Gly Ser Gly
        435                 440                 445

Gly Gly Gly Ser Gly Ala Ile Leu Gly Arg Ser Glu Thr Gln Glu Cys
    450                 455                 460

Leu Phe Tyr Asn Ala Asn Trp Glu Leu Glu Arg Thr Asn Gln Thr Gly
465                 470                 475                 480

Val Glu Pro Cys Glu Gly Glu Lys Asp Lys Arg Leu His Cys Tyr Ala
                485                 490                 495

Thr Trp Arg Asn Ile Ser Gly Ser Ile Glu Ile Val Lys Lys Gly Cys
            500                 505                 510

Trp Leu Asp Asp Phe Asn Cys Tyr Asp Arg Thr Asp Cys Val Glu Thr
        515                 520                 525

Glu Glu Asn Pro Gln Val Tyr Phe Cys Cys Cys Glu Gly Asn Met Cys
    530                 535                 540

Asn Glu Lys Phe Ser Tyr Phe Pro Glu Met Glu Val Thr Gln Pro Thr
545                 550                 555                 560

Ser


<210> SEQ ID NO 54
<211> LENGTH: 767
<212> TYPE: PRT
<213> ORGANISM: Artificial
<220> FEATURE:
<223> OTHER INFORMATION: A712 amino acid sequence

<400> SEQUENCE: 54

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
```

```
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Gly Asn Cys Trp Leu Arg Gln Ala Lys Asn Gly Arg
    450                 455                 460

Cys Gln Val Leu Tyr Lys Thr Glu Leu Ser Lys Glu Glu Cys Cys Ser
465                 470                 475                 480

Thr Gly Arg Leu Ser Thr Ser Trp Thr Glu Glu Asp Val Asn Asp Asn
                485                 490                 495

Thr Leu Phe Lys Trp Met Ile Phe Asn Gly Gly Ala Pro Asn Cys Ile
            500                 505                 510

Pro Cys Lys Glu Thr Cys Glu Asn Val Asp Cys Gly Pro Gly Gln Ser
        515                 520                 525

Cys Val Val Asp Gln Thr Gly Ser Pro Arg Cys Val Cys Ala Pro Asp
    530                 535                 540

Cys Ser Asn Ile Thr Trp Lys Gly Pro Val Cys Gly Leu Asp Gly Lys
545                 550                 555                 560

Thr Tyr Arg Asn Glu Cys Ala Leu Leu Lys Ala Arg Cys Lys Glu Gln
                565                 570                 575

Pro Glu Leu Glu Val Gln Tyr Gln Gly Arg Cys Lys Lys Thr Cys Arg
            580                 585                 590

Asp Val Phe Cys Pro Gly Ser Ser Thr Cys Val Val Asp Gln Thr Asn
        595                 600                 605

Asn Ala Tyr Cys Val Thr Cys Asn Arg Ile Cys Pro Glu Pro Ala Ser
    610                 615                 620

Ser Glu Gln Tyr Leu Cys Gly Asn Asp Gly Val Thr Tyr Ser Ser Ala
625                 630                 635                 640

Cys His Leu Arg Lys Ala Thr Cys Leu Leu Gly Arg Ser Ile Gly Leu
                645                 650                 655
```

Ala Tyr Glu Gly Lys Cys Ile Lys Ala Lys Ser Cys Glu Asp Ile Gln
660 665 670

Cys Thr Gly Gly Lys Lys Cys Leu Trp Asp Phe Lys Val Gly Arg Gly
675 680 685

Arg Cys Ser Leu Cys Asp Glu Leu Cys Pro Asp Ser Lys Ser Asp Glu
690 695 700

Pro Val Cys Ala Ser Asp Asn Ala Thr Tyr Ala Ser Glu Cys Ala Met
705 710 715 720

Lys Glu Ala Ala Cys Ser Ser Gly Val Leu Leu Glu Val Lys His Ser
725 730 735

Gly Ser Cys Asn Ser Ile Ser Glu Asp Thr Glu Glu Glu Glu Glu Asp
740 745 750

Glu Asp Gln Asp Tyr Ser Phe Pro Ile Ser Ser Ile Leu Glu Trp
755 760 765

<210> SEQ ID NO 55
<211> LENGTH: 767
<212> TYPE: PRT
<213> ORGANISM: Artificial
<220> FEATURE:
<223> OTHER INFORMATION: A717 amino acid sequence

<400> SEQUENCE: 55

Ile Tyr Pro Ser Gly Val Ile Gly Leu Val Pro His Leu Gly Asp Arg
1 5 10 15

Glu Lys Arg Asp Ser Val Cys Pro Gln Gly Lys Tyr Ile His Pro Gln
20 25 30

Asn Asn Ser Ile Cys Cys Thr Lys Cys His Lys Gly Thr Tyr Leu Tyr
35 40 45

Asn Asp Cys Pro Gly Pro Gly Gln Asp Thr Asp Cys Arg Glu Cys Glu
50 55 60

Ser Gly Ser Phe Thr Ala Ser Glu Asn His Leu Arg His Cys Leu Ser
65 70 75 80

Cys Ser Lys Cys Arg Lys Glu Met Gly Gln Val Glu Ile Ser Ser Cys
85 90 95

Thr Val Asp Arg Asp Thr Val Cys Gly Cys Arg Lys Asn Gln Tyr Arg
100 105 110

His Tyr Trp Ser Glu Asn Leu Phe Gln Cys Phe Asn Cys Ser Leu Cys
115 120 125

Leu Asn Gly Thr Val His Leu Ser Cys Gln Glu Lys Gln Asn Thr Val
130 135 140

Cys Thr Cys His Ala Gly Phe Phe Leu Arg Glu Asn Glu Cys Val Ser
145 150 155 160

Cys Ser Asn Cys Lys Lys Ser Leu Glu Cys Thr Lys Leu Cys Leu Pro
165 170 175

Gln Ile Glu Asn Val Lys Gly Thr Glu Asp Ser Gly Thr Thr Gly Gly
180 185 190

Gly Gly Ser Gly Gly Gly Gly Ser Gly Gly Gly Gly Ser Glu Pro Lys
195 200 205

Ser Cys Asp Lys Thr His Thr Cys Pro Pro Cys Pro Ala Pro Glu Leu
210 215 220

Leu Gly Gly Pro Ser Val Phe Leu Phe Pro Pro Lys Pro Lys Asp Thr
225 230 235 240

Leu Met Ile Ser Arg Thr Pro Glu Val Thr Cys Val Val Val Asp Val
245 250 255

```
Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Gly Asn Cys Trp Leu Arg Gln Ala Lys Asn Gly Arg
    450                 455                 460

Cys Gln Val Leu Tyr Lys Thr Glu Leu Ser Lys Glu Glu Cys Cys Ser
465                 470                 475                 480

Thr Gly Arg Leu Ser Thr Ser Trp Thr Glu Glu Asp Val Asn Asp Asn
                485                 490                 495

Thr Leu Phe Lys Trp Met Ile Phe Asn Gly Gly Ala Pro Asn Cys Ile
            500                 505                 510

Pro Cys Lys Glu Thr Cys Glu Asn Val Asp Cys Gly Pro Gly Lys Lys
        515                 520                 525

Cys Arg Met Asn Lys Lys Asn Lys Pro Arg Cys Val Cys Ala Pro Asp
    530                 535                 540

Cys Ser Asn Ile Thr Trp Lys Gly Pro Val Cys Gly Leu Asp Gly Lys
545                 550                 555                 560

Thr Tyr Arg Asn Glu Cys Ala Leu Leu Lys Ala Arg Cys Lys Glu Gln
                565                 570                 575

Pro Glu Leu Glu Val Gln Tyr Gln Gly Arg Cys Lys Lys Thr Cys Arg
            580                 585                 590

Asp Val Phe Cys Pro Gly Ser Ser Thr Cys Val Val Asp Gln Thr Asn
        595                 600                 605

Asn Ala Tyr Cys Val Thr Cys Asn Arg Ile Cys Pro Glu Pro Ala Ser
    610                 615                 620

Ser Glu Gln Tyr Leu Cys Gly Asn Asp Gly Val Thr Tyr Ser Ser Ala
625                 630                 635                 640

Cys His Leu Arg Lys Ala Thr Cys Leu Leu Gly Arg Ser Ile Gly Leu
                645                 650                 655

Ala Tyr Glu Gly Lys Cys Ile Lys Ala Lys Ser Cys Glu Asp Ile Gln
            660                 665                 670
```

```
Cys Thr Gly Gly Lys Lys Cys Leu Trp Asp Phe Lys Val Gly Arg Gly
        675                 680                 685

Arg Cys Ser Leu Cys Asp Glu Leu Cys Pro Asp Ser Lys Ser Asp Glu
    690                 695                 700

Pro Val Cys Ala Ser Asp Asn Ala Thr Tyr Ala Ser Glu Cys Ala Met
705                 710                 715                 720

Lys Glu Ala Ala Cys Ser Ser Gly Val Leu Leu Glu Val Lys His Ser
                725                 730                 735

Gly Ser Cys Asn Ser Ile Ser Glu Asp Thr Glu Glu Glu Glu Glu Asp
            740                 745                 750

Glu Asp Gln Asp Tyr Ser Phe Pro Ile Ser Ser Ile Leu Glu Trp
        755                 760                 765


<210> SEQ ID NO 56
<211> LENGTH: 740
<212> TYPE: PRT
<213> ORGANISM: Artificial
<220> FEATURE:
<223> OTHER INFORMATION: A718 amino acid sequence

<400> SEQUENCE: 56

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
    50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
    130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr Gly Gly
            180                 185                 190

Gly Gly Ser Gly Gly Gly Gly Ser Gly Gly Gly Gly Ser Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270
```

```
Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys Gly Gly Gly Gly Ser Gly Gly Gly Gly Ser Gly
        435                 440                 445

Gly Gly Gly Ser Gly Asn Cys Trp Leu Arg Gln Ala Lys Asn Gly Arg
    450                 455                 460

Cys Gln Val Leu Tyr Lys Thr Glu Leu Ser Lys Glu Glu Cys Cys Ser
465                 470                 475                 480

Thr Gly Arg Leu Ser Thr Ser Trp Thr Glu Glu Asp Val Asn Asp Asn
                485                 490                 495

Thr Leu Phe Lys Trp Met Ile Phe Asn Gly Gly Ala Pro Asn Cys Ile
            500                 505                 510

Pro Cys Lys Glu Thr Cys Glu Asn Val Asp Cys Gly Pro Gly Lys Lys
        515                 520                 525

Cys Arg Met Asn Lys Lys Asn Lys Pro Arg Cys Val Cys Ala Pro Asp
    530                 535                 540

Cys Ser Asn Ile Thr Trp Lys Gly Pro Val Cys Gly Leu Asp Gly Lys
545                 550                 555                 560

Thr Tyr Arg Asn Glu Cys Ala Leu Leu Lys Ala Arg Cys Lys Glu Gln
                565                 570                 575

Pro Glu Leu Glu Val Gln Tyr Gln Gly Arg Cys Lys Lys Thr Cys Arg
            580                 585                 590

Asp Val Phe Cys Pro Gly Ser Ser Thr Cys Val Val Asp Gln Thr Asn
        595                 600                 605

Asn Ala Tyr Cys Val Thr Cys Asn Arg Ile Cys Pro Glu Pro Ala Ser
    610                 615                 620

Ser Glu Gln Tyr Leu Cys Gly Asn Asp Gly Val Thr Tyr Ser Ser Ala
625                 630                 635                 640

Cys His Leu Arg Lys Ala Thr Cys Leu Leu Gly Arg Ser Ile Gly Leu
                645                 650                 655

Ala Tyr Glu Gly Lys Cys Ile Lys Ala Lys Ser Cys Glu Asp Ile Gln
            660                 665                 670

Cys Thr Gly Gly Lys Lys Cys Leu Trp Asp Phe Lys Val Gly Arg Gly
        675                 680                 685

Arg Cys Ser Leu Cys Asp Glu Leu Cys Pro Asp Ser Lys Ser Asp Glu
```

```
    690                 695                 700

Pro Val Cys Ala Ser Asp Asn Ala Thr Tyr Ala Ser Glu Cys Ala Met
705                 710                 715                 720

Lys Glu Ala Ala Cys Ser Ser Gly Val Leu Leu Glu Val Lys His Ser
                725                 730                 735

Gly Ser Cys Asn
            740


<210> SEQ ID NO 57
<211> LENGTH: 654
<212> TYPE: PRT
<213> ORGANISM: Homo sapiens

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Gly Ser Gly Gly Gly Gly Ser Gly Gly Gly Gly Ser
    450                 455                 460

Ile Tyr Pro Ser Gly Val Ile Gly Leu Val Pro His Leu Gly Asp Arg
465                 470                 475                 480

Glu Lys Arg Asp Ser Val Cys Pro Gln Gly Lys Tyr Ile His Pro Gln
                485                 490                 495

Asn Asn Ser Ile Cys Cys Thr Lys Cys His Lys Gly Thr Tyr Leu Tyr
            500                 505                 510

Asn Asp Cys Pro Gly Pro Gly Gln Asp Thr Asp Cys Arg Glu Cys Glu
        515                 520                 525

Ser Gly Ser Phe Thr Ala Ser Glu Asn His Leu Arg His Cys Leu Ser
    530                 535                 540

Cys Ser Lys Cys Arg Lys Glu Met Gly Gln Val Glu Ile Ser Ser Cys
545                 550                 555                 560

Thr Val Asp Arg Asp Thr Val Cys Gly Cys Arg Lys Asn Gln Tyr Arg
                565                 570                 575

His Tyr Trp Ser Glu Asn Leu Phe Gln Cys Phe Asn Cys Ser Leu Cys
            580                 585                 590

Leu Asn Gly Thr Val His Leu Ser Cys Gln Glu Lys Gln Asn Thr Val
        595                 600                 605

Cys Thr Cys His Ala Gly Phe Phe Leu Arg Glu Asn Glu Cys Val Ser
    610                 615                 620

Cys Ser Asn Cys Lys Lys Ser Leu Glu Cys Thr Lys Leu Cys Leu Pro
625                 630                 635                 640

Gln Ile Glu Asn Val Lys Gly Thr Glu Asp Ser Gly Thr Thr
                645                 650
```

<210> SEQ ID NO 58
<211> LENGTH: 658
<212> TYPE: PRT
<213> ORGANISM: Homo sapiens

<400> SEQUENCE: 58

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45
```

```
Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys Gly Gly Gly Gly Ser Gly Gly Gly Gly Ser Gly
    450                 455                 460
```

```
Gly Gly Gly Ser Ile Tyr Pro Ser Gly Val Ile Gly Leu Val Pro His
465                 470                 475                 480

Leu Gly Asp Arg Glu Lys Arg Asp Ser Val Cys Pro Gln Gly Lys Tyr
                485                 490                 495

Ile His Pro Gln Asn Asn Ser Ile Cys Cys Thr Lys Cys His Lys Gly
            500                 505                 510

Thr Tyr Leu Tyr Asn Asp Cys Pro Gly Pro Gly Gln Asp Thr Asp Cys
        515                 520                 525

Arg Glu Cys Glu Ser Gly Ser Phe Thr Ala Ser Glu Asn His Leu Arg
    530                 535                 540

His Cys Leu Ser Cys Ser Lys Cys Arg Lys Glu Met Gly Gln Val Glu
545                 550                 555                 560

Ile Ser Ser Cys Thr Val Asp Arg Asp Thr Val Cys Gly Cys Arg Lys
                565                 570                 575

Asn Gln Tyr Arg His Tyr Trp Ser Glu Asn Leu Phe Gln Cys Phe Asn
            580                 585                 590

Cys Ser Leu Cys Leu Asn Gly Thr Val His Leu Ser Cys Gln Glu Lys
        595                 600                 605

Gln Asn Thr Val Cys Thr Cys His Ala Gly Phe Phe Leu Arg Glu Asn
    610                 615                 620

Glu Cys Val Ser Cys Ser Asn Cys Lys Lys Ser Leu Glu Cys Thr Lys
625                 630                 635                 640

Leu Cys Leu Pro Gln Ile Glu Asn Val Lys Gly Thr Glu Asp Ser Gly
                645                 650                 655

Thr Thr


<210> SEQ ID NO 59
<211> LENGTH: 607
<212> TYPE: PRT
<213> ORGANISM: Artificial
<220> FEATURE:
<223> OTHER INFORMATION: A211 amino acid sequence

<400> SEQUENCE: 59

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
```

```
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Glu Thr Gln Glu Cys Leu Phe Phe Asn Ala Asn Trp Glu Lys Asp
            500                 505                 510

Arg Thr Asn Gln Thr Gly Val Glu Pro Cys Tyr Gly Asp Lys Asp Lys
        515                 520                 525

Arg Arg His Cys Phe Ala Thr Trp Lys Asn Ile Ser Gly Ser Ile Glu
    530                 535                 540

Ile Val Lys Gln Gly Cys Trp Leu Asp Asp Ile Asn Cys Tyr Asp Arg
545                 550                 555                 560

Thr Asp Cys Val Glu Lys Lys Asp Ser Pro Glu Val Tyr Phe Cys Cys
                565                 570                 575

Cys Glu Gly Asn Met Cys Asn Glu Lys Phe Ser Tyr Phe Pro Glu Met
            580                 585                 590
```

```
Glu Val Thr Gln Pro Thr Ser Asn Pro Val Thr Pro Lys Pro Pro
        595                 600                 605


<210> SEQ ID NO 60
<211> LENGTH: 607
<212> TYPE: PRT
<213> ORGANISM: Artificial
<220> FEATURE:
<223> OTHER INFORMATION: A305 amino acid sequence

<400> SEQUENCE: 60

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350
```

Glu Tyr Lys Cys Lys Val Ser Asn Lys Ala Leu Pro Ala Pro Ile Glu
355 360 365

Lys Thr Ile Ser Lys Ala Lys Gly Gln Pro Arg Glu Pro Gln Val Tyr
370 375 380

Thr Leu Pro Pro Ser Arg Glu Glu Met Thr Lys Asn Gln Val Ser Leu
385 390 395 400

Thr Cys Leu Val Lys Gly Phe Tyr Pro Ser Asp Ile Ala Val Glu Trp
405 410 415

Glu Ser Asn Gly Gln Pro Glu Asn Asn Tyr Lys Thr Thr Pro Pro Val
420 425 430

Leu Asp Ser Asp Gly Ser Phe Phe Leu Tyr Ser Lys Leu Thr Val Asp
435 440 445

Lys Ser Arg Trp Gln Gln Gly Asn Val Phe Ser Cys Ser Val Met His
450 455 460

Glu Ala Leu His Asn His Tyr Thr Gln Lys Ser Leu Ser Leu Ser Pro
465 470 475 480

Gly Lys Gly Gly Gly Gly Ser Gly Gly Gly Gly Ser Gly Gly Gly Gly
485 490 495

Ser Glu Thr Arg Glu Cys Ile Tyr Tyr Asn Ala Asn Trp Glu Leu Glu
500 505 510

Arg Thr Asn Gln Ser Gly Leu Glu Arg Cys Glu Gly Glu Gln Asp Lys
515 520 525

Arg Leu His Cys Tyr Ala Ser Trp Arg Asn Ser Ser Gly Thr Ile Glu
530 535 540

Leu Val Lys Lys Gly Cys Trp Leu Asp Asp Phe Asn Cys Tyr Asp Arg
545 550 555 560

Gln Glu Cys Val Ala Thr Glu Glu Asn Pro Gln Val Tyr Phe Cys Cys
565 570 575

Cys Glu Gly Asn Phe Cys Asn Glu Arg Phe Thr His Leu Pro Glu Ala
580 585 590

Gly Gly Pro Glu Val Thr Tyr Glu Pro Pro Pro Thr Ala Pro Thr
595 600 605

<210> SEQ ID NO 61
<211> LENGTH: 607
<212> TYPE: PRT
<213> ORGANISM: Artificial
<220> FEATURE:
<223> OTHER INFORMATION: A213 amino acid sequence

<400> SEQUENCE: 61

Leu Pro Ala Gln Val Ala Phe Thr Pro Tyr Ala Pro Glu Pro Gly Ser
1 5 10 15

Thr Cys Arg Leu Arg Glu Tyr Tyr Asp Gln Thr Ala Gln Met Cys Cys
20 25 30

Ser Lys Cys Ser Pro Gly Gln His Ala Lys Val Phe Cys Thr Lys Thr
35 40 45

Ser Asp Thr Val Cys Asp Ser Cys Glu Asp Ser Thr Tyr Thr Gln Leu
50 55 60

Trp Asn Trp Val Pro Glu Cys Leu Ser Cys Gly Ser Arg Cys Ser Ser
65 70 75 80

Asp Gln Val Glu Thr Gln Ala Cys Thr Arg Glu Gln Asn Arg Ile Cys
85 90 95

Thr Cys Arg Pro Gly Trp Tyr Cys Ala Leu Ser Lys Gln Glu Gly Cys
100 105 110

-continued

```
Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Glu Thr Arg Glu Cys Ile Tyr Tyr Asn Ala Asn Trp Glu Leu Glu
            500                 505                 510

Arg Thr Asn Gln Ser Gly Leu Glu Arg Cys Glu Gly Asp Gln Asp Lys
        515                 520                 525
```

```
Arg Leu His Cys Tyr Ala Ser Trp Arg Asn Ser Ser Gly Thr Ile Glu
    530                 535                 540

Leu Val Lys Lys Gly Cys Trp Leu Asp Asp Ile Asn Cys Tyr Asp Arg
545                 550                 555                 560

Gln Glu Cys Val Ala Thr Lys Glu Asn Pro Gln Val Tyr Phe Cys Cys
                565                 570                 575

Cys Glu Gly Asn Phe Cys Asn Glu Arg Phe Thr His Leu Pro Glu Ala
            580                 585                 590

Gly Gly Pro Glu Val Thr Tyr Glu Pro Pro Pro Thr Ala Pro Thr
        595                 600                 605


<210> SEQ ID NO 62
<211> LENGTH: 607
<212> TYPE: PRT
<213> ORGANISM: Artificial
<220> FEATURE:
<223> OTHER INFORMATION: A214 amino acid sequence

<400> SEQUENCE: 62

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285
```

```
Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Glu Thr Arg Glu Cys Ile Tyr Tyr Asn Ala Asn Trp Glu Leu Glu
            500                 505                 510

Arg Thr Asn Gln Ser Gly Leu Glu Arg Cys Tyr Gly Asp Lys Asp Lys
        515                 520                 525

Arg Arg His Cys Tyr Ala Ser Trp Arg Asn Ser Ser Gly Thr Ile Glu
    530                 535                 540

Leu Val Lys Lys Gly Cys Trp Leu Asp Asp Phe Asn Cys Tyr Asp Arg
545                 550                 555                 560

Gln Glu Cys Val Ala Thr Glu Glu Asn Pro Gln Val Tyr Phe Cys Cys
                565                 570                 575

Cys Glu Gly Asn Phe Cys Asn Glu Arg Phe Thr His Leu Pro Glu Ala
            580                 585                 590

Gly Gly Pro Glu Val Thr Tyr Glu Pro Pro Pro Thr Ala Pro Thr
        595                 600                 605


<210> SEQ ID NO 63
<211> LENGTH: 604
<212> TYPE: PRT
<213> ORGANISM: Artificial
<220> FEATURE:
<223> OTHER INFORMATION: A215 amino acid sequence

<400> SEQUENCE: 63

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45
```

```
Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
```

```
465                 470                 475                 480

Gly Lys Gly Gly Gly Gly Ser Gly Gly Gly Gly Ser Gly Gly Gly Gly
                485                 490                 495

Ser Glu Thr Arg Glu Cys Ile Tyr Tyr Asn Ala Asn Trp Glu Leu Glu
            500                 505                 510

Arg Thr Asn Gln Ser Gly Leu Glu Arg Cys Glu Gly Glu Gln Asp Lys
        515                 520                 525

Arg Leu His Cys Tyr Ala Ser Trp Arg Asn Ser Ser Gly Thr Ile Glu
    530                 535                 540

Leu Val Lys Lys Gly Cys Trp Asp Asp Asp Phe Asn Cys Tyr Asp Arg
545                 550                 555                 560

Gln Glu Cys Val Ala Thr Glu Glu Asn Pro Gln Val Tyr Phe Cys Cys
                565                 570                 575

Cys Glu Gly Asn Phe Cys Asn Glu Arg Phe Thr His Leu Pro Glu Ala
            580                 585                 590

Gly Gly Pro Glu Val Thr Tyr Glu Pro Pro Pro Thr
        595                 600


<210> SEQ ID NO 64
<211> LENGTH: 606
<212> TYPE: PRT
<213> ORGANISM: Artificial
<220> FEATURE:
<223> OTHER INFORMATION: A216 amino acid sequence

<400> SEQUENCE: 64

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
```

```
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Gly Ala Ile Leu Gly Arg Ser Glu Thr Gln Glu Cys Leu Phe Tyr
            500                 505                 510

Asn Ala Asn Trp Glu Leu Glu Arg Thr Asn Gln Thr Gly Val Glu Pro
        515                 520                 525

Cys Glu Gly Glu Lys Asp Lys Arg Leu His Cys Tyr Ala Thr Trp Arg
    530                 535                 540

Asn Ile Ser Gly Ser Ile Glu Ile Val Lys Lys Gly Cys Trp Leu Asp
545                 550                 555                 560

Asp Phe Asn Cys Tyr Asp Arg Thr Asp Cys Val Glu Thr Glu Glu Asn
                565                 570                 575

Pro Gln Val Tyr Phe Cys Cys Cys Glu Gly Asn Met Cys Asn Glu Lys
            580                 585                 590

Phe Ser Tyr Phe Pro Glu Met Glu Val Thr Gln Pro Thr Ser
        595                 600                 605


<210> SEQ ID NO 65
<211> LENGTH: 812
<212> TYPE: PRT
<213> ORGANISM: Artificial
<220> FEATURE:
<223> OTHER INFORMATION: A105 amino acid sequence
```

<400> SEQUENCE: 65

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415
```

```
Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Gly Asn Cys Trp Leu Arg Gln Ala Lys Asn Gly Arg Cys Gln Val
            500                 505                 510

Leu Tyr Lys Thr Glu Leu Ser Lys Glu Glu Cys Cys Ser Thr Gly Arg
        515                 520                 525

Leu Ser Thr Ser Trp Thr Glu Glu Asp Val Asn Asp Asn Thr Leu Phe
    530                 535                 540

Lys Trp Met Ile Phe Asn Gly Gly Ala Pro Asn Cys Ile Pro Cys Lys
545                 550                 555                 560

Glu Thr Cys Glu Asn Val Asp Cys Gly Pro Gly Gln Ser Cys Val Val
                565                 570                 575

Asp Gln Thr Gly Ser Pro Arg Cys Val Cys Ala Pro Asp Cys Ser Asn
            580                 585                 590

Ile Thr Trp Lys Gly Pro Val Cys Gly Leu Asp Gly Lys Thr Tyr Arg
        595                 600                 605

Asn Glu Cys Ala Leu Leu Lys Ala Arg Cys Lys Glu Gln Pro Glu Leu
    610                 615                 620

Glu Val Gln Tyr Gln Gly Arg Cys Lys Lys Thr Cys Arg Asp Val Phe
625                 630                 635                 640

Cys Pro Gly Ser Ser Thr Cys Val Val Asp Gln Thr Asn Asn Ala Tyr
                645                 650                 655

Cys Val Thr Cys Asn Arg Ile Cys Pro Glu Pro Ala Ser Ser Glu Gln
            660                 665                 670

Tyr Leu Cys Gly Asn Asp Gly Val Thr Tyr Ser Ser Ala Cys His Leu
        675                 680                 685

Arg Lys Ala Thr Cys Leu Leu Gly Arg Ser Ile Gly Leu Ala Tyr Glu
    690                 695                 700

Gly Lys Cys Ile Lys Ala Lys Ser Cys Glu Asp Ile Gln Cys Thr Gly
705                 710                 715                 720

Gly Lys Lys Cys Leu Trp Asp Phe Lys Val Gly Arg Gly Arg Cys Ser
                725                 730                 735

Leu Cys Asp Glu Leu Cys Pro Asp Ser Lys Ser Asp Glu Pro Val Cys
            740                 745                 750

Ala Ser Asp Asn Ala Thr Tyr Ala Ser Glu Cys Ala Met Lys Glu Ala
        755                 760                 765

Ala Cys Ser Ser Gly Val Leu Leu Glu Val Lys His Ser Gly Ser Cys
    770                 775                 780

Asn Ser Ile Ser Glu Asp Thr Glu Glu Glu Glu Glu Asp Glu Asp Gln
785                 790                 795                 800

Asp Tyr Ser Phe Pro Ile Ser Ser Ile Leu Glu Trp
                805                 810
```

<210> SEQ ID NO 66
<211> LENGTH: 812

<212> TYPE: PRT
<213> ORGANISM: Artificial
<220> FEATURE:
<223> OTHER INFORMATION: A217 amino acid sequence

<400> SEQUENCE: 66

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Gly Gly Gly Gly Ser
225                 230                 235                 240

Gly Gly Gly Gly Ser Gly Gly Gly Gly Ser Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380
```

```
Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Gly Asn Cys Trp Leu Arg Gln Ala Lys Asn Gly Arg Cys Gln Val
            500                 505                 510

Leu Tyr Lys Thr Glu Leu Ser Lys Glu Glu Cys Cys Ser Thr Gly Arg
        515                 520                 525

Leu Ser Thr Ser Trp Thr Glu Glu Asp Val Asn Asp Asn Thr Leu Phe
    530                 535                 540

Lys Trp Met Ile Phe Asn Gly Gly Ala Pro Asn Cys Ile Pro Cys Lys
545                 550                 555                 560

Glu Thr Cys Glu Asn Val Asp Cys Gly Pro Gly Lys Lys Cys Arg Met
                565                 570                 575

Asn Lys Lys Asn Lys Pro Arg Cys Val Cys Ala Pro Asp Cys Ser Asn
            580                 585                 590

Ile Thr Trp Lys Gly Pro Val Cys Gly Leu Asp Gly Lys Thr Tyr Arg
        595                 600                 605

Asn Glu Cys Ala Leu Leu Lys Ala Arg Cys Lys Glu Gln Pro Glu Leu
    610                 615                 620

Glu Val Gln Tyr Gln Gly Arg Cys Lys Lys Thr Cys Arg Asp Val Phe
625                 630                 635                 640

Cys Pro Gly Ser Ser Thr Cys Val Val Asp Gln Thr Asn Asn Ala Tyr
                645                 650                 655

Cys Val Thr Cys Asn Arg Ile Cys Pro Glu Pro Ala Ser Ser Glu Gln
            660                 665                 670

Tyr Leu Cys Gly Asn Asp Gly Val Thr Tyr Ser Ser Ala Cys His Leu
        675                 680                 685

Arg Lys Ala Thr Cys Leu Leu Gly Arg Ser Ile Gly Leu Ala Tyr Glu
    690                 695                 700

Gly Lys Cys Ile Lys Ala Lys Ser Cys Glu Asp Ile Gln Cys Thr Gly
705                 710                 715                 720

Gly Lys Lys Cys Leu Trp Asp Phe Lys Val Gly Arg Gly Arg Cys Ser
                725                 730                 735

Leu Cys Asp Glu Leu Cys Pro Asp Ser Lys Ser Asp Glu Pro Val Cys
            740                 745                 750

Ala Ser Asp Asn Ala Thr Tyr Ala Ser Glu Cys Ala Met Lys Glu Ala
        755                 760                 765

Ala Cys Ser Ser Gly Val Leu Leu Glu Val Lys His Ser Gly Ser Cys
    770                 775                 780

Asn Ser Ile Ser Glu Asp Thr Glu Glu Glu Glu Glu Asp Glu Asp Gln
785                 790                 795                 800

Asp Tyr Ser Phe Pro Ile Ser Ser Ile Leu Glu Trp
```

805 810

<210> SEQ ID NO 67
<211> LENGTH: 785
<212> TYPE: PRT
<213> ORGANISM: Artificial
<220> FEATURE:
<223> OTHER INFORMATION: A218 amino acid sequence

<400> SEQUENCE: 67

Leu Pro Ala Gln Val Ala Phe Thr Pro Tyr Ala Pro Glu Pro Gly Ser
1 5 10 15

Thr Cys Arg Leu Arg Glu Tyr Tyr Asp Gln Thr Ala Gln Met Cys Cys
20 25 30

Ser Lys Cys Ser Pro Gly Gln His Ala Lys Val Phe Cys Thr Lys Thr
35 40 45

Ser Asp Thr Val Cys Asp Ser Cys Glu Asp Ser Thr Tyr Thr Gln Leu
50 55 60

Trp Asn Trp Val Pro Glu Cys Leu Ser Cys Gly Ser Arg Cys Ser Ser
65 70 75 80

Asp Gln Val Glu Thr Gln Ala Cys Thr Arg Glu Gln Asn Arg Ile Cys
85 90 95

Thr Cys Arg Pro Gly Trp Tyr Cys Ala Leu Ser Lys Gln Glu Gly Cys
100 105 110

Arg Leu Cys Ala Pro Leu Arg Lys Cys Arg Pro Gly Phe Gly Val Ala
115 120 125

Arg Pro Gly Thr Glu Thr Ser Asp Val Val Cys Lys Pro Cys Ala Pro
130 135 140

Gly Thr Phe Ser Asn Thr Thr Ser Ser Thr Asp Ile Cys Arg Pro His
145 150 155 160

Gln Ile Cys Asn Val Val Ala Ile Pro Gly Asn Ala Ser Met Asp Ala
165 170 175

Val Cys Thr Ser Thr Ser Pro Thr Arg Ser Met Ala Pro Gly Ala Val
180 185 190

His Leu Pro Gln Pro Val Ser Thr Arg Ser Gln His Thr Gln Pro Thr
195 200 205

Pro Glu Pro Ser Thr Ala Pro Ser Thr Ser Phe Leu Leu Pro Met Gly
210 215 220

Pro Ser Pro Pro Ala Glu Gly Ser Thr Gly Asp Gly Gly Gly Gly Ser
225 230 235 240

Gly Gly Gly Gly Ser Gly Gly Gly Gly Ser Glu Pro Lys Ser Cys Asp
245 250 255

Lys Thr His Thr Cys Pro Pro Cys Pro Ala Pro Glu Leu Leu Gly Gly
260 265 270

Pro Ser Val Phe Leu Phe Pro Pro Lys Pro Lys Asp Thr Leu Met Ile
275 280 285

Ser Arg Thr Pro Glu Val Thr Cys Val Val Val Asp Val Ser His Glu
290 295 300

Asp Pro Glu Val Lys Phe Asn Trp Tyr Val Asp Gly Val Glu Val His
305 310 315 320

Asn Ala Lys Thr Lys Pro Arg Glu Glu Gln Tyr Asn Ser Thr Tyr Arg
325 330 335

Val Val Ser Val Leu Thr Val Leu His Gln Asp Trp Leu Asn Gly Lys
340 345 350

Glu Tyr Lys Cys Lys Val Ser Asn Lys Ala Leu Pro Ala Pro Ile Glu

```
        355                 360                 365

Lys Thr Ile Ser Lys Ala Lys Gly Gln Pro Arg Glu Pro Gln Val Tyr
    370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys Gly Gly Gly Gly Ser Gly Gly Gly Gly Ser Gly Gly Gly Gly
                485                 490                 495

Ser Gly Asn Cys Trp Leu Arg Gln Ala Lys Asn Gly Arg Cys Gln Val
            500                 505                 510

Leu Tyr Lys Thr Glu Leu Ser Lys Glu Glu Cys Cys Ser Thr Gly Arg
        515                 520                 525

Leu Ser Thr Ser Trp Thr Glu Glu Asp Val Asn Asp Asn Thr Leu Phe
    530                 535                 540

Lys Trp Met Ile Phe Asn Gly Gly Ala Pro Asn Cys Ile Pro Cys Lys
545                 550                 555                 560

Glu Thr Cys Glu Asn Val Asp Cys Gly Pro Gly Lys Lys Cys Arg Met
                565                 570                 575

Asn Lys Lys Asn Lys Pro Arg Cys Val Cys Ala Pro Asp Cys Ser Asn
            580                 585                 590

Ile Thr Trp Lys Gly Pro Val Cys Gly Leu Asp Gly Lys Thr Tyr Arg
        595                 600                 605

Asn Glu Cys Ala Leu Leu Lys Ala Arg Cys Lys Glu Gln Pro Glu Leu
    610                 615                 620

Glu Val Gln Tyr Gln Gly Arg Cys Lys Lys Thr Cys Arg Asp Val Phe
625                 630                 635                 640

Cys Pro Gly Ser Ser Thr Cys Val Val Asp Gln Thr Asn Asn Ala Tyr
                645                 650                 655

Cys Val Thr Cys Asn Arg Ile Cys Pro Glu Pro Ala Ser Ser Glu Gln
            660                 665                 670

Tyr Leu Cys Gly Asn Asp Gly Val Thr Tyr Ser Ser Ala Cys His Leu
        675                 680                 685

Arg Lys Ala Thr Cys Leu Leu Gly Arg Ser Ile Gly Leu Ala Tyr Glu
    690                 695                 700

Gly Lys Cys Ile Lys Ala Lys Ser Cys Glu Asp Ile Gln Cys Thr Gly
705                 710                 715                 720

Gly Lys Lys Cys Leu Trp Asp Phe Lys Val Gly Arg Gly Arg Cys Ser
                725                 730                 735

Leu Cys Asp Glu Leu Cys Pro Asp Ser Lys Ser Asp Glu Pro Val Cys
            740                 745                 750

Ala Ser Asp Asn Ala Thr Tyr Ala Ser Glu Cys Ala Met Lys Glu Ala
        755                 760                 765

Ala Cys Ser Ser Gly Val Leu Leu Glu Val Lys His Ser Gly Ser Cys
    770                 775                 780
```

Asn
785

<210> SEQ ID NO 68
<211> LENGTH: 699
<212> TYPE: PRT
<213> ORGANISM: Homo sapiens

<400> SEQUENCE: 68

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Leu Ser Trp Val Arg Gln Ala Pro Gly Gln Gly Leu Glu Trp Met
35 40 45

Gly Trp Ile Ile Pro Tyr Asn Gly Asn Thr Asn Ser Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Phe Cys
85 90 95

Ala Arg Asp Arg Asp Tyr Gly Val Asn Tyr Asp Ala Phe Asp Ile Trp
100 105 110

Gly Gln Gly Thr Met Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Lys Thr Tyr Thr Cys Asn Val Asp
195 200 205

His Lys Pro Ser Asn Thr Lys Val Asp Lys Arg Val Glu Ser Lys Tyr
210 215 220

Gly Pro Pro Cys Pro Ser Cys Pro Ala Pro Glu Phe Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Gly Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Gln Glu Glu Met Thr Lys Asn Gln Val Ser Leu Thr

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys Gly Gly Gly Gly Ser Gly Gly Gly Gly Ser Gly Gly Gly Gly Ser
    450                 455                 460

Leu Pro Ala Gln Val Ala Phe Thr Pro Tyr Ala Pro Glu Pro Gly Ser
465                 470                 475                 480

Thr Cys Arg Leu Arg Glu Tyr Tyr Asp Gln Thr Ala Gln Met Cys Cys
                485                 490                 495

Ser Lys Cys Ser Pro Gly Gln His Ala Lys Val Phe Cys Thr Lys Thr
            500                 505                 510

Ser Asp Thr Val Cys Asp Ser Cys Glu Asp Ser Thr Tyr Thr Gln Leu
        515                 520                 525

Trp Asn Trp Val Pro Glu Cys Leu Ser Cys Gly Ser Arg Cys Ser Ser
    530                 535                 540

Asp Gln Val Glu Thr Gln Ala Cys Thr Arg Glu Gln Asn Arg Ile Cys
545                 550                 555                 560

Thr Cys Arg Pro Gly Trp Tyr Cys Ala Leu Ser Lys Gln Glu Gly Cys
                565                 570                 575

Arg Leu Cys Ala Pro Leu Arg Lys Cys Arg Pro Gly Phe Gly Val Ala
            580                 585                 590

Arg Pro Gly Thr Glu Thr Ser Asp Val Val Cys Lys Pro Cys Ala Pro
        595                 600                 605

Gly Thr Phe Ser Asn Thr Thr Ser Ser Thr Asp Ile Cys Arg Pro His
    610                 615                 620

Gln Ile Cys Asn Val Val Ala Ile Pro Gly Asn Ala Ser Met Asp Ala
625                 630                 635                 640

Val Cys Thr Ser Thr Ser Pro Thr Arg Ser Met Ala Pro Gly Ala Val
                645                 650                 655

His Leu Pro Gln Pro Val Ser Thr Arg Ser Gln His Thr Gln Pro Thr
            660                 665                 670

Pro Glu Pro Ser Thr Ala Pro Ser Thr Ser Phe Leu Leu Pro Met Gly
        675                 680                 685

Pro Ser Pro Pro Ala Glu Gly Ser Thr Gly Asp
    690                 695


<210> SEQ ID NO 69
<211> LENGTH: 703
<212> TYPE: PRT
<213> ORGANISM: Homo sapiens

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30
```

```
Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys Gly Gly Gly Gly Ser Gly Gly Gly Gly Ser Gly
```

```
    450                 455                 460

Gly Gly Gly Ser Leu Pro Ala Gln Val Ala Phe Thr Pro Tyr Ala Pro
465                 470                 475                 480

Glu Pro Gly Ser Thr Cys Arg Leu Arg Glu Tyr Tyr Asp Gln Thr Ala
                485                 490                 495

Gln Met Cys Cys Ser Lys Cys Ser Pro Gly Gln His Ala Lys Val Phe
            500                 505                 510

Cys Thr Lys Thr Ser Asp Thr Val Cys Asp Ser Cys Glu Asp Ser Thr
        515                 520                 525

Tyr Thr Gln Leu Trp Asn Trp Val Pro Glu Cys Leu Ser Cys Gly Ser
    530                 535                 540

Arg Cys Ser Ser Asp Gln Val Glu Thr Gln Ala Cys Thr Arg Glu Gln
545                 550                 555                 560

Asn Arg Ile Cys Thr Cys Arg Pro Gly Trp Tyr Cys Ala Leu Ser Lys
                565                 570                 575

Gln Glu Gly Cys Arg Leu Cys Ala Pro Leu Arg Lys Cys Arg Pro Gly
            580                 585                 590

Phe Gly Val Ala Arg Pro Gly Thr Glu Thr Ser Asp Val Val Cys Lys
        595                 600                 605

Pro Cys Ala Pro Gly Thr Phe Ser Asn Thr Thr Ser Ser Thr Asp Ile
    610                 615                 620

Cys Arg Pro His Gln Ile Cys Asn Val Val Ala Ile Pro Gly Asn Ala
625                 630                 635                 640

Ser Met Asp Ala Val Cys Thr Ser Thr Ser Pro Thr Arg Ser Met Ala
                645                 650                 655

Pro Gly Ala Val His Leu Pro Gln Pro Val Ser Thr Arg Ser Gln His
            660                 665                 670

Thr Gln Pro Thr Pro Glu Pro Ser Thr Ala Pro Ser Thr Ser Phe Leu
        675                 680                 685

Leu Pro Met Gly Pro Ser Pro Pro Ala Glu Gly Ser Thr Gly Asp
    690                 695                 700


<210> SEQ ID NO 70
<211> LENGTH: 588
<212> TYPE: PRT
<213> ORGANISM: Artificial
<220> FEATURE:
<223> OTHER INFORMATION: A785 Heavy chain amino acid sequence

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Leu Ser Trp Val Arg Gln Ala Pro Gly Gln Gly Leu Glu Trp Met
        35                  40                  45

Gly Trp Ile Ile Pro Tyr Asn Gly Asn Thr Asn Ser Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Arg Asp Tyr Gly Val Asn Tyr Asp Ala Phe Asp Ile Trp
            100                 105                 110

Gly Gln Gly Thr Met Val Thr Val Ser Ser Gly Gly Gly Gly Ser Gly
```

```
        115                 120                 125

Gly Gly Gly Ser Gly Gly Gly Gly Ser Glu Val Gln Leu Val Glu Ser
    130                 135                 140

Gly Gly Gly Leu Val Gln Pro Gly Arg Ser Leu Arg Leu Ser Cys Ala
145                 150                 155                 160

Ala Ser Gly Phe Thr Phe Asp Asp Tyr Ala Met His Trp Val Arg Gln
                165                 170                 175

Ala Pro Gly Lys Gly Leu Glu Trp Val Ser Ala Ile Thr Trp Asn Ser
            180                 185                 190

Gly His Ile Asp Tyr Ala Asp Ser Val Glu Gly Arg Phe Thr Ile Ser
        195                 200                 205

Arg Asp Asn Ala Lys Asn Ser Leu Tyr Leu Gln Met Asn Ser Leu Arg
    210                 215                 220

Ala Glu Asp Thr Ala Val Tyr Tyr Cys Ala Lys Val Ser Tyr Leu Ser
225                 230                 235                 240

Thr Ala Ser Ser Leu Asp Tyr Trp Gly Gln Gly Thr Leu Val Thr Val
                245                 250                 255

Ser Ser Ala Ser Thr Lys Gly Pro Ser Val Phe Pro Leu Ala Pro Ser
            260                 265                 270

Ser Lys Ser Thr Ser Gly Gly Thr Ala Ala Leu Gly Cys Leu Val Lys
        275                 280                 285

Asp Tyr Phe Pro Glu Pro Val Thr Val Ser Trp Asn Ser Gly Ala Leu
    290                 295                 300

Thr Ser Gly Val His Thr Phe Pro Ala Val Leu Gln Ser Ser Gly Leu
305                 310                 315                 320

Tyr Ser Leu Ser Ser Val Val Thr Val Pro Ser Ser Ser Leu Gly Thr
                325                 330                 335

Gln Thr Tyr Ile Cys Asn Val Asn His Lys Pro Ser Asn Thr Lys Val
            340                 345                 350

Asp Lys Lys Val Glu Pro Lys Ser Cys Asp Lys Thr His Thr Cys Pro
        355                 360                 365

Pro Cys Pro Ala Pro Glu Leu Leu Gly Gly Pro Ser Val Phe Leu Phe
    370                 375                 380

Pro Pro Lys Pro Lys Asp Thr Leu Met Ile Ser Arg Thr Pro Glu Val
385                 390                 395                 400

Thr Cys Val Val Val Asp Val Ser His Glu Asp Pro Glu Val Lys Phe
                405                 410                 415

Asn Trp Tyr Val Asp Gly Val Glu Val His Asn Ala Lys Thr Lys Pro
            420                 425                 430

Arg Glu Glu Gln Tyr Asn Ser Thr Tyr Arg Val Val Ser Val Leu Thr
        435                 440                 445

Val Leu His Gln Asp Trp Leu Asn Gly Lys Glu Tyr Lys Cys Lys Val
    450                 455                 460

Ser Asn Lys Ala Leu Pro Ala Pro Ile Glu Lys Thr Ile Ser Lys Ala
465                 470                 475                 480

Lys Gly Gln Pro Arg Glu Pro Gln Val Tyr Thr Leu Pro Pro Ser Arg
                485                 490                 495

Asp Glu Leu Thr Lys Asn Gln Val Ser Leu Thr Cys Leu Val Lys Gly
            500                 505                 510

Phe Tyr Pro Ser Asp Ile Ala Val Glu Trp Glu Ser Asn Gly Gln Pro
        515                 520                 525

Glu Asn Asn Tyr Lys Thr Thr Pro Pro Val Leu Asp Ser Asp Gly Ser
    530                 535                 540
```

```
Phe Phe Leu Tyr Ser Lys Leu Thr Val Asp Lys Ser Arg Trp Gln Gln
545                 550                 555                 560

Gly Asn Val Phe Ser Cys Ser Val Met His Glu Ala Leu His Asn His
                565                 570                 575

Tyr Thr Gln Lys Ser Leu Ser Leu Ser Pro Gly Lys
            580                 585


<210> SEQ ID NO 71
<211> LENGTH: 335
<212> TYPE: PRT
<213> ORGANISM: Artificial
<220> FEATURE:
<223> OTHER INFORMATION: A785 Light chain amino acid sequence

<400> SEQUENCE: 71

Ser Tyr Glu Val Thr Gln Ala Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gly Gly Gly Ser Gly
            100                 105                 110

Gly Gly Gly Ser Gly Gly Gly Gly Ser Asp Ile Gln Met Thr Gln Ser
        115                 120                 125

Pro Ser Ser Leu Ser Ala Ser Val Gly Asp Arg Val Thr Ile Thr Cys
    130                 135                 140

Arg Ala Ser Gln Gly Ile Arg Asn Tyr Leu Ala Trp Tyr Gln Gln Lys
145                 150                 155                 160

Pro Gly Lys Ala Pro Lys Leu Leu Ile Tyr Ala Ala Ser Thr Leu Gln
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Arg Tyr Asn Arg Ala Pro Tyr Thr Phe Gly Gln Gly Thr Lys
    210                 215                 220

Val Glu Ile Lys Arg Thr Val Ala Ala Pro Ser Val Phe Ile Phe Pro
225                 230                 235                 240

Pro Ser Asp Glu Gln Leu Lys Ser Gly Thr Ala Ser Val Val Cys Leu
                245                 250                 255

Leu Asn Asn Phe Tyr Pro Arg Glu Ala Lys Val Gln Trp Lys Val Asp
            260                 265                 270

Asn Ala Leu Gln Ser Gly Asn Ser Gln Glu Ser Val Thr Glu Gln Asp
        275                 280                 285

Ser Lys Asp Ser Thr Tyr Ser Leu Ser Ser Thr Leu Thr Leu Ser Lys
    290                 295                 300

Ala Asp Tyr Glu Lys His Lys Val Tyr Ala Cys Glu Val Thr His Gln
305                 310                 315                 320
```

```
Gly Leu Ser Ser Pro Val Thr Lys Ser Phe Asn Arg Gly Glu Cys
                325                 330                 335


<210> SEQ ID NO 72
<211> LENGTH: 592
<212> TYPE: PRT
<213> ORGANISM: Artificial
<220> FEATURE:
<223> OTHER INFORMATION: A786 Heavy chain amino acid sequence

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Leu Tyr Thr Gly Gly Thr Ser Phe Asn Pro Ser Leu Lys
    50                  55                  60

Ser Arg Val Ser Met Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Ser Gly Ile Thr Phe Thr Gly Ile Ile Val Pro Gly Ser
            100                 105                 110

Phe Asp Ile Trp Gly Gln Gly Thr Met Val Thr Val Ser Ser Gly Gly
        115                 120                 125

Gly Gly Ser Gly Gly Gly Gly Ser Gly Gly Gly Gly Ser Glu Val Gln
    130                 135                 140

Leu Val Glu Ser Gly Gly Gly Leu Val Gln Pro Gly Arg Ser Leu Arg
145                 150                 155                 160

Leu Ser Cys Ala Ala Ser Gly Phe Thr Phe Asp Asp Tyr Ala Met His
                165                 170                 175

Trp Val Arg Gln Ala Pro Gly Lys Gly Leu Glu Trp Val Ser Ala Ile
            180                 185                 190

Thr Trp Asn Ser Gly His Ile Asp Tyr Ala Asp Ser Val Glu Gly Arg
        195                 200                 205

Phe Thr Ile Ser Arg Asp Asn Ala Lys Asn Ser Leu Tyr Leu Gln Met
    210                 215                 220

Asn Ser Leu Arg Ala Glu Asp Thr Ala Val Tyr Tyr Cys Ala Lys Val
225                 230                 235                 240

Ser Tyr Leu Ser Thr Ala Ser Ser Leu Asp Tyr Trp Gly Gln Gly Thr
                245                 250                 255

Leu Val Thr Val Ser Ser Ala Ser Thr Lys Gly Pro Ser Val Phe Pro
            260                 265                 270

Leu Ala Pro Ser Ser Lys Ser Thr Ser Gly Gly Thr Ala Ala Leu Gly
        275                 280                 285

Cys Leu Val Lys Asp Tyr Phe Pro Glu Pro Val Thr Val Ser Trp Asn
    290                 295                 300

Ser Gly Ala Leu Thr Ser Gly Val His Thr Phe Pro Ala Val Leu Gln
305                 310                 315                 320

Ser Ser Gly Leu Tyr Ser Leu Ser Ser Val Val Thr Val Pro Ser Ser
                325                 330                 335

Ser Leu Gly Thr Gln Thr Tyr Ile Cys Asn Val Asn His Lys Pro Ser
            340                 345                 350
```

```
Asn Thr Lys Val Asp Lys Lys Val Glu Pro Lys Ser Cys Asp Lys Thr
        355                 360                 365

His Thr Cys Pro Pro Cys Pro Ala Pro Glu Leu Leu Gly Gly Pro Ser
    370                 375                 380

Val Phe Leu Phe Pro Pro Lys Pro Lys Asp Thr Leu Met Ile Ser Arg
385                 390                 395                 400

Thr Pro Glu Val Thr Cys Val Val Val Asp Val Ser His Glu Asp Pro
                405                 410                 415

Glu Val Lys Phe Asn Trp Tyr Val Asp Gly Val Glu Val His Asn Ala
            420                 425                 430

Lys Thr Lys Pro Arg Glu Glu Gln Tyr Asn Ser Thr Tyr Arg Val Val
        435                 440                 445

Ser Val Leu Thr Val Leu His Gln Asp Trp Leu Asn Gly Lys Glu Tyr
    450                 455                 460

Lys Cys Lys Val Ser Asn Lys Ala Leu Pro Ala Pro Ile Glu Lys Thr
465                 470                 475                 480

Ile Ser Lys Ala Lys Gly Gln Pro Arg Glu Pro Gln Val Tyr Thr Leu
                485                 490                 495

Pro Pro Ser Arg Asp Glu Leu Thr Lys Asn Gln Val Ser Leu Thr Cys
            500                 505                 510

Leu Val Lys Gly Phe Tyr Pro Ser Asp Ile Ala Val Glu Trp Glu Ser
        515                 520                 525

Asn Gly Gln Pro Glu Asn Asn Tyr Lys Thr Thr Pro Pro Val Leu Asp
    530                 535                 540

Ser Asp Gly Ser Phe Phe Leu Tyr Ser Lys Leu Thr Val Asp Lys Ser
545                 550                 555                 560

Arg Trp Gln Gln Gly Asn Val Phe Ser Cys Ser Val Met His Glu Ala
                565                 570                 575

Leu His Asn His Tyr Thr Gln Lys Ser Leu Ser Leu Ser Pro Gly Lys
            580                 585                 590


<210> SEQ ID NO 73
<211> LENGTH: 337
<212> TYPE: PRT
<213> ORGANISM: Artificial
<220> FEATURE:
<223> OTHER INFORMATION: A786 Light chain amino acid sequence

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Gly Gly Gly
            100                 105                 110

Ser Gly Gly Gly Gly Ser Gly Gly Gly Gly Ser Asp Ile Gln Met Thr
        115                 120                 125
```

```
Gln Ser Pro Ser Ser Leu Ser Ala Ser Val Gly Asp Arg Val Thr Ile
    130                 135                 140

Thr Cys Arg Ala Ser Gln Gly Ile Arg Asn Tyr Leu Ala Trp Tyr Gln
145                 150                 155                 160

Gln Lys Pro Gly Lys Ala Pro Lys Leu Leu Ile Tyr Ala Ala Ser Thr
                165                 170                 175

Leu Gln Ser Gly Val Pro Ser Arg Phe Ser Gly Ser Gly Ser Gly Thr
            180                 185                 190

Asp Phe Thr Leu Thr Ile Ser Ser Leu Gln Pro Glu Asp Val Ala Thr
        195                 200                 205

Tyr Tyr Cys Gln Arg Tyr Asn Arg Ala Pro Tyr Thr Phe Gly Gln Gly
    210                 215                 220

Thr Lys Val Glu Ile Lys Arg Thr Val Ala Ala Pro Ser Val Phe Ile
225                 230                 235                 240

Phe Pro Pro Ser Asp Glu Gln Leu Lys Ser Gly Thr Ala Ser Val Val
                245                 250                 255

Cys Leu Leu Asn Asn Phe Tyr Pro Arg Glu Ala Lys Val Gln Trp Lys
            260                 265                 270

Val Asp Asn Ala Leu Gln Ser Gly Asn Ser Gln Glu Ser Val Thr Glu
        275                 280                 285

Gln Asp Ser Lys Asp Ser Thr Tyr Ser Leu Ser Ser Thr Leu Thr Leu
    290                 295                 300

Ser Lys Ala Asp Tyr Glu Lys His Lys Val Tyr Ala Cys Glu Val Thr
305                 310                 315                 320

His Gln Gly Leu Ser Ser Pro Val Thr Lys Ser Phe Asn Arg Gly Glu
                325                 330                 335

Cys


<210> SEQ ID NO 74
<211> LENGTH: 12
<212> TYPE: PRT
<213> ORGANISM: Artificial
<220> FEATURE:
<223> OTHER INFORMATION: Peptide linker sequence

<400> SEQUENCE: 74

Gly Gly Gly Ser Gly Gly Gly Ser Gly Gly Gly Ser
1               5                   10


<210> SEQ ID NO 75
<211> LENGTH: 4
<212> TYPE: PRT
<213> ORGANISM: Artificial
<220> FEATURE:
<223> OTHER INFORMATION: Peptide linker sequence

<400> SEQUENCE: 75

Gly Gly Gly Ser
1


<210> SEQ ID NO 76
<211> LENGTH: 13
<212> TYPE: PRT
<213> ORGANISM: Artificial
<220> FEATURE:
<223> OTHER INFORMATION: Peptide linker sequence

<400> SEQUENCE: 76

Gly Ser Ser Gly Gly Ser Gly Gly Ser Gly Gly Ser Gly
```

1 5 10

<210> SEQ ID NO 77
<211> LENGTH: 5
<212> TYPE: PRT
<213> ORGANISM: Artificial
<220> FEATURE:
<223> OTHER INFORMATION: Peptide linker sequence

<400> SEQUENCE: 77

Gly Ser Ser Gly Thr
1 5

<210> SEQ ID NO 78
<211> LENGTH: 14
<212> TYPE: PRT
<213> ORGANISM: Artificial
<220> FEATURE:
<223> OTHER INFORMATION: Peptide linker sequence

<400> SEQUENCE: 78

Gly Gly Gly Gly Ser Gly Gly Gly Gly Ser Gly Gly Gly Ser
1 5 10

<210> SEQ ID NO 79
<211> LENGTH: 17
<212> TYPE: PRT
<213> ORGANISM: Artificial
<220> FEATURE:
<223> OTHER INFORMATION: Peptide linker sequence

<400> SEQUENCE: 79

Ala Glu Ala Ala Ala Lys Glu Ala Ala Ala Lys Glu Ala Ala Ala Lys
1 5 10 15

Ala

<210> SEQ ID NO 80
<211> LENGTH: 20
<212> TYPE: PRT
<213> ORGANISM: Artificial
<220> FEATURE:
<223> OTHER INFORMATION: Peptide linker sequence

<400> SEQUENCE: 80

Gly Gly Gly Gly Ser Gly Gly Gly Gly Ser Gly Gly Gly Gly Ser Gly
1 5 10 15

Gly Gly Gly Ser
20

<210> SEQ ID NO 81
<211> LENGTH: 8
<212> TYPE: PRT
<213> ORGANISM: Artificial
<220> FEATURE:
<223> OTHER INFORMATION: Peptide linker sequence

<400> SEQUENCE: 81

Gly Gly Gly Ser Gly Gly Gly Ser
1 5

<210> SEQ ID NO 82
<211> LENGTH: 5
<212> TYPE: PRT
<213> ORGANISM: Artificial
<220> FEATURE:
<223> OTHER INFORMATION: Peptide linker sequence

<400> SEQUENCE: 82

Gly Ser Gly Ser Ser
1               5

<210> SEQ ID NO 83
<211> LENGTH: 4
<212> TYPE: PRT
<213> ORGANISM: Artificial
<220> FEATURE:
<223> OTHER INFORMATION: Peptide linker sequence

<400> SEQUENCE: 83

Gly Gly Ser Ser
1

<210> SEQ ID NO 84
<211> LENGTH: 5
<212> TYPE: PRT
<213> ORGANISM: Artificial
<220> FEATURE:
<223> OTHER INFORMATION: Peptide linker sequence

<400> SEQUENCE: 84

Gly Gly Gly Gly Ser
1               5

<210> SEQ ID NO 85
<211> LENGTH: 4
<212> TYPE: PRT
<213> ORGANISM: Artificial
<220> FEATURE:
<223> OTHER INFORMATION: Peptide linker sequence

<400> SEQUENCE: 85

Gly Gly Ser Gly
1

<210> SEQ ID NO 86
<211> LENGTH: 4
<212> TYPE: PRT
<213> ORGANISM: Artificial
<220> FEATURE:
<223> OTHER INFORMATION: Peptide linker sequence

<400> SEQUENCE: 86

Ser Gly Gly Gly
1

<210> SEQ ID NO 87
<211> LENGTH: 4
<212> TYPE: PRT
<213> ORGANISM: Artificial
<220> FEATURE:
<223> OTHER INFORMATION: Peptide linker sequence

<400> SEQUENCE: 87

Gly Ser Gly Ser
1

<210> SEQ ID NO 88
<211> LENGTH: 6
<212> TYPE: PRT
<213> ORGANISM: Artificial
<220> FEATURE:
<223> OTHER INFORMATION: Peptide linker sequence

```
<400> SEQUENCE: 88

Gly Ser Gly Ser Gly Ser
1               5


<210> SEQ ID NO 89
<211> LENGTH: 8
<212> TYPE: PRT
<213> ORGANISM: Artificial
<220> FEATURE:
<223> OTHER INFORMATION: Peptide linker sequence

<400> SEQUENCE: 89

Gly Ser Gly Ser Gly Ser Gly Ser
1               5


<210> SEQ ID NO 90
<211> LENGTH: 10
<212> TYPE: PRT
<213> ORGANISM: Artificial
<220> FEATURE:
<223> OTHER INFORMATION: Peptide linker sequence

<400> SEQUENCE: 90

Gly Ser Gly Ser Gly Ser Gly Ser Gly Ser
1               5                   10


<210> SEQ ID NO 91
<211> LENGTH: 12
<212> TYPE: PRT
<213> ORGANISM: Artificial
<220> FEATURE:
<223> OTHER INFORMATION: Peptide linker sequence

<400> SEQUENCE: 91

Gly Ser Gly Ser Gly Ser Gly Ser Gly Ser Gly Ser
1               5                   10


<210> SEQ ID NO 92
<211> LENGTH: 10
<212> TYPE: PRT
<213> ORGANISM: Artificial
<220> FEATURE:
<223> OTHER INFORMATION: Peptide linker sequence

<400> SEQUENCE: 92

Gly Gly Gly Gly Ser Gly Gly Gly Gly Ser
1               5                   10


<210> SEQ ID NO 93
<211> LENGTH: 15
<212> TYPE: PRT
<213> ORGANISM: Artificial
<220> FEATURE:
<223> OTHER INFORMATION: Peptide linker sequence

<400> SEQUENCE: 93

Gly Gly Gly Gly Ser Gly Gly Gly Gly Ser Gly Gly Gly Gly Ser
1               5                   10                  15
```

BIFUNCTIONAL ANTAGONISTS OF ACTIVIN AND TUMOR NECROSIS FACTOR ALPHA AND USES THEREOF

RELATED PATENT APPLICATIONS

This application is a U.S. National Stage Application pursuant to 35 U.S.C. § 371 of PCT/US2021/056272, filed Oct. 22, 2021, which claims benefit of U.S. Provisional Application No. 63/113,918, filed on Nov. 15, 2020, and which claims benefit of U.S. Provisional Application No. 63/104,765, filed on Oct. 23, 2020, each incorporated in its entirety by reference herein.

BACKGROUND ART

Tumor necrosis factor-α (TNF-α) mediates NF-kB signaling and plays an important role in various physiological and pathological processes, including cell proliferation, differentiation, apoptosis, and modulation of immune responses and induction of inflammation. TNF acts through two receptors, TNFR1 (TNF Receptor-1) and TNFR2 (TNF Receptor-2). TNF-α plays a pivotal role in inflammatory responses, programmed cell death and tissue necrosis. Increased TNF-α signaling has been implicated in a number of inflammatory diseases, including rheumatoid arthritis, ankylosing spondylitis, Crohn's disease and psoriasis, and anti-TNF therapies, such as adalimumab, infliximab and etanercept, have been shown to be highly effective in treating such inflammatory diseases. Elevated TNF-α levels and increased TNF-α signaling have also been implicated in the pathogenesis and progression of many other disease states including anemia, leukemia, multiple myeloma, fibrosis, hypertension, muscle wasting, bone loss, neurodegeneration, sepsis, fibrosis, pain, chronic kidney disease, liver disease, and heart failure.

As a subset of TGF-β superfamily, Activins, including Activin A, Activin B and Activin AB, and Activin-related proteins, including Myostatin (GDF-8) and GDF-11, mediate Smad2/3 signaling through binding and activation of their high-affinity receptors ActRIIA and ActRIIB on the cell surface. The Activins and related proteins play a critical role in the regulation of a wide range of biology activities, including mesoderm induction, cell differentiation, myogenesis, bone remodeling, hematopoiesis, fibrogenesis, and reproductive physiology. Follistatin (FST), a secreted glycoprotein, binds to the Activins and Activin-related ligands to negatively control their signaling activities. Overexpression of Activins and related ligands and increased Smad2/3 signaling have been implicated in pathogenesis and progression of many grievous conditions, such as cancer, anemia, bone metastasis, bone fragility, facture, muscle wasting disorders, cachexia, pulmonary hypertension, fibrosis, pain, insulin resistance, chronic kidney disease, liver disease, myocardial infarction and heart failure.

Mounting evidence indicates that many complex disorders involve parallel activation of TNF-α mediated NF-kB signaling pathway and Activin mediated Smad2/3 signaling pathway, whose activities promote pathogenesis and progression. Examples of such complex disorders include certain hematological disorders such as refractory anemia and myelodysplastic syndromes, cardiovascular diseases such as pulmonary hypertension and congestive heart failure, bone disorders such as bone metastasis and fracture, organ failures such as kidney, liver or myelo failure, and fibrotic diseases such as non-alcoholic steatohepatitis, cirrhosis and lung fibrosis, and pain such as nociceptive or neuropathic pain.

Current treatment options for these complex disorders are limited. Due to the involvement of more than one disease signaling mechanisms in these disorders, currently available therapies that were designed to target a single disease mechanism typically have poor efficacy and low response rate. Because TNF-α-NF-kB signaling pathway and Activin-Smad2/3 signaling pathway are both critically involved in disease pathogenesis and progression, it is clearly of importance to develop novel bifunctional antagonists capable of inhibiting the two disease signaling pathways in parallel.

DISCLOSURE OF THE INVENTION

In one aspect, the present invention provides novel polypeptide-based bifunctional antagonist molecules specifically designed to simultaneously neutralize TNF-α signaling and Activin signaling in a potent manner. In various embodiments, the bifunctional antagonist molecule is designed as depicted in FIG. 1. In various embodiments, the bifunctional antagonist molecule is designed as depicted in FIG. 2. In various embodiments, the bifunctional antagonist molecule is designed as depicted in FIG. 3.

In various embodiments, the bifunctional antagonist molecule is a bifunctional molecule comprising a first antigen-binding molecule that specifically binds to TNF-α ligand ("TNF-Binding Polypeptide") and a second antigen-binding molecule that specifically binds to Activin or Activin-related ligand ("Activin-Binding Polypeptide"). In various embodiments, the "TNF-binding polypeptide" is selected from the group consisting of an anti-TNF antibody, a fragment of anti-TNF antibody, wild-type TNFR1 and TNFR2 extracellular domains (ECDs), modified TNFR1 and TNFR2 extracellular domains, and a phage display-derived polypeptide targeting TNF-α, and the "Activin-binding polypeptide" is selected from any polypeptide that is capable binding Activin (i.e., Activin A, Activin B or Activin AB) and/or Activin-related ligand (i.e., GDF8 or GDF11), which includes, but is not limited to, an anti-Activin antibody (including anti-Activin A antibody and anti-Activin B antibody), a fragment of anti-Activin antibody, wild-type Activin Type 2A Receptor (ActRIIA) or Activin Type 2B Receptor (ActRIIB) extracellular domains (ECDs), modified ActRIIA and ActRIIB extracellular domains, wild-type and modified native Activin-binding proteins such as follistatin, follistatin-like protein and propeptide, and a phage display-derived polypeptide targeting Activin or Activin-related ligand.

In various embodiments, the bifunctional molecule comprises an isolated antibody, or antigen-binding fragment thereof, that specifically binds to TNF-α and an isolated antibody, or antigen-binding fragment thereof, that specifically binds to Activin or Activin-related ligand. In various embodiments, the isolated antibody or antigen-binding fragment thereof is selected from the group consisting of monoclonal Abs (mAbs), polyclonal Abs, Ab fragments (e.g., Fab, Fab', F(ab')2, Fv, Fc, etc.), chimeric Abs, mini-Abs or domain Abs (dAbs), dual specific Abs, bispecific Abs, heteroconjugate Abs, single chain Abs (SCA), single chain variable region fragments (ScFv), humanized Abs, fully human Abs, and any other modified configuration of the immunoglobulin (Ig) molecule that comprises an antigen recognition site of the required specificity. In various embodiments, the bifunctional molecule comprises an isolated antibody or antigen-binding fragment thereof selected from the group consisting of a fully human, humanized and chimeric antibody.

In various embodiments, the first antigen-binding molecule specifically binds a TNF ligand comprising an amino acid sequence set forth in SEQ ID NO: 1. In various embodiments, the first antigen-binding molecule specifically binds a TNF ligand comprising an amino acid sequence set forth in SEQ ID NO: 2. In various embodiments, the first antigen-binding molecule specifically binds a TNF ligand comprising an amino acid sequence set forth in SEQ ID NO: 3. In various embodiments, the first antigen-binding molecule specifically binds a TNF ligand comprising an amino acid sequence set forth in SEQ ID NO: 4. In various embodiments, the first antigen-binding molecule specifically binds a TNF ligand comprising an amino acid sequence set forth in SEQ ID NO: 5.

In various embodiments, the second antigen-binding molecule specifically binds an Activin or Activin-related ligand comprising an amino acid sequence set forth in SEQ ID NO: 6. In various embodiments, the second antigen-binding molecule specifically binds an Activin or Activin-related ligand comprising an amino acid sequence set forth in SEQ ID NO: 7. In various embodiments, the second antigen-binding molecule specifically binds an Activin or Activin-related ligand comprising an amino acid sequence set forth in SEQ ID NO: 8. In various embodiments, the second antigen-binding molecule specifically binds an Activin or Activin-related ligand comprising an amino acid sequence set forth in SEQ ID NO: 9. In various embodiments, the second antigen-binding molecule specifically binds an Activin or Activin-related ligand comprising an amino acid sequence set forth in SEQ ID NO: 10. In various embodiments, the second antigen-binding molecule specifically binds an Activin or Activin-related ligand comprising an amino acid sequence set forth in SEQ ID NO: 11. In various embodiments, the second antigen-binding molecule specifically binds an Activin or Activin-related ligand comprising an amino acid sequence set forth in SEQ ID NO: 12. In various embodiments, the second antigen-binding molecule specifically binds an Activin or Activin-related ligand comprising an amino acid sequence set forth in SEQ ID NO: 13. In various embodiments, the second antigen-binding molecule specifically binds an Activin or Activin-related ligand comprising an amino acid sequence set forth in SEQ ID NO: 14.

In various embodiments, the first antigen-binding molecule that specifically binds to TNF-α ligand is an isolated antibody selected from the group consisting of an antibody comprising the heavy chain amino acid sequence set forth in SEQ ID NO: 15; an antibody comprising the light chain amino acid sequence set forth in SEQ ID NO: 17; an antibody comprising the heavy chain amino acid sequence set forth in SEQ ID NO: 15 and the light chain amino acid sequence set forth in SEQ ID NO: 17; an antibody comprising the heavy chain variable region amino acid sequence set forth in SEQ ID NO: 16; an antibody comprising the light chain variable region amino acid sequence set forth in SEQ ID NO: 18; and an antibody comprising the heavy chain variable region amino acid sequence set forth in SEQ ID NO: 16 and the light chain variable region amino acid sequence set forth in SEQ ID NO: 18.

In various embodiments, the first antigen-binding molecule that specifically binds to TNF-α ligand is an isolated antibody selected from the group consisting of an antibody comprising the heavy chain amino acid sequence set forth in SEQ ID NO: 19; an antibody comprising the light chain amino acid sequence set forth in SEQ ID NO: 21; an antibody comprising the heavy chain amino acid sequence set forth in SEQ ID NO: 19 and the light chain amino acid sequence set forth in SEQ ID NO: 21; an antibody comprising the heavy chain variable region amino acid sequence set forth in SEQ ID NO: 20; an antibody comprising the light chain variable region amino acid sequence set forth in SEQ ID NO: 22; and an antibody comprising the heavy chain variable region amino acid sequence set forth in SEQ ID NO: 20 and the light chain variable region amino acid sequence set forth in SEQ ID NO: 22.

In various embodiments, the first antigen-binding molecule that specifically binds to TNF-α ligand is an isolated antibody selected from the group consisting of an antibody comprising the heavy chain amino acid sequence set forth in SEQ ID NO: 23; an antibody comprising the light chain amino acid sequence set forth in SEQ ID NO: 25; an antibody comprising the heavy chain amino acid sequence set forth in SEQ ID NO: 23 and the light chain amino acid sequence set forth in SEQ ID NO: 25; an antibody comprising the heavy chain variable region amino acid sequence set forth in SEQ ID NO: 24; an antibody comprising the light chain variable region amino acid sequence set forth in SEQ ID NO: 26; and an antibody comprising the heavy chain variable region amino acid sequence set forth in SEQ ID NO: 24 and the light chain variable region amino acid sequence set forth in SEQ ID NO: 26.

In various embodiments, the first antigen-binding molecule that specifically binds to TNF-α ligand is an isolated antibody selected from the group consisting of an antibody comprising the heavy chain amino acid sequence set forth in SEQ ID NO: 27; an antibody comprising the light chain amino acid sequence set forth in SEQ ID NO: 29; an antibody comprising the heavy chain amino acid sequence set forth in SEQ ID NO: 27 and the light chain amino acid sequence set forth in SEQ ID NO: 29; an antibody comprising the heavy chain variable region amino acid sequence set forth in SEQ ID NO: 28; an antibody comprising the light chain variable region amino acid sequence set forth in SEQ ID NO: 30; and an antibody comprising the heavy chain variable region amino acid sequence set forth in SEQ ID NO: 28 and the light chain variable region amino acid sequence set forth in SEQ ID NO: 30.

In various embodiments, the second antigen-binding molecule that specifically binds to Activin or Activin-related ligand is an isolated antibody selected from the group consisting of an antibody comprising the heavy chain amino acid sequence set forth in SEQ ID NO: 31; an antibody comprising the light chain amino acid sequence set forth in SEQ ID NO: 33; an antibody comprising the heavy chain amino acid sequence set forth in SEQ ID NO: 31 and the light chain amino acid sequence set forth in SEQ ID NO: 33; an antibody comprising the heavy chain variable region amino acid sequence set forth in SEQ ID NO: 32; an antibody comprising the light chain variable region amino acid sequence set forth in SEQ ID NO: 34; and an antibody comprising the heavy chain variable region amino acid sequence set forth in SEQ ID NO: 32 and the light chain variable region amino acid sequence set forth in SEQ ID NO: 34.

In various embodiments, the second antigen-binding molecule that specifically binds to Activin or Activin-related ligand is an isolated antibody selected from the group consisting of an antibody comprising the heavy chain amino acid sequence set forth in SEQ ID NO: 35; an antibody comprising the light chain amino acid sequence set forth in SEQ ID NO: 37; an antibody comprising the heavy chain amino acid sequence set forth in SEQ ID NO: 35 and the light chain amino acid sequence set forth in SEQ ID NO: 37; an antibody comprising the heavy chain variable region amino acid sequence set forth in SEQ ID NO: 36; an antibody comprising the light chain variable region amino acid sequence set forth in SEQ ID NO: 38; and an antibody comprising the heavy chain variable region amino acid sequence set forth in SEQ ID NO: 36 and the light chain variable region amino acid sequence set forth in SEQ ID NO: 38.

In various embodiments, the bifunctional antagonist molecule is a bifunctional molecule comprising a first antigen-binding molecule that specifically binds to TNF-α ligand and a second antigen-binding molecule that specifically binds to Activin or Activin-related ligand, wherein the TNF-α ligand binding molecule is selected from the group of polypeptides comprising the amino acid sequence set forth in SEQ ID NOs: 1-5 and 15-30, and the Activin or Activin-related ligand binding molecule is selected from the group of polypeptides comprising the amino acid sequence set forth in SEQ ID NOs: 6-14 and 31-38.

In various embodiments, the bifunctional antagonist molecule is a bifunctional molecule comprising a first antigen-binding molecule that specifically binds to TNF-α ligand and a second antigen-binding molecule that specifically binds to Activin or Activin-related ligand, wherein the bifunctional molecule is selected from the group consisting of: a bifunctional molecule comprising the heavy chain amino acid sequence set forth in SEQ ID NO: 39 and the light chain amino acid sequence set forth in SEQ ID NO: 17; a bifunctional molecule comprising the heavy chain amino acid sequence set forth in SEQ ID NO: 40 and the light chain amino acid sequence set forth in SEQ ID NO: 17; a bifunctional molecule comprising the heavy chain amino acid sequence set forth in SEQ ID NO: 41 and the light chain amino acid sequence set forth in SEQ ID NO: 17; a bifunctional molecule comprising the heavy chain amino acid sequence set forth in SEQ ID NO: 42 and the light chain amino acid sequence set forth in SEQ ID NO: 17; a bifunctional molecule comprising the heavy chain amino acid sequence set forth in SEQ ID NO: 43 and the light chain amino acid sequence set forth in SEQ ID NO: 17; a bifunctional molecule comprising the heavy chain amino acid sequence set forth in SEQ ID NO: 44 and the light chain amino acid sequence set forth in SEQ ID NO: 17; a bifunctional molecule comprising the heavy chain amino acid sequence set forth in SEQ ID NO: 45 and the light chain amino acid sequence set forth in SEQ ID NO: 17; a bifunctional molecule comprising the heavy chain amino acid sequence set forth in SEQ ID NO: 46 and the light chain amino acid sequence set forth in SEQ ID NO: 17; a bifunctional molecule comprising the heavy chain amino acid sequence set forth in SEQ ID NO: 47 and the light chain amino acid sequence set forth in SEQ ID NO: 17; a bifunctional molecule comprising the heavy chain amino acid sequence set forth in SEQ ID NO: 31 and the light chain amino acid sequence set forth in SEQ ID NO: 33; a bifunctional molecule comprising the heavy chain amino acid sequence set forth in SEQ ID NO: 35 and the light chain amino acid sequence set forth in SEQ ID NO: 37; a bifunctional molecule comprising the heavy chain amino acid sequence set forth in SEQ ID NO: 57 and the light chain amino acid sequence set forth in SEQ ID NO: 33; a bifunctional molecule comprising the heavy chain amino acid sequence set forth in SEQ ID NO: 58 and the light chain amino acid sequence set forth in SEQ ID NO: 37; a bifunctional molecule comprising the heavy chain amino acid sequence set forth in SEQ ID NO: 68 and the light chain amino acid sequence set forth in SEQ ID NO: 33; a bifunctional molecule comprising the heavy chain amino acid sequence set forth in SEQ ID NO: 69 and the light chain amino acid sequence set forth in SEQ ID NO: 37; a bifunctional molecule comprising the heavy chain amino acid sequence set forth in SEQ ID NO: 70 and the light chain amino acid sequence set forth in SEQ ID NO: 71; and a bifunctional molecule comprising the heavy chain amino acid sequence set forth in SEQ ID NO: 72 and the light chain amino acid sequence set forth in SEQ ID NO: 73.

In various embodiments, the bifunctional antagonist molecule is a bifunctional molecule comprising a first antigen-binding molecule that specifically binds to TNF-α ligand and a second antigen-binding molecule that specifically binds to Activin or Activin-related ligand, wherein the bifunctional molecule is selected from the group consisting of: a bifunctional molecule comprising the amino acid sequence set forth in SEQ ID NO: 48; a bifunctional molecule comprising the amino acid sequence set forth in SEQ ID NO: 49; a bifunctional molecule comprising the amino acid sequence set forth in SEQ ID NO: 50; a bifunctional molecule comprising the amino acid sequence set forth in SEQ ID NO: 51; a bifunctional molecule comprising the amino acid sequence set forth in SEQ ID NO: 52; a bifunctional molecule comprising the amino acid sequence set forth in SEQ ID NO: 53; a bifunctional molecule comprising the amino acid sequence set forth in SEQ ID NO: 54; a bifunctional molecule comprising the amino acid sequence set forth in SEQ ID NO: 55; a bifunctional molecule comprising the amino acid sequence set forth in SEQ ID NO: 56; a bifunctional molecule comprising the amino acid sequence set forth in SEQ ID NO: 59; a bifunctional molecule comprising the amino acid sequence set forth in SEQ ID NO: 60; a bifunctional molecule comprising the amino acid sequence set forth in SEQ ID NO: 61; a bifunctional molecule comprising the amino acid sequence set forth in SEQ ID NO: 62; a bifunctional molecule comprising the amino acid sequence set forth in SEQ ID NO: 63; a bifunctional molecule comprising the amino acid sequence set forth in SEQ ID NO: 64; a bifunctional molecule comprising the amino acid sequence set forth in SEQ ID NO: 65; a bifunctional molecule comprising the amino acid sequence set forth in SEQ ID NO: 66; and a bifunctional molecule comprising the amino acid sequence set forth in SEQ ID NO: 67.

In another aspect, the present disclosure provides isolated nucleic acid molecules comprising a polynucleotide encoding a bifunctional antagonist molecule of the present disclosure. In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In another aspect, the present disclosure provides vectors comprising the nucleic acids described herein. In various embodiments, the vector is an expression vector. In another aspect, the present disclosure provides isolated cells comprising the nucleic acids of the disclosure. In various embodiments, the cell is a host cell comprising the expression vector of the disclosure. In another aspect, methods of making the bifunctional antagonist molecules are provided by culturing the host cells under conditions promoting expression of the proteins or polypeptides.

In another aspect, provided is a method for producing a bifunctional antagonist molecule comprising a first antigen-binding molecule that specifically binds to TNF-α and a second antigen-binding molecule that specifically binds to Activin as described herein, comprising the steps of a) transforming a host cell with vectors comprising polynucleotides encoding said bifunctional antagonist molecule, b) culturing the host cell according under conditions suitable for the expression of the bifunctional antagonist molecule and c) recovering the bifunctional antagonist molecule from the culture. The invention also encompasses a bifunctional antagonist molecule produced by the method of the invention.

In another aspect, the present disclosure provides a pharmaceutical composition comprising the isolated bifunctional antagonist molecules in admixture with a pharmaceutically acceptable carrier.

In another aspect, the present disclosure provides a method of treating or preventing various complex disease conditions whose pathogenesis involve the activation of both TNF-α-mediated NF-κB signaling pathway and Activin-mediated Smad2/3 signaling pathway, such as anemia of inflammation, pulmonary arterial hypertension, muscular dystrophy, and organ fibrosis.

In various embodiments, the novel bifunctional antagonist molecules of the present invention may have broad applications for the treatment of various disorders which include, but are not limited to, the following conditions: blood disorders: ineffective erythropoiesis, anemia, pancytopenia, myelodysplastic syndromes; fibrotic diseases: NASH, liver fibrosis, pulmonary fibrosis, renal fibrosis, polycystic kidney disease, cardiac fibrosis, muscle fibrosis, myelo fibrosis, skin fibrosis, tendon fibrosis, fibrosis of the hand, and fibrosis of the eye; Cancer: multiple myeloma, acute myeloid leukemia, melanoma, sarcoma, lung cancer, esophageal cancer, pancreatic cancer, colorectal cancer, liver cancer, head and neck cancer, endometrial cancer, ovarian cancer, and breast cancer; Cancer treatment in combination with checkpoint inhibitors such as anti-PD1, anti-PDL1 and anti-CTL4 antibodies; Neuromuscular diseases: muscular dystrophy, spinal muscular atrophy, spinal cord injury, stroke; Pain: nociceptive pain, neuropathic pain; Wasting disorders: sarcopenia, cancer cachexia, anorexia nervosa; Bone disorders: bone metastasis, bone fragility, fracture, osteopenia, osteoporosis; Cardiovascular diseases: pulmonary arterial hypertension, myocardial infarction, heart failure; Metabolic disorders: insulin resistance, diabetic nephropathy, chronic kidney disease; Inflammatory diseases: rheumatoid arthritis, inflammatory bowel disease; Infections: SARS-CoV, cytokine storm syndrome, sepsis; and Trauma: burn injury.

In another aspect, the disclosure provides uses of the bifunctional antagonist molecules for making a medicament for the treatment of any disorder or condition as described herein.

BRIEF DESCRIPTION OF THE FIGURES

Figure 1:
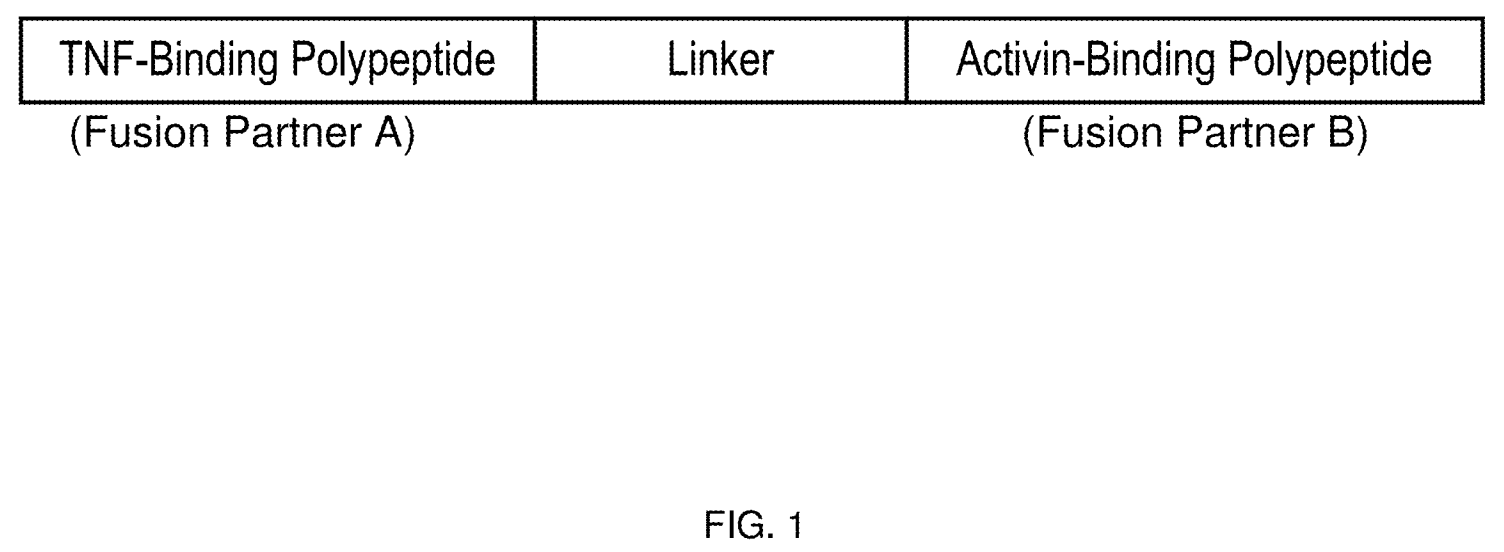

FIG. 1 depicts a representative bifunctional antagonist molecule of the present invention. The "TNF-binding polypeptide", as illustrated in this schematic, refers to any polypeptide that is capable binding TNF-α, which includes, but is not limited to, an anti-TNF antibody, a fragment of anti-TNF antibody, wild-type TNFR1 and TNFR2 extracellular domains (ECDs), modified TNFR1 and TNFR2 extracellular domains, and phage display-derived polypeptide targeting TNF-α. The "Activin-binding polypeptide", as illustrated in this schematic, refers to any polypeptide that is capable binding Activin (i.e., Activin A, Activin B or Activin AB) and/or Activin-related ligand (i.e., GDF8 or GDF11), which includes, but is not limited to, an anti-Activin antibody (including anti-Activin A antibody and anti-Activin B antibody), a fragment of anti-Activin antibody, wild-type Activin Type 2A Receptor (ActRIIA) or Activin Type 2B Receptor (ActRIIB) extracellular domains (ECDs), modified ActRIIA and ActRIIB extracellular domains, wild-type and modified native Activin-binding proteins such as follistatin, follistatin-like protein and propeptide, and phage display-derived polypeptide targeting Activin or Activin-related ligand. The "Linker", as shown in this schematic, refers to various methods for fusing different polypeptide fusion partners to generate bispecific and multispecific molecules, which includes, but not limited to, the use of any peptide linker or chemical linker.

MODE(S) FOR CARRYING OUT THE DISCLOSURE

Definitions

Figure 2:
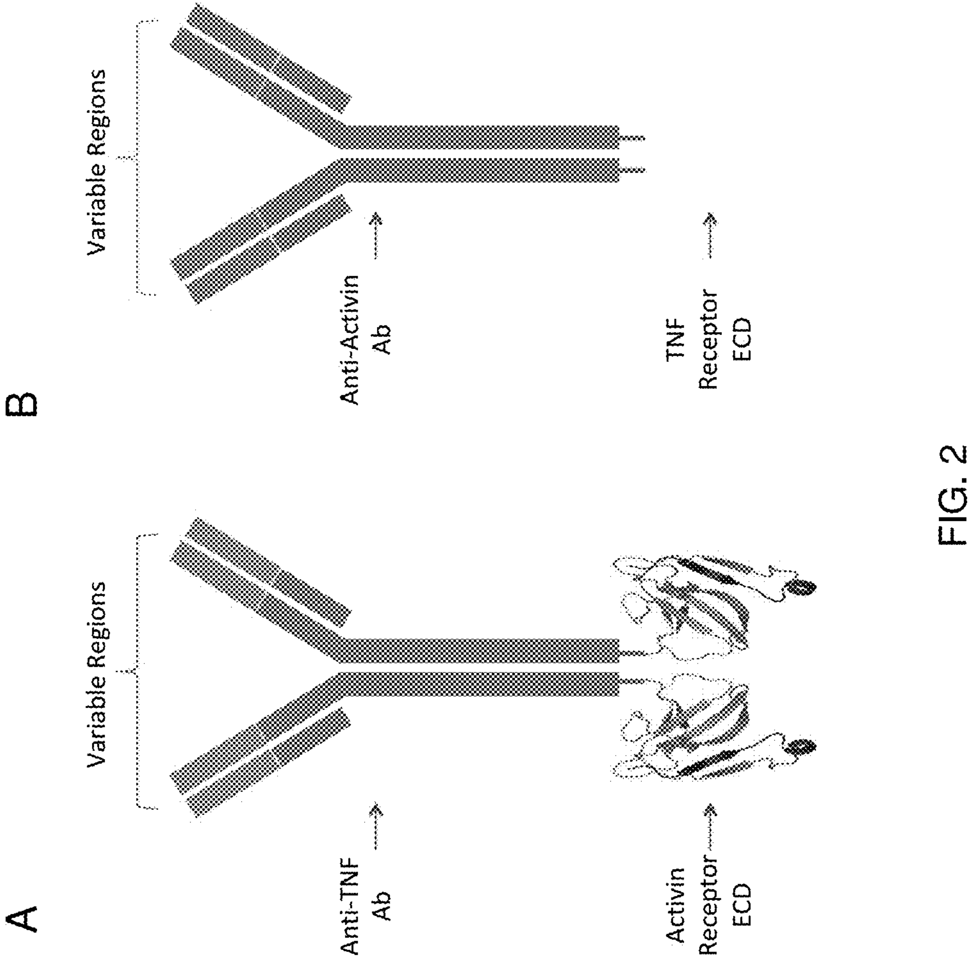
FIG. 2 depicts two representative bifunctional antagonist molecules of the present invention wherein: (A) the TNF-α-binding polypeptide is an anti-TNF-α antibody and the Activin-binding polypeptide is an Activin Receptor ECD attached via a linker to the heavy chain CH3 of the anti-TNF-α antibody; or (B) the Activin-binding polypeptide is an anti-Activin antibody and the TNF-α-binding polypeptide is a TNF Receptor ECD attached via a linker to the heavy chain CH3 of the anti-Activin antibody. In alternative embodiments, the Activin Receptor ECD (or TNF Receptor ECD) is attached to the anti-TNF-α antibody (or anti-Activin antibody) via a linker at the heavy chain variable region (VH) of the antibody. In alternative embodiments, the Activin Receptor ECD (or TNF Receptor ECD) is attached to the anti-TNF-α antibody (or anti-Activin antibody) via a linker at the light chain variable region (VL) of the antibody. In alternative embodiments, the Activin Receptor ECD (or TNF Receptor ECD) is attached to the anti-TNF-α antibody (or anti-Activin antibody) via a linker at an internal site rather than at the heavy chain CH3, VL, or VH sites of the antibody.
Figure 3:
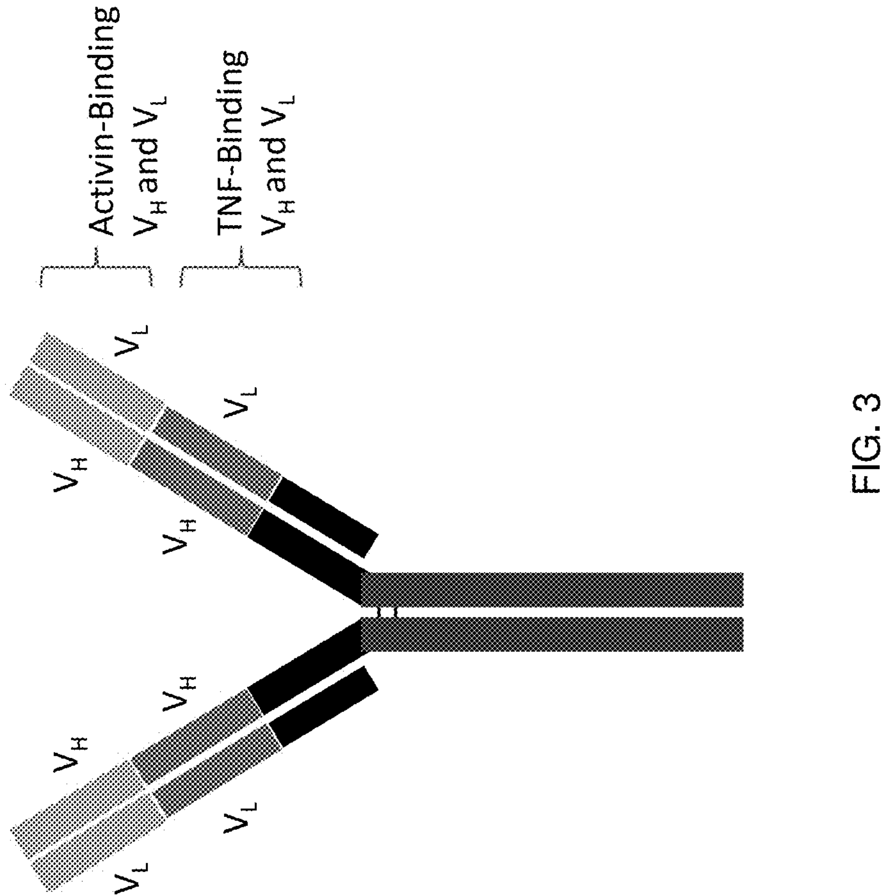
FIG. 3 depicts a representative bifunctional antagonist molecule of the present invention in the form of a bispecific antibody, which comprises (A) the variable regions (VH and VL) derived from an anti-activin A antibody and (B) the variable regions (VH and VL) of an anti-TNF antibody. Note that although the bispecific antibody illustrated in FIG. 3 is shown in one specific configuration, bispecific antibodies comprising variable regions from both anti-activin A and anti-TNF antibodies can be constructed by those that are skilled in the art in a wide variety of configurations.

The terms "polypeptide", "peptide" and "protein" are used interchangeably herein to refer to a polymer of amino acid residues. In various embodiments, "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond Polypeptides of the disclosure include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (5) confer or modify other physicochemical or functional properties.

An amino acid "substitution" as used herein refers to the replacement in a polypeptide of one amino acid at a particular position in a parent polypeptide sequence with a different amino acid. Amino acid substitutions can be generated using genetic or chemical methods well known in the art. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" refers to the substitution in a polypeptide of an amino acid with a functionally similar amino acid. The following six groups each contain amino acids that are conservative substitutions for one another:

1) Alanine (A), Serine (S), and Threonine (T)
2) Aspartic acid (D) and Glutamic acid (E)
3) Asparagine (N) and Glutamine (Q)
4) Arginine (R) and Lysine (K)
5) Isoleucine (I), Leucine (L), Methionine (M), and Valine (V)
6) Phenylalanine (F), Tyrosine (Y), and Tryptophan (W)

A "non-conservative amino acid substitution" refers to the substitution of a member of one of these classes for a member from another class. In making such changes, according to various embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in various embodiments, the substitution of amino acids whose hydropathic indices are within ±2 is included. In various embodiments, those that are within ±1 are included, and in various embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In various embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in various embodiments, the substitution of amino acids whose hydrophilicity values are within ±2 is included, in various embodiments, those that are within ±1 are included, and in various embodiments, those within ±0.5 are included.

Exemplary amino acid substitutions are set forth in Table 1.

TABLE 1

| Original Residues | Exemplary Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptides as set forth herein using well-known techniques. In various embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a polypeptide that correspond to amino acid residues important for activity or structure in similar polypeptides. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three-dimensional structure. In various embodiments, one skilled in the art may choose to not make radical changes to amino acid residues predicted to be on the surface of the polypeptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "polypeptide fragment" and "truncated polypeptide" as used herein refers to a polypeptide that has an amino-terminal and/or carboxy-terminal deletion as compared to a corresponding full-length protein. In various embodiments, fragments can be, e.g., at least 5, at least 10, at least 25, at least 50, at least 100, at least 150, at least 200, at least 250, at least 300, at least 350, at least 400, at least 450, at least 500, at least 600, at least 700, at least 800, at least 900 or at least 1000 amino acids in length. In various embodiments, fragments can also be, e.g., at most 1000, at most 900, at most 800, at most 700, at most 600, at most 500, at most 450, at most 400, at most 350, at most 300, at most 250, at most 200, at most 150, at most 100, at most 50, at most 25, at most 10, or at most 5 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

The terms "polypeptide variant", "hybrid polypeptide" and "polypeptide mutant" as used herein refers to a polypeptide that comprises an amino acid sequence wherein one or more amino acid residues are inserted into, deleted from and/or substituted into the amino acid sequence relative to another polypeptide sequence. In various embodiments, the number of amino acid residues to be inserted, deleted, or substituted can be, e.g., at least 1, at least 2, at least 3, at least 4, at least 5, at least 10, at least 25, at least 50, at least 75, at least 100, at least 125, at least 150, at least 175, at least 200, at least 225, at least 250, at least 275, at least 300, at least 350, at least 400, at least 450 or at least 500 amino acids in length. Hybrids of the present disclosure include fusion proteins.

A "derivative" of a polypeptide is a polypeptide that has been chemically modified, e.g., conjugation to another chemical moiety such as, for example, polyethylene glycol, albumin (e.g., human serum albumin), phosphorylation, and glycosylation.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm and means that a given sequence is at least 80% identical to another length of another sequence. In various embodiments, the % identity is selected from, e.g., at least 60%, at least 65%, at least 70%, at least 75%, at least 80%, at least 85%, at least 90%, at least 95%, or at least 99% or more sequence identity to a given sequence. In various embodiments, the % identity is in the range of, e.g., about 60% to about 70%, about 70% to about 80%, about 80% to about 85%, about 85% to about 90%, about 90% to about 95%, or about 95% to about 99%.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence. In various embodiments, the % homology is selected from, e.g., at least 60%, at least 65%, at least 70%, at least 75%, at least 80%, at least 85%, at least 90%, at least 95%, or at least 99% or more sequence homology to a given sequence. In various embodiments, the % homology is in the range of, e.g., about 60% to about 70%, about 70% to about 80%, about 80% to about 85%, about 85% to about 90%, about 90% to about 95%, or about 95% to about 99%.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at the NCBI website. See also Altschul et al., J. Mol. Biol. 215:403-10, 1990 (with special reference to the published default setting, i.e., parameters w=4, t=17) and Altschul et al., Nucleic Acids Res., 1997. Sequence searches are typically carried out using the BLASTP program when evaluating a given amino acid sequence relative to amino acid sequences in the Gen Bank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix.

In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is, e.g., less than about 0.1, less than about 0.01, or less than about 0.001.

The term "modification" as used herein refers to any manipulation of the peptide backbone (e.g. amino acid sequence) or the post-translational modifications (e.g. glycosylation) of a polypeptide.

The term "antigen binding molecule" as used herein refers in its broadest sense to a molecule that specifically binds an antigenic determinant. Examples of antigen binding molecules are antibodies, antibody fragments and scaffold antigen binding proteins. An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

As used herein, the term "antigen-binding site" refers to the part of the antigen binding molecule that specifically binds to an antigenic determinant. More particularly, the term "antigen-binding site" refers the part of an antibody that comprises the area which specifically binds to and is complementary to part or all of an antigen. Where an antigen is large, an antigen binding molecule may only bind to a particular part of the antigen, which part is termed an epitope. An antigen-binding site may be provided by, for example, one or more variable domains (also called variable regions). Preferably, an antigen-binding site comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In various embodiments, the antigen is a human protein.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antibody is able to specifically bind to at least two distinct antigenic determinants, for example two binding sites each formed by a pair of an antibody heavy chain variable domain (VH) and an antibody light chain variable domain (VL) binding to different antigens or to different epitopes on the same antigen. Such a bispecific antibody is an 1+1 format. Other bispecific antibody formats are 2+1 formats (comprising two binding sites for a first antigen or epitope and one binding site for a second antigen or epitope) or 2+2 formats (comprising two binding sites for a first antigen or epitope and two binding sites for a second antigen or epitope). Typically, a bispecific antibody comprises two antigen binding sites, each of which is specific for a different antigenic determinant.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. The bispecific antibodies according to the invention are at least "bivalent" and may be "trivalent" or "multivalent" (e.g. "tetravalent" or "hexavalent"). In various embodiments, the antibodies of the present invention have two or more binding sites and are bispecific. That is, the antibodies may be bispecific even in cases where there are more than two binding sites (i.e. that the antibody is trivalent or multivalent). In particular, the invention relates to bispecific bivalent antibodies, having one binding site for each antigen they specifically bind to.

The terms "full-length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called alpha (IgA), delta (IgD), epsilon (IgE), gamma (IgG), or mu (IgM), some of which may be further divided into subtypes, e.g. gamma 1 (IgG1), gamma 2 (IgG2), gamma 3 (IgG3), gamma 4 (IgG4), alpha 1 (IgA1) and alpha 2 (IgA2). The light chain of an antibody may be assigned to one of two types, called kappa and lambda, based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, triabodies, tetrabodies, cross-Fab fragments; linear antibodies; single-chain antibody molecules (e.g., scFv); multispecific antibodies formed from antibody fragments and single domain antibodies. For a review of certain antibody fragments, see Hudson et al., Nat Med 9, 129-134 (2003). For a review of scFv fragments, see e.g., Pluckthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g., U.S. Pat. No. 6,248,516 B1). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full-length antibodies. Antibody fragments can be made by various techniques, including but not limited to proteolytic digestion of an intact antibody as well as production by recombinant host cells (e.g., *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteines from the antibody hinge region. Fab'-SH are Fab' fragments wherein the cysteine residue(s) of the constant domains bear a free thiol group. Pepsin treatment yields an F(ab')2 fragment that has two antigen-combining sites (two Fab fragments) and a part of the Fc region.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g., described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding molecule and thereby providing the antigen binding property of full-length antibodies.

The term "Fc domain" or "Fc region" herein is used to define a C-terminal region of an antibody heavy chain that contains at least a portion of the constant region. The term includes native sequence Fc regions and variant Fc regions. Particularly, a human IgG heavy chain Fc region extends from Cys226, or from Pro230, to the carboxyl-terminus of the heavy chain. However, the C-terminal lysine (Lys447) of the Fc region may or may not be present. The amino acid sequences of the heavy chains are always presented with the C-terminal lysine, however variants without the C-terminal lysine are included in the invention.

An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g., a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). The protuberance and cavity can be made by altering the nucleic acid encoding the polypeptides, e.g., by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, the bispecific antibodies of the invention block the signaling through TNF-α and Activin so as to inhibit the TNF-α-NF-kB signaling pathway and Activin-Smad2/3 signaling pathway.

As used herein, "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g., Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)).

The terms "affinity" or "binding affinity" as used herein refers to the strength of the sum total of non-covalent interactions between a single binding site of a molecule (e.g., an antibody) and its binding partner (e.g., an antigen). The affinity of a molecule X for its partner Y can generally be represented by the dissociation constant (KD), which is the ratio of dissociation and association rate constants (koff and kon, respectively). A particular method for measuring affinity is Surface Plasmon Resonance (SPR). As used herein, the term "high affinity" of an antibody refers to an antibody having a Kd of $10^{-9}$ M or less and even more particularly $10^{-10}$ M or less for a target antigen. The term "low affinity" of an antibody refers to an antibody having a Kd of $10^{-8}$ M or higher. The term "reduced binding", as used herein refers to a decrease in affinity for the respective interaction, as measured for example by SPR. Conversely, "increased binding" refers to an increase in binding affinity for the respective interaction.

The term "a bispecific antibody comprising a first antigen-binding molecule that specifically binds to TNF-α and a second antigen-binding molecule that specifically binds to Activin", "a bispecific antibody that specifically binds TNF-α and Activin", "bispecific antigen binding molecule specific for TNF-α and Activin" are used interchangeably herein and refer to a bispecific antibody that is capable of binding TNF-α and Activin with sufficient affinity such that the antibody is useful as a diagnostic and/or therapeutic agent in targeting TNF-α and Activin.

The terms "anti-TNF-α antibody" and "an antibody comprising an antigen-binding site that binds to TNF-α" refer to an antibody that is capable of binding TNF-α, especially a TNF-α polypeptide expressed on a cell surface, with sufficient affinity such that the antibody is useful as a diagnostic and/or therapeutic agent in targeting TNF-α. In one embodiment, the extent of binding of an anti-TNF-α antibody to an unrelated, non-TNF-α protein is less than about 10% of the binding of the antibody to TNF-α as measured, e.g., by radioimmunoassay (RIA) or flow cytometry (FACS) or by a Surface Plasmon Resonance assay using a biosensor system such as a Biacore® system. In certain embodiments, an antigen binding molecule that binds to human TNF-α has a KD value of the binding affinity for binding to human TNF-α of, e.g., from $10^{-8}$ M to $10^{-13}$ M. In one preferred embodiment the respective KD value of the binding affinities is determined in a Surface Plasmon Resonance assay using the Extracellular domain (ECD) of human TNF-α (TNF-α-ECD) for the TNF-α binding affinity. The term "anti-TNF-α antibody" also encompasses bispecific antibodies that are capable of binding TNF-α and a second antigen.

The terms "anti-Activin antibody" and "an antibody comprising an antigen-binding site that binds to Activin" refer to an antibody that is capable of binding Activin, especially a Activin polypeptide expressed on a cell surface, with sufficient affinity such that the antibody is useful as a diagnostic and/or therapeutic agent in targeting Activin. In one embodiment, the extent of binding of an anti-Activin antibody to an unrelated, non-Activin protein is less than about 10% of the binding of the antibody to Activin as measured, e.g., by radioimmunoassay (RIA) or flow cytometry (FACS) or by a Surface Plasmon Resonance assay using a biosensor system such as a Biacore® system. In certain embodiments, an antigen binding molecule that binds to human Activin has a KD value of the binding affinity for binding to human Activin of, e.g., from $10^{-8}$ M to $10^{-13}$ M. In one preferred embodiment the respective KD value of the binding affinities is determined in a Surface Plasmon Resonance assay using the Extracellular domain (ECD) of human Activin (Activin-ECD) for the Activin binding affinity. The term "anti-Activin antibody" also encompasses bispecific antibodies that are capable of binding Activin and a second antigen.

The term "fusion protein" as used herein refers to a fusion polypeptide molecule comprising two or more genes that originally coded for separate proteins, wherein the components of the fusion protein are linked to each other by peptide-bonds, either directly or through peptide linkers. The term "fused" as used herein refers to components that are linked by peptide bonds, either directly or via one or more peptide linkers.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences. A "cleavable linker" refers to a linker that can be degraded or otherwise severed to separate the two components connected by the cleavable linker. Cleavable linkers are generally cleaved by enzymes, typically peptidases, proteases, nucleases, lipases, and the like. Cleavable linkers may also be cleaved by environmental cues, such as, for example, changes in temperature, pH, salt concentration, etc.

The term "peptide linker" as used herein refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$ or $G_4(SG_4)n$ peptide linkers. "n" is generally a number between 1 and 10, typically between 2 and 4.

"Pharmaceutical composition" refers to a composition suitable for pharmaceutical use in an animal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, vehicles, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 21st Ed. 2005, Mack Publishing Co, Easton. A "pharmaceutically acceptable salt" is a salt that can be formulated into a compound for pharmaceutical use including, e.g., metal salts (sodium, potassium, magnesium, calcium, etc.) and salts of ammonia or organic amines.

As used herein, "treatment" (and grammatical variations thereof such as "treat" or "treating") refers to clinical intervention in an attempt to alter the natural course of a disease in the individual being treated and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

The term "effective amount" or "therapeutically effective amount" as used herein refers to an amount of a compound or composition sufficient to treat a specified disorder, condition or disease such as ameliorate, palliate, lessen, and/or delay one or more of its symptoms. In reference to cancers or other unwanted cell proliferation, an effective amount comprises an amount sufficient to: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective amount can be administered in one or more administrations.

The phrase "administering" or "cause to be administered" refers to the actions taken by a medical professional (e.g., a physician), or a person controlling medical care of a patient, that control and/or permit the administration of the agent(s)/compound(s) at issue to the patient. Causing to be administered can involve diagnosis and/or determination of an appropriate therapeutic regimen, and/or prescribing particular agent(s)/compounds for a patient. Such prescribing can include, for example, drafting a prescription form, annotating a medical record, and the like. Where administration is described herein, "causing to be administered" is also contemplated.

The terms "patient," "individual," and "subject" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the patient can be a human (e.g., adult male, adult female, adolescent male, adolescent female, male child, female child) under the care of a physician or other health worker in a hospital, psychiatric care facility, as an outpatient, or other clinical context. In various embodiments, the patient may be an immunocompromised patient or a patient with a weakened immune system including, but not limited to patients having primary immune deficiency, AIDS; cancer and transplant patients who are taking certain immunosuppressive drugs; and those with inherited diseases that affect the immune system (e.g., congenital agammaglobulinemia, congenital IgA deficiency). In various embodiments, the patient has an immunogenic cancer, including, but not limited to bladder cancer, lung cancer, melanoma, and other cancers reported to have a high rate of mutations (Lawrence et al., Nature, 499(7457): 214-218, 2013).

The term "immunotherapy" refers to cancer treatments which include, but are not limited to, treatment using depleting antibodies to specific tumor antigens; treatment using antibody-drug conjugates; treatment using agonistic, antagonistic, or blocking antibodies to co-stimulatory or co-inhibitory molecules (immune checkpoints) such as CTLA-4, PD-1, OX-40, CD137, GITR, LAGS, TIM-3, SIRP, CD40, CD47, Siglec 8, Siglec 9, Siglec 15, TIGIT and VISTA; treatment using bispecific T cell engaging antibodies (BiTE®) such as blinatumomab: treatment involving administration of biological response modifiers such as IL-2, IL-12, IL-15, IL-21, GM-CSF, IFN-α, IFN-β and IFN-γ; treatment using therapeutic vaccines such as sipuleucel-T; treatment using Bacilli Calmette-Guerin (BCG); treatment using dendritic cell vaccines, or tumor antigen peptide vaccines; treatment using chimeric antigen receptor (CAR)-T cells; treatment using CAR-NK cells; treatment using tumor infiltrating lymphocytes (TILs); treatment using adoptively transferred anti-tumor T cells (ex vivo expanded and/or TCR transgenic); treatment using TALL-104 cells; and treatment using immunostimulatory agents such as Toll-like receptor (TLR) agonists CpG and imiquimod.

"Resistant or refractory cancer" refers to tumor cells or cancer that do not respond to previous anti-cancer therapy including, e.g., chemotherapy, surgery, radiation therapy, stem cell transplantation, and immunotherapy. Tumor cells can be resistant or refractory at the beginning of treatment, or they may become resistant or refractory during treatment. Refractory tumor cells include tumors that do not respond at the onset of treatment or respond initially for a short period but fail to respond to treatment. Refractory tumor cells also include tumors that respond to treatment with anticancer therapy but fail to respond to subsequent rounds of therapies. For purposes of this invention, refractory tumor cells also encompass tumors that appear to be inhibited by treatment with anticancer therapy but recur up to five years, sometimes up to ten years or longer after treatment is discontinued. The anticancer therapy can employ chemotherapeutic agents alone, radiation alone, targeted therapy alone, immunotherapy alone, surgery alone, or combinations thereof. For ease of description and not limitation, it will be understood that the refractory tumor cells are interchangeable with resistant tumor.

The term "polymer" as used herein generally includes, but is not limited to, homopolymers; copolymers, such as, for example, block, graft, random and alternating copolymers; and terpolymers; and blends and modifications thereof. Furthermore, unless otherwise specifically limited, the term "polymer" shall include all possible geometrical configurations of the material. These configurations include, but are not limited to isotactic, syndiotactic, and random symmetries.

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions.

"Hybridizing specifically to" or "specific hybridization" or "selectively hybridize to", refers to the binding, duplexing, or hybridizing of a nucleic acid molecule preferentially to a particular nucleotide sequence under stringent conditions when that sequence is present in a complex mixture (e.g., total cellular) DNA or RNA. The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and northern hybridizations are sequence-dependent and are different under different environmental parameters. An extensive guide to the hybridization of nucleic acids can be found in Tijssen, 1993, Laboratory Techniques in Biochemistry and Molecular Biology—Hybridization with Nucleic Acid Probes, part I, chapter 2, "Overview of principles of hybridization and the strategy of nucleic acid probe assays", Elsevier, N.Y.; Sambrook et al., 2001, Molecular Cloning: A Laboratory Manual, Cold Spring Harbor Laboratory, 3.sup.rd ed., NY; and Ausubel et al., eds., Current Edition, Current Protocols in Molecular Biology, Greene Publishing Associates and Wiley Interscience, NY.

Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than about 100 complementary residues on a filter in a Southern or northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes. See Sambrook et al. for a description of SSC buffer. A high stringency wash can be preceded by a low stringency wash to remove background probe signal. An exemplary medium stringency wash for a duplex of, e.g., more than about 100 nucleotides, is 1×SSC at 45° C. for 15 minutes. An exemplary low stringency wash for a duplex of, e.g., more than about 100 nucleotides, is 4-6×SSC at 40° C. for minutes. In general, a signal to noise ratio of 2× (or higher) than that observed for an unrelated probe in the particular hybridization assay indicates detection of a specific hybridization.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe," when used in reference to a polynucleotide, refers to a polynucleotide that is capable of specifically hybridizing to a designated sequence of another polynucleotide. A probe specifically hybridizes to a target complementary polynucleotide but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties. In instances where a probe provides a point of initiation for synthesis of a complementary polynucleotide, a probe can also be a primer.

A "vector" is a polynucleotide that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06. A nucleotide sequence is "operably linked" to a regulatory sequence if the regulatory sequence affects the expression (e.g., the level, timing, or location of expression) of the nucleotide sequence.

A "host cell" is a cell that can be used to express a polynucleotide of the disclosure. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

The term "isolated molecule" (where the molecule is, for example, a polypeptide or a polynucleotide) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

A protein or polypeptide is "substantially pure," "substantially homogeneous," or "substantially purified" when at least about 60% to 75% of a sample exhibits a single species of polypeptide. The polypeptide or protein may be monomeric or multimeric. A substantially pure polypeptide or protein will typically comprise about 50%, 60%, 70%, 80% or 90% W/W of a protein sample, more usually about 95%, and preferably will be over 99% pure. Protein purity or homogeneity may be indicated by a number of means well known in the art, such as polyacrylamide gel electrophoresis of a protein sample, followed by visualizing a single polypeptide band upon staining the gel with a stain well known in the art. For certain purposes, higher resolution may be provided by using HPLC or other means well known in the art for purification.

The terms "label" or "labeled" as used herein refers to incorporation of another molecule in the antibody. In one embodiment, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In another embodiment, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In various embodiments, labels are attached by spacer arms of various lengths to reduce potential steric hindrance.

The term "heterologous" as used herein refers to a composition or state that is not native or naturally found, for example, that may be achieved by replacing an existing natural composition or state with one that is derived from another source. Similarly, the expression of a protein in an organism other than the organism in which that protein is naturally expressed constitutes a heterologous expression system and a heterologous protein.

It is understood that aspect and embodiments of the disclosure described herein include "consisting" and/or "consisting essentially of" aspects and embodiments.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variations.

Tumor Necrosis Factor Ligands

TNF is an immunity-modulating cytokine required for immune processes. The unregulated activities of TNFs can lead to the development of inflammatory diseases. Excess amounts of TNF-expressed in cells are associated with the development of immune diseases, including rheumatoid arthritis, Crohn's disease, psoriatic arthritis, and inflammatory bowel disease. The function of TNF requires binding to its two receptors, TNF receptor 1 (TNFR1) and TNF receptor 2 (TNFR2). Blocking the interaction between TNF and TNFRs has successfully been developed as a therapy in treating inflammatory or autoimmune diseases.

In various embodiments, the bifunctional antagonist of the present invention is a bifunctional molecule comprising a first antigen-binding molecule that specifically binds to TNF-α ligand and a second antigen-binding molecule that specifically binds to Activin or Activin-related ligand. In various embodiments, the bifunctional molecule is capable of binding a TNF-α ligand having an amino acid sequence selected from the group consisting of the amino acid sequences set forth in SEQ ID NOs: 1-5:

Human TNFR1 ECD (SEQ ID NO: 1)

IYPSGVIGLVPHLGDREKRDSVCPQGKYIHPQNNSICCTKCHKGTYLYNDCPGPGQDTDCREC

ESGSFTASENHLRHCLSCSKCRKEMGQVEISSCTVDRDTVCGCRKNQYRHYWSENLFQCFN

CSLCLNGTVHLSCQEKQNTVCTCHAGFFLRENECVSCSNCKKSLECTKLCLPQIENVKGTEDS

GTT

Human TNFR2 ECD (SEQ ID NO: 2)

LPAQVAFTPYAPEPGSTCRLREYYDQTAQMCCSKCSPGQHAKVFCTKTSDTVCDSCEDSTYT

QLWNWVPECLSCGSRCSSDQVETQACTREQNRICTCRPGWYCALSKQEGCRLCAPLRKCRP

GFGVARPGTETSDVVCKPCAPGTFSNTTSSTDICRPHQICNVVAIPGNASMDAVCTSTSPTRS

MAPGAVHLPQPVSTRSQHTQPTPEPSTAPSTSFLLPMGPSPPAEGSTGD

Human TNFR1/CRD1-TNFR2/CRD2/3/4

(SEQ ID NO: 3)

IYPSGVIGLVPHLGDREKRDSVCPQGKYIHPQNNSICCTKCHKGTYLYNDCPGPGQDTDCRSC

EDSTYTQLWNWVPECLSCGSRCSSDQVETQACTREQNRICTCRPGWYCALSKQEGCRLCAP

LRKCRPGFGVARPGTETSDVVCKPCAPGTFSNTTSSTDICRPHQICNVVAIPGNASMDAVCTS

TSPTRSMAPGAVHLPQPVSTRSQHTQPTPEPSTAPSTSFLLPMGPSPPAEGSTGD

Human TNFR1/CRD1/2/3-TNFR2/CRD4

(SEQ ID NO: 4)

IYPSGVIGLVPHLGDREKRDSVCPQGKYIHPQNNSICCTKCHKGTYLYNDCPGPGQDTDCREC

ESGSFTASENHLRHCLSCSKCRKEMGQVEISSCTVDRDTVCGCRKNQYRHYWSENLFQCFN

CSLCLNGTVHLSCQEKQNTVCPCAPGTFSNTTSSTDICRPHQICNVVAIPGNASMDAVCTSTSP

TRSMAPGAVHLPQPVSTRSQHTQPTPEPSTAPSTSFLLPMGPSPPAEGSTGD

TNFR1/ΔCRD4

(SEQ ID NO: 5)

IYPSGVIGLVPHLGDREKRDSVCPQGKYIHPQNNSICCTKCHKGTYLYNDCPGPGQDTDCREC

ESGSFTASENHLRHCLSCSKCRKEMGQVEISSCTVDRDTVCGCRKNQYRHYWSENLFQCFN

CSLCLNGTVHLSCQEKQNTVC

In various embodiments, the bifunctional molecule is capable of binding a TNF-α ligand having an amino acid sequence selected from the group consisting of the amino acid sequences set forth in Table 2:

TABLE 2

| Polypeptides containing the TNF-α Ligand | | |
|---|---|---|
| LIGAND | DATABASE | ACCESSION NO |
| TNF-α | UniProtKB | P01375-1 |

Activin and Activin-Related Ligands

Activins, including Activin A, Activin B and Activin AB, and Activin-related proteins, including Myostatin (GDF-8) and GDF-11, mediate Smad2/3 signaling through binding and activation of their high-affinity receptors ActRIIA and ActRIIB on the cell surface. The Activins and related proteins play a critical role in the regulation of a wide range of biology activities, including mesoderm induction, cell differentiation, myogenesis, bone remodeling, hematopoiesis, fibrogenesis, and reproductive physiology. Follistatin (FST), a secreted glycoprotein, binds to the Activins and Activin-related ligands to negatively control their signaling activities.

In various embodiments, the bifunctional molecule of the present invention is capable of binding an Activin or Activin-related ligand having an amino acid sequence selected from the group consisting of the amino acid sequences set forth in SEQ ID NOs: 6-14:

Human ActRIIA-ECD (SEQ ID NO: 6)

ETQECLFFNANWEKDRTNQTGVEPCYGDKDKRRHCFATWKNISGSIEIVKQGCWLDDINCYD

RTDCVEKKDSPEVYFCCCEGNMCNEKFSYFPEMEVTQPTSNPVTPKPP

Human ActRIIB-ECD (SEQ ID NO: 7)

ETRECIYYNANWELERTNQSGLERCEGEQDKRLHCYASWRNSSGTIELVKKGCWLDDFNCYD

RQECVATEENPQVYFCCCEGNFCNERFTHLPEAGGPEVTYEPPPTAPT

-continued

```
Human Follistatin 315
                                                    (SEQ ID NO: 8)
GNCWLRQAKNGRCQVLYKTELSKEECCSTGRLSTSWTEEDVNDNTLFKWMIFNGGAPNCIPC

KETCENVDCGPGKKCRMNKKNKPRCVCAPDCSNITWKGPVCGLDGKTYRNECALLKARCKE

QPELEVQYQGRCKKTCRDVFCPGSSTCVVDQTNNAYCVTCNRICPEPASSEQYLCGNDGVTY

SSACHLRKATCLLGRSIGLAYEGKCIKAKSCEDIQCTGGKKCLWDFKVGRGRCSLCDELCPDS

KSDEPVCASDNATYASECAMKEAACSSGVLLEVKHSGSCNSISEDTEEEEEDEDQDYSFPISSI

LEW

Human Follistatin AHBS (modified Follistatin)
                                                    (SEQ ID NO: 9)
GNCWLRQAKNGRCQVLYKTELSKEECCSTGRLSTSWTEEDVNDNTLFKWMIFNGGAPNCIPC

KETCENVDCGPGQSCVVDQTGSPRCVCAPDCSNITWKGPVCGLDGKTYRNECALLKARCKE

QPELEVQYQGRCKKTCRDVFCPGSSTCVVDQTNNAYCVTCNRICPEPASSEQYLCGNDGVTY

SSACHLRKATCLLGRSIGLAYEGKCIKAKSCEDIQCTGGKKCLWDFKVGRGRCSLCDELCPDS

KSDEPVCASDNATYASECAMKEAACSSGVLLEVKHSGSCNSISEDTEEEEEDEDQDYSFPISSI

LEW

Human Follistatin 288
                                                   (SEQ ID NO: 10)
GNCWLRQAKNGRCQVLYKTELSKEECCSTGRLSTSWTEEDVNDNTLFKWMIFNGGAPNCIPC

KETCENVDCGPGKKCRMNKKNKPRCVCAPDCSNITWKGPVCGLDGKTYRNECALLKARCKE

QPELEVQYQGRCKKTCRDVFCPGSSTCVVDQTNNAYCVTCNRICPEPASSEQYLCGNDGVTY

SSACHLRKATCLLGRSIGLAYEGKCIKAKSCEDIQCTGGKKCLWDFKVGRGRCSLCDELCPDS

KSDEPVCASDNATYASECAMKEAACSSGVLLEVKHSGSCN

Modified human ActRIIB ECD
                                                   (SEQ ID NO: 11)
ETRECIYYNANWELERTNQSGLERCEGDQDKRLHCYASWRNSSGTIELVKKGCWLDDINCYD

RQECVATKENPQVYFCCCEGNFCNERFTHLPEAGGPEVTYEPPPTAPT

Modified human ActRIIB ECD
                                                   (SEQ ID NO: 12)
ETRECIYYNANWELERTNQSGLERCYGDKDKRRHCYASWRNSSGTIELVKKGCWLDDFNCYD

RQECVATEENPQVYFCCCEGNFCNERFTHLPEAGGPEVTYEPPPTAPT

Modified human ActRIIB ECD
                                                   (SEQ ID NO: 13)
ETRECIYYNANWELERTNQSGLERCEGEQDKRLHCYASWRNSSGTIELVKKGCWDDDFNCY

DRQECVATEENPQVYFCCCEGNFCNERFTHLPEAGGPEVTYEPPPT

Modified human ActRIIA ECD
                                                   (SEQ ID NO: 14)
GAILGRSETQECLFYNANWELERTNQTGVEPCEGEKDKRLHCYATWRNISGSIEIVKKGCWLD

DFNCYDRTDCVETEENPQVYFCCCEGNMCNEKFSYFPEMEVTQPTS
```

In various embodiments, the bifunctional molecule is capable of binding an Activin or Activin-related ligand having an amino acid sequence selected from the group consisting of the amino acid sequences set forth in Table 3:

TABLE 3

Polypeptides containing Activin and Activin-related ligands

| LIGAND | DATABASE | ACCESSION NO |
|---|---|---|
| Activin A | UniProtKB | A4D1W7-1 |
| Activin B | UniProtKB | P09529-1 |

TABLE 3-continued

Polypeptides containing Activin and Activin-related ligands

| LIGAND | DATABASE | ACCESSION NO |
|---|---|---|
| GDF8 | UniProtKB | A1C2F0-1 |
| GDF11 | UniProtKB | O95390-1 |

TNF-α and/or Activin Antibodies and Antibody Fragments

Methods of generating novel antibodies that bind to TNF-α and/or Activin ligands and/or receptors are known to those skilled in the art. For example, a method for generating a monoclonal antibody that binds specifically to an TNF-α and/or Activin ligand may comprise administering to a mouse an amount of an immunogenic composition comprising the TNF-α and/or Activin ligand effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the TNF-α and/or Activin ligand. Once obtained, a hybridoma can be propagated in a cell culture, optionally in culture conditions where the hybridoma-derived cells produce the monoclonal antibody that binds specifically to TNF-α and/or Activin ligand. The monoclonal antibody may be purified from the cell culture. A variety of different techniques are then available for testing an antigen/antibody interaction to identify particularly desirable antibodies.

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies. See e.g., Jakobovits et al., Proc. Natl. Acad. Sci. (U.S.A.), 90: 2551-2555, 1993; Jakobovits et al., Nature, 362: 255-258, 1993; Lonberg et al., U.S. Pat. No. 5,545,806; and Surani et al., U.S. Pat. No. 5,545,807.

Antibodies can be engineered in numerous ways. They can be made as single-chain antibodies (including small modular immunopharmaceuticals or SMIPs™), Fab and $F(ab')_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science, 240:1041-1043, 1988; Liu et al., Proc. Natl. Acad. Sci. (U.S.A.), 84:3439-3443, 1987; Liu et al., J. Immunol., 139:3521-3526, 1987; Sun et al., Proc. Natl. Acad. Sci. (U.S.A.), 84:214-218, 1987; Nishimura et al., Canc. Res., 47:999-1005, 1987; Wood et al., Nature, 314:446-449, 1985; and Shaw et al., J. Natl Cancer Inst., 80:1553-1559, 1988).

Methods for humanizing antibodies have been described in the art. In some embodiments, a humanized antibody has one or more amino acid residues introduced from a source that is nonhuman, in addition to the nonhuman CDRs. Humanization can be essentially performed following the method of Winter and co-workers (Jones et al., Nature, 321:522-525, 1986; Riechmann et al., Nature, 332:323-327, 1988; Verhoeyen et al., Science, 239:1534-1536, 1988), by substituting hypervariable region sequences for the corresponding sequences of a human antibody. Accordingly, such "humanized" antibodies are chimeric antibodies (U.S. Pat. No. 4,816,567) wherein substantially less than an intact human variable region has been substituted by the corresponding sequence from a nonhuman species. In practice, humanized antibodies are typically human antibodies in which some hypervariable region residues and possibly some framework region residues are substituted by residues from analogous sites in rodent antibodies.

U.S. Pat. No. 5,693,761 to Queen et al, discloses a refinement on Winter et al. for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, Queen teaches using human framework sequences closely homologous in linear peptide sequence to framework sequences of the mouse antibody to be humanized. Accordingly, the methods of Queen focus on comparing framework sequences between species. Typically, all available human variable region sequences are compared to a particular mouse sequence and the percentage identity between correspondent framework residues is calculated. The human variable region with the highest percentage is selected to provide the framework sequences for the humanizing project. Queen also teaches that it is important to retain in the humanized framework, certain amino acid residues from the mouse framework critical for supporting the CDRs in a binding-capable conformation. Potential criticality is assessed from molecular models. Candidate residues for retention are typically those adjacent in linear sequence to a CDR or physically within 6 Å of any CDR residue.

Another method of humanizing antibodies, referred to as "framework shuffling", relies on generating a combinatorial library with nonhuman CDR variable regions fused in frame into a pool of individual human germline frameworks (Dall'Acqua et al., Methods, 36:43, 2005). The libraries are then screened to identify clones that encode humanized antibodies which retain good binding.

Methods for making fully human antibodies have been described in the art. By way of example, a method for producing an anti-TNF-α antibody or antigen-binding fragment thereof comprises the steps of synthesizing a library of human antibodies on phage, screening the library with TNF-α polypeptide or an antibody-binding portion thereof, isolating phage that bind TNF-α polypeptide, and obtaining the antibody from the phage. By way of another example, one method for preparing the library of antibodies for use in phage display techniques comprises the steps of immunizing a non-human animal comprising human immunoglobulin loci with TNF-α polypeptide or an antigenic portion thereof to create an immune response, extracting antibody-producing cells from the immunized animal; isolating RNA encoding heavy and light chains of antibodies of the invention from the extracted cells, reverse transcribing the RNA to produce cDNA, amplifying the cDNA using primers, and inserting the cDNA into a phage display vector such that antibodies are expressed on the phage. Recombinant anti-TNF-α antibodies of the invention may be obtained in this way.

Recombinant human anti-TNF-α and/or Activin antibodies of the invention can also be isolated by screening a recombinant combinatorial antibody library. Preferably the library is a scFv phage display library, generated using human VL and VH cDNAs prepared from mRNA isolated from B cells. Methods for preparing and screening such libraries are known in the art. Kits for generating phage display libraries are commercially available (e.g., the Pharmacia Recombinant Phage Antibody System, catalog no.

27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; Fuchs et al., Bio/Technology, 9:1370-1372 (1991); Hay et al., Hum. Antibod. Hybridomas, 3:81-85, 1992; Huse et al., Science, 246:1275-1281, 1989; McCafferty et al., Nature, 348:552-554, 1990; Griffiths et al., EMBO J., 12:725-734, 1993; Hawkins et al., J. Mol. Biol., 226:889-896, 1992; Clackson et al., Nature, 352:624-628, 1991; Gram et al., Proc. Natl. Acad. Sci. (U.S.A.), 89:3576-3580, 1992; Garrad et al., Bio/Technology, 9:1373-1377, 1991; Hoogenboom et al., Nuc. Acid Res., 19:4133-4137, 1991; and Barbas et al., Proc. Natl. Acad. Sci. (U.S.A.), 88:7978-7982, 1991), all incorporated herein by reference.

Human antibodies are also produced by immunizing a non-human, transgenic animal comprising within its genome some or all of human immunoglobulin heavy chain and light chain loci with a human IgE antigen, e.g., a XenoMouse™ animal (Abgenix, Inc./Amgen, Inc.—Fremont, Calif.). XenoMouse™ mice are engineered mouse strains that comprise large fragments of human immunoglobulin heavy chain and light chain loci and are deficient in mouse antibody production. See, e.g., Green et al., Nature Genetics, 7:13-21, 1994 and U.S. Pat. Nos. 5,939,598, 5,985,615, 5,998,209, 6,075,181, 6,091,001, 6,114,598, 6,130,364, 6,162,963 and 6,150,584. XenoMouse™ mice produce an adult-like human repertoire of fully human antibodies and generate antigen-specific human antibodies. In some embodiments, the XenoMouse™ mice contain approximately 80% of the human antibody V gene repertoire through introduction of megabase sized, germline configuration fragments of the human heavy chain loci and kappa light chain loci in yeast artificial chromosome (YAC). In other embodiments, XenoMouse™ mice further contain approximately all of the human lambda light chain locus. See Mendez et al., Nature Genetics, 15:146-156, 1997; Green and Jakobovits, J. Exp. Med., 188:483-495, 1998; and WO 98/24893. In one aspect, the present invention provides a method for making anti-TNF-α and/or Activin antibodies from non-human, non-mouse animals by immunizing non-human transgenic animals that comprise human immunoglobulin loci with a TNF-α and/or Activin polypeptide. One can produce such animals using the methods described in the above-cited documents.

Anti-TNF-α Antibodies

The FDA approved anti-TNF-α antibody, Adalimumab (Abbvie HUMIRA®; DrugBank DB00051), has been used to treat humans. In various embodiments of the present invention, the anti-TNF-α antibody is a human antibody or antigen-binding fragment comprising the heavy chain amino acid sequence set forth in SEQ ID NO: 15:

```
                                               (SEQ ID NO: 15)
EVQLVESGGGLVQPGRSLRLSCAASGFTFDDYAMHWVRQAPGKGLEWVS

AITWNSGHIDYADSVEGRFTISRDNAKNSLYLQMNSLRAEDTAVYYCAK

VSYLSTASSLDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNVYVDGVEVHNAKTK
```

-continued

```
PREEQYNSTYRVVSVLTVLHQDWLNGKEYKCKVSNKALPAPIEKTISKA

KGQPREPQVYTLPPSRDELTKNQVSLTCLVKGFYPSDIAVEWESNGQPE

NNYKTTPPVLDSDGSFFLYSKLTVDKSRWQQGNVFSCSVMHEALHNHYT

QKSLSLSPGK
```

a human antibody or antigen-binding fragment comprising the light chain amino acid sequence set forth in SEQ ID NO: 17:

```
                                               (SEQ ID NO: 17)
DIQMTQSPSSLSASVGDRVTITCRASQGIRNYLAWYQQKPGKAPKLLIY

AASTLQSGVPSRFSGSGSGTDFTLTISSLPEDVATYYCQRYNRAPYTFG

QGTKVEIKRTVAAPSVFIFPPSDEQLKSGTASVVCLLNNFYPREAKVQW

KVDNALQSGNSQESVTEQDSKDSTYSLSSTLTLSKADYEKHKVYACEVT

HQGLSSPVTKSFNRGEC
```

or a human antibody or antigen-binding fragment comprising the heavy chain amino acid sequence set forth in SEQ ID NO: 15 and the light chain amino acid sequence set forth in SEQ ID NO: 17;

a human antibody or antigen-binding fragment comprising the heavy chain variable region amino acid sequence set forth in SEQ ID NO: 16:

```
                                               (SEQ ID NO: 16)
EVQLVESGGGLVQPGRSLRLSCAASGFTFDDYAMHWVRQAPGKGLEWVS

AITWNSGHIDYADSVEGRFTISRDNAKNSLYLQMNSLRAEDTAVYYCAK

VSYLSTASSLDYWGQGTLVTVSS
```

a human antibody or antigen-binding fragment comprising the light chain variable region amino acid sequence set forth in SEQ ID NO: 18:

```
                                               (SEQ ID NO: 18)
DIQMTQSPSSLSASVGDRVTITCRASQGIRNYLAWYQQKPGKAPKLLIY

AASTLQSGVPSRFSGSGSGTDFTLTISSLPEDVATYYCQRYNRAPYTFG

QGTKVEIK
```

or a human antibody or antigen-binding fragment comprising the heavy chain variable region amino acid sequence set forth in SEQ ID NO: 16 and the light chain variable region amino acid sequence set forth in SEQ ID NO: 18.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 15, 16, 17, or 18; wherein the antibody binds specifically to human TNF-α.

The FDA approved anti-TNF-α antibody, Infliximab (Centocor REMICADE®; DrugBank DB00065), has been used to treat humans. In various embodiments of the present invention, the anti-TNF-α antibody is a human antibody or antigen-binding fragment comprising the heavy chain amino acid sequence set forth in SEQ ID NO: 19:

```
                                         (SEQ ID NO: 19)
EVKLEESGGGLVQPGGSMKLSCVASGFIFSNHWMNWVRQSPEKGLEWVA
EIRSKSINSATHYAESVKGRFTISRDDSKSAVYLQMTDLRTEDTGVYYC
SRNYYGSTYDYWGQGTTLTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK
```

a human antibody or antigen-binding fragment comprising the light chain amino acid sequence set forth in SEQ ID NO: 21:

```
                                         (SEQ ID NO: 21)
DILLTQSPAILSVSPGERVSFSCRASQFVGSSIHWYQQRTNGSPRLLIK
YASESMSGIPSRFSGSGSGTDFTLSINTVESEDIADYYCQQSHSWPFTF
GSGTNLEVKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

or a human antibody or antigen-binding fragment comprising the heavy chain amino acid sequence set forth in SEQ ID NO: 19 and the light chain amino acid sequence set forth in SEQ ID NO: 21;

a human antibody or antigen-binding fragment comprising the heavy chain variable region amino acid sequence set forth in SEQ ID NO: 20:

```
                                         (SEQ ID NO: 20)
EVKLEESGGGLVQPGGSMKLSCVASGFIFSNHWMNWVRQSPEKGLEWVA
EIRSKSINSATHYAESVKGRFTISRDDSKSAVYLQMTDLRTEDTGVYYC
SRNYYGSTYDYWGQGTTLTVSS
```

a human antibody or antigen-binding fragment comprising the light chain variable region amino acid sequence set forth in SEQ ID NO: 22:

```
                                         (SEQ ID NO: 22)
DILLTQSPAILSVSPGERVSFSCRASQFVGSSIHWYQQRTNGSPRLLIK
YASESMSGIPSRFSGSGSGTDFTLSINTVESEDIADYYCQQSHSWPFTF
GSGTNLEVK
```

or a human antibody or antigen-binding fragment comprising the heavy chain variable region amino acid sequence set forth in SEQ ID NO: 20 and the light chain variable region amino acid sequence set forth in SEQ ID NO: 22.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 19, 20, 21, or 22; wherein the antibody binds specifically to human TNF-α.

The FDA approved anti-TNF-α antibody, Certolizumab pegol (UCB CIMZIA®; DrugBank DB08904), has been used to treat humans. In various embodiments of the present invention, the anti-TNF-α antibody is a human antibody or antigen-binding fragment comprising the heavy chain amino acid sequence set forth in SEQ ID NO: 23:

```
                                         (SEQ ID NO: 23)
EVQLVESGGGLVQPGGSLRLSCAASGYVFTDYGMNWVRQAPGKGLEWMG
WINTYIGEPIYADSVKGRFTFSLDTSKSTAYLQMNSLRAEDTAVYYCAR
GYRSYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKKVEPKSCDKTHTCAA
```

a human antibody or antigen-binding fragment comprising the light chain amino acid sequence set forth in SEQ ID NO: 25:

```
                                         (SEQ ID NO: 25)
DIQMTQSPSSLSASVGDRVTITCKASQNVGTNVAWYQQKPGKAPKALIY
SASFLYSGVPYRFSGSGSGTDFTLTISSLQPEDFATYYCQQYNIYPLTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

or a human antibody or antigen-binding fragment comprising the heavy chain amino acid sequence set forth in SEQ ID NO: 23 and the light chain amino acid sequence set forth in SEQ ID NO: 25;

a human antibody or antigen-binding fragment comprising the heavy chain variable region amino acid sequence set forth in SEQ ID NO: 24:

```
                                         (SEQ ID NO: 24)
EVQLVESGGGLVQPGGSLRLSCAASGYVFTDYGMNWVRQAPGKGLEWMG
WINTYIGEPIYADSVKGRFTFSLDTSKSTAYLQMNSLRAEDTAVYYCAR
GYRSYAMDYWGQGTLVTVSS
```

a human antibody or antigen-binding fragment comprising the light chain variable region amino acid sequence set forth in SEQ ID NO: 26:

```
                                         (SEQ ID NO: 26)
DIQMTQSPSSLSASVGDRVTITCKASQNVGTNVAWYQQKPGKAPKALIYS
ASFLYSGVPYRFSGSGSGTDFTLTISSLQPEDFATYYCQQYNIYPLTFGQ
GTKVEIK
```

or a human antibody or antigen-binding fragment comprising the heavy chain variable region amino acid sequence set forth in SEQ ID NO: 24 and the light chain variable region amino acid sequence set forth in SEQ ID NO: 26.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 23, 24, 25, or 26; wherein the antibody binds specifically to human TNF-α.

The FDA approved anti-TNF-α antibody, Golimumab (Janssen Biotech SIMPONI®; DrugBank DB06674), has been used to treat humans. In various embodiments of the present invention, the anti-TNF-α antibody is a human antibody or antigen-binding fragment comprising the heavy chain amino acid sequence set forth in SEQ ID NO: 27:

```
                                          (SEQ ID NO: 27)
QVQLVESGGGVVQPGRSLRLSCAASGFIFSSYAMHWVRQAPGNGLEWVAF
MSYDGSNKKYADSVKGRFTISRDNSKNTLYLQMNSLRAEDTAVYYCARDR
GIAAGGNYYYYGMDVWGQGTTVTVSSASTKGPSVFPLAPSSKSTSGGTAA
LGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNY
KTTPPVLDSDGSFFLYSKLTVDKSRWQQGNVFSCSVMHEALHNHYTQKSL
SLSPGK
```

a human antibody or antigen-binding fragment comprising the light chain amino acid sequence set forth in SEQ ID NO: 29:

```
                                          (SEQ ID NO: 29)
EIVLTQSPATLSLSPGERATLSCRASQSVYSYLAWYQQKPGQAPRLLIYD
ASNRATGIPARFSGSGSGTDFTLTISSLEPEDFAVYYCQQRSNWPPFTFG
PGTKVDIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

or a human antibody or antigen-binding fragment comprising the heavy chain amino acid sequence set forth in SEQ ID NO: 27 and the light chain amino acid sequence set forth in SEQ ID NO: 29;

a human antibody or antigen-binding fragment comprising the heavy chain variable region amino acid sequence set forth in SEQ ID NO: 28:

```
                                          (SEQ ID NO: 28)
QVQLVESGGGVVQPGRSLRLSCAASGFIFSSYAMHWVRQAPGNGLEWVAF
MSYDGSNKKYADSVKGRFTISRDNSKNTLYLQMNSLRAEDTAVYYCARDR
GIAAGGNYYYYGMDVWGQGTTVTVSS
```

a human antibody or antigen-binding fragment comprising the light chain variable region amino acid sequence set forth in SEQ ID NO: 30:

```
                                          (SEQ ID NO: 30)
EIVLTQSPATLSLSPGERATLSCRASQSVYSYLAWYQQKPGQAPRLLIYD
ASNRATGIPARFSGSGSGTDFTLTISSLEPEDFAVYYCQQRSNWPPFTFG
PGTKVDIK
```

or a human antibody or antigen-binding fragment comprising the heavy chain variable region amino acid sequence set forth in SEQ ID NO: 28 and the light chain variable region amino acid sequence set forth in SEQ ID NO: 30.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 27, 28, 29, or 30; wherein the antibody binds specifically to human TNF-α.

Anti-Activin Antibodies

In various embodiments of the present invention, the anti-Activin antibody is an anti-Activin A antibody that is a human antibody or antigen-binding fragment comprising the heavy chain amino acid sequence set forth in SEQ ID NO: 31:

```
                                          (SEQ ID NO: 31)
QVQLVQSGAEVKKPGASVKVSCKASGYTFTSYGLSWVRQAPGQGLEWMGW
IIPYNGNTNSAQKLQGRVTMTTDTSTSTAYMELRSLRSDDTAVYFCARDR
DYGVNYDAFDIWGQGTMVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKKVEPKSCDKTHTCPPCPAPELLGGPSVFLFPP
KPKDTLMISRTPEVTCVVVDVSHEDPEVKFNVYVDGVEVHNAKTKPREEQ
YNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSP
GK
```

a human antibody or antigen-binding fragment comprising the light chain amino acid sequence set forth in SEQ ID NO: 33:

```
                                          (SEQ ID NO: 33)
SYEVTQAPSVSVSPGQTASITCSGDKLGDKYACWYQQKPGQSPVLVIYQD
SKRPSGIPERFSGSNSGNTATLTISGTQAMDEADYYCQAWDSSTAVFGGG
TKLTVLRTVAAPSVFIFPPSDEQLKSGTASVVCLLNNFYPREAKVQWKVD
NALQSGNSQESVTEQDSKDSTYSLSSTLTLSKADYEKHKVYACEVTHQGL
SSPVTKSFNRGEC
```

or a human antibody or antigen-binding fragment comprising the heavy chain amino acid sequence set forth in SEQ ID NO: 31 and the light chain amino acid sequence set forth in SEQ ID NO: 33;

a human antibody or antigen-binding fragment comprising the heavy chain variable region amino acid sequence set forth in SEQ ID NO: 32:

(SEQ ID NO: 32)
QVQLVQSGAEVKKPGASVKVSCKASGYTFTSYGLSWVRQAPGQGLEWMGW

IIPYNGNTNSAQKLQGRVTMTTDTSTSTAYMELRSLRSDDTAVYFCARDR

DYGVNYDAFDIWGQGTMVTVSS a human antibody or antigen-binding fragment comprising the light chain variable region amino acid sequence set forth in SEQ ID NO: 34:

(SEQ ID NO: 34)
SYEVTQAPSVSVSPGQTASITCSGDKLGDKYACWYQQKPGQSPVLVIYQD

SKRPSGIPERFSGSNSGNTATLTISGTQAMDEADYYCQAWDSSTAVFGGG

TKLTVL or a human antibody or antigen-binding fragment comprising the heavy chain variable region amino acid sequence set forth in SEQ ID NO: 32 and the light chain variable region amino acid sequence set forth in SEQ ID NO: 34.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 31, 32, 33, or 34; wherein the antibody binds specifically to human Activin A.

In various embodiments of the present invention, the anti-Activin antibody is an anti-Activin A antibody that is a human antibody or antigen-binding fragment comprising the heavy chain amino acid sequence set forth in SEQ ID NO: 35:

(SEQ ID NO: 35)
QVQLQESGPGLVKPSETLSLTCTVSGGSFSSHFWSWIRQPPGKGLEWIGY

ILYTGGTSFNPSLKSRVSMSVGTSKNQFSLKLSSVTAADTAVYYCARARS

GITFTGIIVPGSFDIWGQGTMVTVSSASTKGPSVFPLAPCSRSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLS

LGK a human antibody or antigen-binding fragment comprising the light chain amino acid sequence set forth in SEQ ID NO: 37:

(SEQ ID NO: 37)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

-continued

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC or a human antibody or antigen-binding fragment comprising the heavy chain amino acid sequence set forth in SEQ ID NO: 35 and the light chain amino acid sequence set forth in SEQ ID NO: 37;

a human antibody or antigen-binding fragment comprising the heavy chain variable region amino acid sequence set forth in SEQ ID NO: 36:

(SEQ ID NO: 36)
QVQLQESGPGLVKPSETLSLTCTVSGGSFSSHFWSWIRQPPGKGLEWIGY

ILYTGGTSFNPSLKSRVSMSVGTSKNQFSLKLSSVTAADTAVYYCARARS

GITFTGIIVPGSFDIWGQGTMVTVSS a human antibody or antigen-binding fragment comprising the light chain variable region amino acid sequence set forth in SEQ ID NO: 38:

(SEQ ID NO: 38)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK or a human antibody or antigen-binding fragment comprising the heavy chain variable region amino acid sequence set forth in SEQ ID NO: 36 and the light chain variable region amino acid sequence set forth in SEQ ID NO: 38.

In various embodiments, the invention provides antibodies, comprising a heavy chain, a light chain, or both a heavy chain and light chain; a heavy chain variable region, a light chain variable region, or both a heavy chain variable region and light chain variable region; wherein the heavy chain, light chain, heavy chain variable region, or light chain variable region comprises a sequence that has at least about 75%, at least about 80%, at least about 85%, at least about 90%, 91%, 92%, 93%, 94%, 95%, 96%, 97%, 98%, or at least about 99% identity to the amino acid sequences as set forth in SEQ ID NOs: 35, 36, 37, or 38; wherein the antibody binds specifically to human Activin A.

Linkers

In various embodiments, the first antigen-binding molecule that specifically binds to TNF-α ligand is attached to the second antigen-binding molecule that specifically binds to Activin or Activin-related ligand by a linker and/or a hinge linker peptide. The linker or hinge linker may be an artificial sequence of between 5, 10, 15, 20, 30, 40 or more amino acids that are relatively free of secondary structure or display α-helical conformation.

Peptide linker provides covalent linkage and additional structural and/or spatial flexibility between protein domains. As known in the art, peptide linkers contain flexible amino acid residues, such as glycine and serine. In various embodiments, peptide linker may include 1-100 amino acids. In various embodiments, a spacer can contain motif of GGGSGGGS (SEQ ID NO: 81). In other embodiments, a linker can contain motif of GGGGS (SEQ ID NO: 84)n, wherein n is an integer from 1 to 10. In other embodiments, a linker can also contain amino acids other than glycine and serine. In another embodiment, a linker can contain other protein motifs, including but not limited to, sequences of α-helical conformation such as AEAAAKEAAAKEAAAKA (SEQ ID NO: 79). In various embodiments, linker length and composition can be tuned to optimize activity or developability, including but not limited to, expression level and aggregation propensity. In another embodiment, the peptide linker can be a simple chemical bond, e.g., an amide bond (e.g., by chemical conjugation of PEG).

Exemplary peptide linkers are provided in Table 4:

TABLE 4

| Linker sequence | SEQ ID NO: |
|---|---|
| GGGSGGGSGGGS | 74 |
| GGGS | 75 |
| GSSGGSGGSGGSG | 76 |
| GSSGT | 77 |
| GGGGSGGGGSGGGS | 78 |
| AEAAAKEAAAKEAAAKA | 79 |
| GGGGSGGGGSGGGGSGGGGS | 80 |
| GGGSGGGS | 81 |
| GSGST | 82 |
| GGSS | 83 |
| GGGGS | 84 |
| GGSG | 85 |
| SGGG | 86 |
| GSGS | 87 |
| GSGSGS | 88 |
| GSGSGSGS | 89 |
| GSGSGSGSGS | 90 |
| GSGSGSGSGSGS | 91 |
| GGGGSGGGGS | 92 |
| GGGGSGGGGSGGGGS | 93 |

Bifunctional Antagonist Molecules

The present invention provides novel polypeptide-based bifunctional antagonist molecules specifically designed to simultaneously neutralize TNF-α signaling and Activin signaling in a potent manner and comprising a first antigen-binding molecule that specifically binds to TNF-α ligand and a second antigen-binding molecule that specifically binds to Activin or Activin-related ligand. In various embodiments, the bifunctional molecule comprises an isolated antibody, or antigen-binding fragment thereof, that specifically binds to TNF-α and an isolated antibody, or antigen-binding fragment thereof, that specifically binds to Activin or Activin-related ligand. Importantly, these bifunctional antagonists also provide advantageous properties such as producibility, stability, binding affinity, biological activity, specific targeting of certain cells, targeting efficiency and reduced toxicity.

Exemplary Bifunctional Antagonist Molecules

In various embodiments, the bifunctional antagonist molecules of the present invention are selected from the group of molecules designed and comprising the fusion partners as described in Table 5:

TABLE 5

| Fusion Partner A (TNFα-Binding Polypeptide) SEQ ID NO: | Linker SEQ ID NOs: | Fusion Partner B (Activin-Binding Polypeptide) SEQ ID NO: |
|---|---|---|
| SEQ ID NO: 16 | 74-93 | SEQ ID NO: 6 |
| SEQ ID NO: 18 | 74-93 | SEQ ID NO: 6 |
| SEQ ID NO: 16 | 74-93 | SEQ ID NO: 7 |
| SEQ ID NO: 18 | 74-93 | SEQ ID NO: 7 |
| SEQ ID NO: 16 | 74-93 | SEQ ID NO: 11 |
| SEQ ID NO: 18 | 74-93 | SEQ ID NO: 11 |
| SEQ ID NO: 16 | 74-93 | SEQ ID NO: 12 |
| SEQ ID NO: 18 | 74-93 | SEQ ID NO: 12 |
| SEQ ID NO: 16 | 74-93 | SEQ ID NO: 13 |
| SEQ ID NO: 18 | 74-93 | SEQ ID NO: 13 |
| SEQ ID NO: 16 | 74-93 | SEQ ID NO: 14 |
| SEQ ID NO: 18 | 74-93 | SEQ ID NO: 14 |
| SEQ ID NO: 16 | 74-93 | SEQ ID NO: 8 |
| SEQ ID NO: 18 | 74-93 | SEQ ID NO: 8 |
| SEQ ID NO: 16 | 74-93 | SEQ ID NO: 9 |
| SEQ ID NO: 18 | 74-93 | SEQ ID NO: 9 |
| SEQ ID NO: 16 | 74-93 | SEQ ID NO: 10 |
| SEQ ID NO: 18 | 74-93 | SEQ ID NO: 10 |
| SEQ ID NO: 16 and SEQ ID NO: 18 | 74-93 | SEQ ID NO: 32 and SEQ ID NO: 34 |
| SEQ ID NO: 16 and SEQ ID NO: 18 | 74-93 | SEQ ID NO: 36 and SEQ ID NO: 38 |
| SEQ ID NO: 20 | 74-93 | SEQ ID NO: 6 |
| SEQ ID NO: 22 | 74-93 | SEQ ID NO: 6 |
| SEQ ID NO: 20 | 74-93 | SEQ ID NO: 7 |
| SEQ ID NO: 22 | 74-93 | SEQ ID NO: 7 |
| SEQ ID NO: 20 | 74-93 | SEQ ID NO: 11 |
| SEQ ID NO: 22 | 74-93 | SEQ ID NO: 11 |
| SEQ ID NO: 20 | 74-93 | SEQ ID NO: 12 |
| SEQ ID NO: 22 | 74-93 | SEQ ID NO: 12 |
| SEQ ID NO: 20 | 74-93 | SEQ ID NO: 13 |
| SEQ ID NO: 22 | 74-93 | SEQ ID NO: 13 |

TABLE 5-continued

| Fusion Partner A (TNFα-Binding Polypeptide) SEQ ID NO: | Linker SEQ ID NOs: | Fusion Partner B (Activin-Binding Polypeptide) SEQ ID NO: |
|---|---|---|
| SEQ ID NO: 20 | 74-93 | SEQ ID NO: 14 |
| SEQ ID NO: 22 | 74-93 | SEQ ID NO: 14 |
| SEQ ID NO: 20 | 74-93 | SEQ ID NO: 8 |
| SEQ ID NO: 22 | 74-93 | SEQ ID NO: 8 |
| SEQ ID NO: 20 | 74-93 | SEQ ID NO: 9 |
| SEQ ID NO: 22 | 74-93 | SEQ ID NO: 9 |
| SEQ ID NO: 20 | 74-93 | SEQ ID NO: 10 |
| SEQ ID NO: 22 | 74-93 | SEQ ID NO: 10 |
| SEQ ID NO: 20 and SEQ ID NO: 22 | 74-93 | SEQ ID NO: 32 and SEQ ID NO: 34 |
| SEQ ID NO: 20 and SEQ ID NO: 22 | 74-93 | SEQ ID NO: 36 and SEQ ID NO: 38 |
| SEQ ID NO: 24 | 74-93 | SEQ ID NO: 6 |
| SEQ ID NO: 26 | 74-93 | SEQ ID NO: 6 |
| SEQ ID NO: 24 | 74-93 | SEQ ID NO: 7 |
| SEQ ID NO: 26 | 74-93 | SEQ ID NO: 7 |
| SEQ ID NO: 24 | 74-93 | SEQ ID NO: 11 |
| SEQ ID NO: 26 | 74-93 | SEQ ID NO: 11 |
| SEQ ID NO: 24 | 74-93 | SEQ ID NO: 12 |
| SEQ ID NO: 26 | 74-93 | SEQ ID NO: 12 |
| SEQ ID NO: 24 | 74-93 | SEQ ID NO: 13 |
| SEQ ID NO: 26 | 74-93 | SEQ ID NO: 13 |
| SEQ ID NO: 24 | 74-93 | SEQ ID NO: 14 |
| SEQ ID NO: 26 | 74-93 | SEQ ID NO: 14 |
| SEQ ID NO: 24 | 74-93 | SEQ ID NO: 8 |
| SEQ ID NO: 26 | 74-93 | SEQ ID NO: 8 |
| SEQ ID NO: 24 | 74-93 | SEQ ID NO: 9 |
| SEQ ID NO: 26 | 74-93 | SEQ ID NO: 9 |
| SEQ ID NO: 24 | 74-93 | SEQ ID NO: 10 |
| SEQ ID NO: 26 | 74-93 | SEQ ID NO: 10 |
| SEQ ID NO: 24 and SEQ ID NO: 26 | 74-93 | SEQ ID NO: 32 and SEQ ID NO: 34 |
| SEQ ID NO: 24 and SEQ ID NO: 26 | 74-93 | SEQ ID NO: 36 and SEQ ID NO: 38 |
| SEQ ID NO: 28 | 74-93 | SEQ ID NO: 6 |
| SEQ ID NO: 30 | 74-93 | SEQ ID NO: 6 |
| SEQ ID NO: 28 | 74-93 | SEQ ID NO: 7 |
| SEQ ID NO: 30 | 74-93 | SEQ ID NO: 7 |
| SEQ ID NO: 28 | 74-93 | SEQ ID NO: 11 |
| SEQ ID NO: 30 | 74-93 | SEQ ID NO: 11 |
| SEQ ID NO: 28 | 74-93 | SEQ ID NO: 12 |
| SEQ ID NO: 30 | 74-93 | SEQ ID NO: 12 |
| SEQ ID NO: 28 | 74-93 | SEQ ID NO: 13 |
| SEQ ID NO: 30 | 74-93 | SEQ ID NO: 13 |
| SEQ ID NO: 28 | 74-93 | SEQ ID NO: 14 |
| SEQ ID NO: 30 | 74-93 | SEQ ID NO: 14 |
| SEQ ID NO: 28 | 74-93 | SEQ ID NO: 8 |
| SEQ ID NO: 30 | 74-93 | SEQ ID NO: 8 |
| SEQ ID NO: 28 | 74-93 | SEQ ID NO: 9 |
| SEQ ID NO: 30 | 74-93 | SEQ ID NO: 9 |
| SEQ ID NO: 28 | 74-93 | SEQ ID NO: 10 |
| SEQ ID NO: 30 | 74-93 | SEQ ID NO: 10 |
| SEQ ID NO: 28 and SEQ ID NO: 30 | 74-93 | SEQ ID NO: 32 and SEQ ID NO: 34 |
| SEQ ID NO: 28 and SEQ ID NO: 30 | 74-93 | SEQ ID NO: 36 and SEQ ID NO: 38 |
| SEQ ID NO: 1 | 74-93 | SEQ ID NO: 6 |
| SEQ ID NO: 1 | 74-93 | SEQ ID NO: 7 |
| SEQ ID NO: 1 | 74-93 | SEQ ID NO: 11 |
| SEQ ID NO: 1 | 74-93 | SEQ ID NO: 12 |
| SEQ ID NO: 1 | 74-93 | SEQ ID NO: 13 |
| SEQ ID NO: 1 | 74-93 | SEQ ID NO: 14 |
| SEQ ID NO: 1 | 74-93 | SEQ ID NO: 8 |
| SEQ ID NO: 1 | 74-93 | SEQ ID NO: 9 |
| SEQ ID NO: 1 | 74-93 | SEQ ID NO: 10 |
| SEQ ID NO: 1 | 74-93 | SEQ ID NO: 32 |
| SEQ ID NO: 1 | 74-93 | SEQ ID NO: 34 |
| SEQ ID NO: 1 | 74-93 | SEQ ID NO: 36 |
| SEQ ID NO: 1 | 74-93 | SEQ ID NO: 38 |
| SEQ ID NO: 2 | 74-93 | SEQ ID NO: 6 |
| SEQ ID NO: 2 | 74-93 | SEQ ID NO: 7 |
| SEQ ID NO: 2 | 74-93 | SEQ ID NO: 11 |
| SEQ ID NO: 2 | 74-93 | SEQ ID NO: 12 |
| SEQ ID NO: 2 | 74-93 | SEQ ID NO: 13 |
| SEQ ID NO: 2 | 74-93 | SEQ ID NO: 14 |
| SEQ ID NO: 2 | 74-93 | SEQ ID NO: 8 |
| SEQ ID NO: 2 | 74-93 | SEQ ID NO: 9 |
| SEQ ID NO: 2 | 74-93 | SEQ ID NO: 10 |
| SEQ ID NO: 2 | 74-93 | SEQ ID NO: 32 |
| SEQ ID NO: 2 | 74-93 | SEQ ID NO: 34 |
| SEQ ID NO: 2 | 74-93 | SEQ ID NO: 36 |
| SEQ ID NO: 2 | 74-93 | SEQ ID NO: 38 |

TABLE 5-continued

| Fusion Partner A (TNFα-Binding Polypeptide) SEQ ID NO: | Linker SEQ ID NOs: | Fusion Partner B (Activin-Binding Polypeptide) SEQ ID NO: |
|---|---|---|
| SEQ ID NO: 3 | 74-93 | SEQ ID NO: 6 |
| SEQ ID NO: 3 | 74-93 | SEQ ID NO: 7 |
| SEQ ID NO: 3 | 74-93 | SEQ ID NO: 11 |
| SEQ ID NO: 3 | 74-93 | SEQ ID NO: 12 |
| SEQ ID NO: 3 | 74-93 | SEQ ID NO: 13 |
| SEQ ID NO: 3 | 74-93 | SEQ ID NO: 14 |
| SEQ ID NO: 3 | 74-93 | SEQ ID NO: 8 |
| SEQ ID NO: 3 | 74-93 | SEQ ID NO: 9 |
| SEQ ID NO: 3 | 74-93 | SEQ ID NO: 10 |
| SEQ ID NO: 3 | 74-93 | SEQ ID NO: 32 |
| SEQ ID NO: 3 | 74-93 | SEQ ID NO: 34 |
| SEQ ID NO: 3 | 74-93 | SEQ ID NO: 36 |
| SEQ ID NO: 3 | 74-93 | SEQ ID NO: 38 |
| SEQ ID NO: 4 | 74-93 | SEQ ID NO: 6 |
| SEQ ID NO: 4 | 74-93 | SEQ ID NO: 7 |
| SEQ ID NO: 4 | 74-93 | SEQ ID NO: 11 |
| SEQ ID NO: 4 | 74-93 | SEQ ID NO: 12 |
| SEQ ID NO: 4 | 74-93 | SEQ ID NO: 13 |
| SEQ ID NO: 4 | 74-93 | SEQ ID NO: 14 |
| SEQ ID NO: 4 | 74-93 | SEQ ID NO: 8 |
| SEQ ID NO: 4 | 74-93 | SEQ ID NO: 9 |
| SEQ ID NO: 4 | 74-93 | SEQ ID NO: 10 |
| SEQ ID NO: 4 | 74-93 | SEQ ID NO: 32 |
| SEQ ID NO: 4 | 74-93 | SEQ ID NO: 34 |
| SEQ ID NO: 4 | 74-93 | SEQ ID NO: 36 |
| SEQ ID NO: 4 | 74-93 | SEQ ID NO: 38 |
| SEQ ID NO: 5 | 74-93 | SEQ ID NO: 6 |
| SEQ ID NO: 5 | 74-93 | SEQ ID NO: 7 |
| SEQ ID NO: 5 | 74-93 | SEQ ID NO: 11 |
| SEQ ID NO: 5 | 74-93 | SEQ ID NO: 12 |
| SEQ ID NO: 5 | 74-93 | SEQ ID NO: 13 |
| SEQ ID NO: 5 | 74-93 | SEQ ID NO: 14 |
| SEQ ID NO: 5 | 74-93 | SEQ ID NO: 8 |
| SEQ ID NO: 5 | 74-93 | SEQ ID NO: 9 |
| SEQ ID NO: 5 | 74-93 | SEQ ID NO: 10 |
| SEQ ID NO: 5 | 74-93 | SEQ ID NO: 32 |
| SEQ ID NO: 5 | 74-93 | SEQ ID NO: 34 |
| SEQ ID NO: 5 | 74-93 | SEQ ID NO: 36 |
| SEQ ID NO: 5 | 74-93 | SEQ ID NO: 38 |

In various embodiments, the bifunctional antagonist molecule of the present invention is selected from the group of molecules as described in Table 6:

TABLE 6

| SEQ ID NOs: |
|---|
| SEQ ID NO: 39 and SEQ ID NO: 17 |
| SEQ ID NO: 40 and SEQ ID NO: 17 |
| SEQ ID NO: 41 and SEQ ID NO: 17 |
| SEQ ID NO: 42 and SEQ ID NO: 17 |
| SEQ ID NO: 43 and SEQ ID NO: 17 |
| SEQ ID NO: 44 and SEQ ID NO: 17 |
| SEQ ID NO: 45 and SEQ ID NO: 17 |
| SEQ ID NO: 46 and SEQ ID NO: 17 |
| SEQ ID NO: 47 and SEQ ID NO: 17 |
| SEQ ID NO: 70 and SEQ ID NO: 71 |
| SEQ ID NO: 72 and SEQ ID NO: 73 |
| SEQ ID NO: 48 |
| SEQ ID NO: 49 |
| SEQ ID NO: 50 |
| SEQ ID NO: 51 |
| SEQ ID NO: 52 |
| SEQ ID NO: 53 |
| SEQ ID NO: 54 |
| SEQ ID NO: 55 |
| SEQ ID NO: 56 |
| SEQ ID NO: 57 and SEQ ID NO: 33 |
| SEQ ID NO: 58 and SEQ ID NO: 37 |
| SEQ ID NO: 59 |
| SEQ ID NO: 60 |
| SEQ ID NO: 61 |

TABLE 6-continued

| SEQ ID NOs: |
|---|
| SEQ ID NO: 62 |
| SEQ ID NO: 63 |
| SEQ ID NO: 64 |
| SEQ ID NO: 65 |
| SEQ ID NO: 66 |
| SEQ ID NO: 67 |
| SEQ ID NO: 68 and SEQ ID NO: 33 |
| SEQ ID NO: 69 and SEQ ID NO: 37 |

Polynucleotides

In another aspect, the present disclosure provides isolated nucleic acid molecules comprising a polynucleotide encoding a bifunctional antagonist molecule of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding bifunctional antagonist molecules is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase.

cDNA is obtained from libraries prepared from mRNA isolated from various tissues that express a bifunctional antagonist molecule. The DNA molecules of the disclosure include full-length genes as well as polynucleotides and fragments thereof. The full-length gene may also include sequences encoding the N-terminal signal sequence.

In various embodiments, the isolated nucleic acid molecules comprise the polynucleotides described herein, and further comprise a polynucleotide encoding at least one heterologous protein described herein. In various embodiments, the nucleic acid molecules further comprise polynucleotides encoding the linkers or hinge linkers described herein.

In various embodiments, the recombinant nucleic acids of the present disclosure may be operably linked to one or more regulatory nucleotide sequences in an expression construct. Regulatory sequences are art-recognized and are selected to direct expression of the bifunctional antagonist molecule. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding a bifunctional antagonist molecule and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding a bifunctional antagonist molecule. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant bifunctional antagonist molecule include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the B-gal containing pBlueBac III).

In various embodiments, a vector will be designed for production of the subject bifunctional antagonist molecule in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject bifunctional antagonist molecule in cells propagated in culture, e.g., to produce proteins, including fusion proteins or variant proteins, for purification.

Accordingly, the present disclosure further pertains to methods of producing the subject bifunctional antagonist molecules. For example, a host cell transfected with an expression vector encoding a bifunctional antagonist molecule can be cultured under appropriate conditions to allow expression of the bifunctional antagonist molecule to occur. The bifunctional antagonist molecule may be secreted and isolated from a mixture of cells and medium containing the bifunctional antagonist molecule. Alternatively, bifunctional antagonist molecule may be retained cytoplasmically or in a membrane fraction and the cells harvested, lysed and the protein isolated. A cell culture includes host cells, media and other byproducts. Suitable media for cell culture are well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Compositions

In another aspect, the present disclosure provides a pharmaceutical composition comprising the isolated bifunctional antagonist molecules in admixture with a pharmaceutically acceptable carrier. Such pharmaceutically acceptable carriers are well known and understood by those of ordinary skill and have been extensively described (see, e.g., Remington's Pharmaceutical Sciences, 18th Edition, A. R. Gennaro, ed., Mack Publishing Company, 1990). The pharmaceutically acceptable carriers may be included for purposes of modifying, maintaining or preserving, for example, the pH, osmolarity, viscosity, clarity, color, isotonicity, odor, sterility, stability, rate of dissolution or release, adsorption or penetration of the composition. Such pharmaceutical compositions may influence the physical state, stability, rate of in vivo release, and rate of in vivo clearance of the polypeptide. Suitable pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute thereof. In one embodiment of the present disclosure, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose. The optimal pharmaceutical composition will be determined by one of ordinary skill in the art depending upon, for example, the intended route of administration, delivery format, and desired dosage.

When parenteral administration is contemplated, the therapeutic pharmaceutical compositions may be in the form of a pyrogen-free, parenterally acceptable aqueous solution comprising the desired bifunctional antagonist molecule in a pharmaceutically acceptable vehicle. A particularly suitable vehicle for parenteral injection is sterile distilled water in which a polypeptide is formulated as a sterile, isotonic solution, properly preserved. In various embodiments, pharmaceutical formulations suitable for injectable administration may be formulated in aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Optionally, the suspension may also contain suitable stabilizers or agents to increase the solubility of the compounds and allow for the preparation of highly concentrated solutions.

In various embodiments, the therapeutic pharmaceutical compositions may be formulated for targeted delivery using a colloidal dispersion system. Colloidal dispersion systems include macromolecule complexes, nanocapsules, microspheres, beads, and lipid-based systems including oil-in-water emulsions, micelles, mixed micelles, and liposomes. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

In various embodiments, oral administration of the pharmaceutical compositions is contemplated. Pharmaceutical compositions that are administered in this fashion can be formulated with or without those carriers customarily used in the compounding of solid dosage forms such as tablets and capsules. In solid dosage forms for oral administration (capsules, tablets, pills, dragees, powders, granules, and the like), one or more therapeutic compounds of the present disclosure may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming, and preservative agents.

In various embodiments, topical administration of the pharmaceutical compositions, either to skin or to mucosal membranes, is contemplated. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface-active agents. Keratolytic agents such as those known in the art may also be included. Examples are salicylic acid and sulfur. Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the disclosure (e.g., a bifunctional antagonist molecule), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Additional pharmaceutical compositions contemplated for use herein include formulations involving polypeptides in sustained- or controlled-delivery formulations. Techniques for formulating a variety of other sustained- or controlled-delivery means, such as liposome carriers, bioerodible microparticles or porous beads and depot injections, are also known to those skilled in the art.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every three to four days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively, or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

Therapeutic Uses

In another aspect, the present disclosure provides a method of treating or preventing various complex disease conditions whose pathogenesis involve the activation of both TNF-α-mediated NF-κB signaling pathway and Activin-mediated Smad2/3 signaling pathway.

In various embodiments, the novel bifunctional antagonist molecules of the present invention may have broad applications for the treatment of various disorders which include, but are not limited to, the following conditions: anemia, inflammation, pulmonary hypertension, heart failure, renal failure, muscular dystrophy, arthritis, organ fibrosis and cancer, in a subject, comprising administering to said subject a therapeutically effective amount (either as monotherapy or in a combination therapy regimen) of a bifunctional antagonist molecule of the present disclosure in pharmaceutically acceptable carrier, wherein such administration attenuates the loss of muscle mass and/or loss of muscle function. Specifically, a bifunctional antagonist molecule of the present disclosure is useful in treating various complex diseases, including, but not limited to, blood disorders (such as ineffective erythropoiesis, pancytopenia, myelodysplastic syndromes, bone marrow failure, leukemia, beta-thalassemia, and sickle cell disease), fibrotic diseases (such as nonalcoholic steatohepatitis or NASH, cirrhosis, pulmonary fibrosis, renal fibrosis, polycystic kidney disease, cardiac fibrosis, muscle fibrosis, myelo fibrosis, skin fibrosis, fibrosis of the hand, and fibrosis of the eye), muscular dystrophies (such as DMD, Becker MD, Limb-Girdle MD, Myotonic MD and FSHD), myositis (such as polymyositis and dermatomyositis), myopathies (including inherited myopathy and acquired myopathy), motoneuron diseases (such as Lou Gehrig's Disease or ALS), neurodegenerative diseases (such as Parkinson's disease, Huntington's disease and Alzheimer's disease), cancer cachexia, sarcopenia, bone fragility disorders (such as fracture and metastasis in cancer), cardiovascular diseases (such as pulmonary arterial hypertension, Marfan's syndrome, myocardial infarction, and chronic heart failure), chronic kidney disease (CKD), diabetes, chronic obstructive pulmonary disease (COPD), cytokine storms resulting from infections (such as AIDS, tuberculosis, SARS-CoV, and sepsis), arthritis including rheumatoid arthritis (RA) and osteoarthritis (OA), trauma (such as burns or motorcycle accident), ICU critical care, denervation (such as stroke or spinal cord injury), prolonged bed rest, sarcopenic obesity, and age-related muscle and bone loss (including postmenopausal osteoporosis and age-related sarcopenia), organ or tissue transplantation (such as heart transplantation, kidney transplantation and liver transplantation), and various malignancies (such as leukemia, melanoma, breast cancer, multiple myeloma, prostate cancer, lung cancer, pancreatic cancer, gastric cancer, ovarian cancer, colorectal cancer, brain cancer, bladder cancer, and head-neck cancer) as mono-therapy or co-therapy in combination with immune checkpoint inhibitor such as anti-PD1, anti-PDL1, and anti-CTL4 antibodies or with Chimeric Antigen Receptor (CAR) T-cell therapy.

The present disclosure provides for a method of treating cardiovascular disease in a subject, comprising administering to said subject a therapeutically effective amount (either as monotherapy or in a combination therapy regimen) of a bifunctional antagonist molecule of the present disclosure in pharmaceutically acceptable carrier, wherein such administration attenuates the inflammation and fibrosis of vasculatures and muscles, including smooth muscle, cardiac muscle and skeletal muscle. Specifically, a bifunctional antagonist molecule of the present disclosure is useful in treating heart failure, pulmonary hypertension (including pulmonary arterial hypertension), myocarditis, coronary artery disease, myocardial infarction, cardiac arrhythmias, heart valve disease, cardiomyopathy, pericardial disease, aorta disease, Marfan syndrome and cardiac atrophy.

The present disclosure provides for a method of treating cardiac dysfunction or heart failure in a subject comprising administering an effective amount of a bifunctional antagonist molecule into the subject. The modulation may improve cardiac function of said subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The improvement of cardiac function can be evaluated by echocardiography to measure 1) cardiac pump functions focusing on the ejected blood volume and the efficiency of ejection and 2) myocardial functions focusing on the strength of myocardial contraction.

The present disclosure provides for methods for treating metabolic disorders in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating a metabolic disease selected from obesity, dyslipidemia, diabetes, insulin resistance, sarcopenic obesity, steatosis, and metabolic syndrome, as well as diabetic myopathy, nephropathy, neuropathy, retinopathy, bone loss, impaired glucose tolerance, hyperglycemia, and androgen deprivation.

The present disclosure provides for a method of treating cancer cells in a subject, comprising administering to said subject a therapeutically effective amount (either as monotherapy or in a combination therapy regimen) of a bifunctional antagonist molecule of the present disclosure in pharmaceutically acceptable carrier, wherein such administration inhibits the growth and/or proliferation of a cancer cell. Specifically, a bifunctional antagonist molecule of the present disclosure is useful in treating disorders characterized as cancer. Such disorders include, but are not limited to solid tumors, such as cancers of the breast, respiratory tract, brain, reproductive organs, digestive tract, urinary tract, eye, liver, skin, head and neck, thyroid, parathyroid and their distant metastases, lymphomas, sarcomas, multiple myeloma and leukemia. Examples of breast cancer include, but are not limited to invasive ductal carcinoma, invasive lobular carcinoma, ductal carcinoma in situ, and lobular carcinoma in situ. Examples of cancers of the respiratory tract include, but are not limited to, small-cell and non-small-cell lung carcinoma, as well as bronchial adenoma and pleuropulmonary blastoma. Examples of brain cancers include, but are not limited to, brain stem and hypothalmic glioma, cerebellar and cerebral astrocytoma, medulloblastoma, ependymoma, as well as neuroectodermal and pineal tumor. Tumors of the male reproductive organs include, but are not limited to, prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small-intestine, and salivary gland cancers. Tumors of the urinary tract include, but are not limited to bladder, penile, kidney, renal pelvis, ureter, and urethral cancers. Eye cancers include, but are not limited to, intraocular melanoma and retinoblastoma. Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include, but are not limited to nasopharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include, but are not limited to, sarcoma of the soft tissue, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. In certain embodiments, the cancer will be a cancer with high expression of TNF-α and Activin (such as Activin A, Activin B, Activin AB), e.g., pancreatic cancer, gastric cancer, ovarian cancer, colorectal cancer, melanoma, leukemia, lung cancer, prostate cancer, brain cancer, bladder cancer, and head-neck cancer.

The present disclosure provides for a method of treating chronic kidney disease (CKD) in a subject, comprising administering to said subject a therapeutically effective amount (either as monotherapy or in a combination therapy regimen) of a bifunctional antagonist molecule of the present disclosure in pharmaceutically acceptable carrier, wherein such administration attenuates the loss of kidney function and prevents muscle loss or inhibits kidney fibrosis. Specifically, a bifunctional antagonist molecule of the present disclosure is useful in treating CKD including renal failure, interstitial fibrosis, and kidney dialysis as well as protein energy wasting (PEW) associated with CKD. The modulation may improve CKD or PEW of said subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. The improvement of renal function can be evaluated by measuring protein/creatinine ratio (PCR) in the urine and glomerular filtration rate (GFR). Improvement of PEW can be evaluated by measuring serum levels of albumin and inflammatory cytokines, rate of protein synthesis and degradation, body mass, muscle mass, physical activity and nutritional outcomes.

The present disclosure provides for methods for treating autoimmune disease in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating an autoimmune disorder selected from multiple sclerosis, diabetes (type-1), glomerulonephritis, myasthenia gravis, psoriasis, systemic sclerosis and systemic lupus erythematosus, polymyositis and primary biliary cirrhosis.

The present disclosure provides for methods for treating arthritis in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating an arthritis selected from rheumatoid arthritis and osteoarthritis.

The present disclosure provides for methods for treating anorexia in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating an anorexia selected from anorexia nervosa and anorexia-cachexia syndrome.

The present disclosure provides for methods for treating liver disease in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating a liver disease selected from non-alcoholic fatty liver disease, non-alcoholic steatohepatitis, alcoholic fatty liver disease, liver cirrhosis, liver failure, autoimmune hepatitis and hepatocellular carcinoma.

The present disclosure provides for methods for organ or tissue transplantation in a subject, comprising administering to said subject a therapeutically effective amount (either as monotherapy or in a combination therapy regimen) of a bifunctional antagonist molecule of the present disclosure in pharmaceutically acceptable carrier. Specifically, a bifunctional antagonist molecule of the present disclosure is useful in treating a transplantation selected from organ transplantations of the heart, kidneys, liver, lungs, pancreas, intestine and thymus or from tissues transplantations of the bones, tendons, cornea, skin, heart valves, nerves and veins.

The present disclosure provides for methods for treating anemia in a subject, comprising administering to said subject a therapeutically effective amount (either as monotherapy or in a combination therapy regimen) of a bifunctional antagonist molecule of the present disclosure in pharmaceutically acceptable carrier. In various embodiments, the anemia is selected from various anemia disorders including cancer-associated anemia, chemotherapy-induced anemia, chronic kidney disease-associated anemia, iron-deficiency anemia, thalassemia, iron and hemochromatosis, sickle cell disease, aplastic anemia, myelodysplastic syndromes, pancytopenia and bone marrow failure.

The present disclosure provides methods for treating fibrosis in a subject, comprising administering a therapeutically effective amount of the pharmaceutical compositions of the invention to a subject in need thereof. In one embodiment, the subject is a human subject. In various embodiments, the fibrosis is selected from pulmonary fibrosis (such as idiopathic pulmonary fibrosis and cystic fibrosis), liver fibrosis (such as non-alcoholic steatohepatitis and liver cirrhosis), airway fibrosis (such as asthma), cardiac fibrosis (such as myocardial infarction, diastolic dysfunction or cardiac valve disease), renal fibrosis (such as interstitial fibrosis), myelofibrosis, idiopathic retroperitoneal fibrosis, nephrogenic fibrosing dermopathy, intestinal fibrosis in inflammatory bowel diseases (inducing Crohn's disease), keloid, scleroderma, systemic sclerosis, fibrosis of the hand (e.g., Dupuytren's contracture), fibrosis of the eye and arthrofibrosis.

The present disclosure provides methods of treating pain in a subject, comprising administering a therapeutically effective amount of the pharmaceutical compositions of the invention to a subject in need thereof. In one embodiment, the subject is a human subject. In various embodiments, the pain is selected from neuropathic pain, inflammatory pain, or cancer pain.

The present disclosure provides methods of treating bone disease in a subject, comprising administering a therapeutically effective amount of the pharmaceutical compositions of the invention to a subject in need thereof. In one embodiment, the subject is a human subject. In various embodiments, the bone disease is selected from osteomalacia, osteoporosis, osteogenesis imperfecta, fibrodysplasia ossificans progressive, corticosteroid-induced bone loss, bone fracture, and bone metastasis.

The present disclosure provides for a method of inhibiting loss of muscle mass and/or muscle function in a subject comprising administering an effective amount of a bifunctional antagonist molecule into the subject. The modulation may attenuate the loss of the muscle mass and/or function of said subject by at least 5%, 10%, at least 25%, at least 50%, at least 75%, or at least 90%. The inhibition of loss of muscle mass and function can be evaluated by using imaging techniques and physical strength tests. Examples of imaging techniques for muscle mass evaluation include Dual-Energy X-Ray Absorptiometry (DEXA), Magnetic Resonance Imaging (MRI), and Computed Tomography (CT). Examples of muscle function tests include grip strength test, stair climbing test, short physical performance battery (SPPB) and 6-minute walk, as well as maximal inspiratory pressure (MIP) and maximal expiratory pressure (MEP) that are used to measure respiratory muscle strength.

"Therapeutically effective amount" or "therapeutically effective dose" refers to that amount of the therapeutic agent being administered which will relieve to some extent one or more of the symptoms of the disorder being treated.

A therapeutically effective dose can be estimated initially from cell culture assays by determining an $IC_{50}$. A dose can then be formulated in animal models to achieve a circulating plasma concentration range that includes the $IC_{50}$ as determined in cell culture. Such information can be used to more accurately determine useful doses in humans. Levels in plasma may be measured, for example, by HPLC. The exact composition, route of administration and dosage can be chosen by the individual physician in view of the subject's condition.

Dosage regimens can be adjusted to provide the optimum desired response (e.g., a therapeutic or prophylactic response). For example, a single bolus can be administered, several divided doses (multiple or repeat or maintenance) can be administered over time and the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present disclosure will be dictated primarily by the unique characteristics of the antibody and the particular therapeutic or prophylactic effect to be achieved.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

An exemplary, non-limiting daily dosing range for a therapeutically or prophylactically effective amount of a bifunctional antagonist molecule of the disclosure can be 0.001 to 100 mg/kg, 0.001 to 90 mg/kg, 0.001 to 80 mg/kg, 0.001 to 70 mg/kg, 0.001 to 60 mg/kg, 0.001 to 50 mg/kg, 0.001 to 40 mg/kg, 0.001 to 30 mg/kg, 0.001 to 20 mg/kg, 0.001 to 10 mg/kg, 0.001 to 5 mg/kg, 0.001 to 4 mg/kg, 0.001 to 3 mg/kg, 0.001 to 2 mg/kg, 0.001 to 1 mg/kg, 0.010 to 50 mg/kg, 0.010 to 40 mg/kg, 0.010 to 30 mg/kg, 0.010 to 20 mg/kg, 0.010 to 10 mg/kg, 0.010 to 5 mg/kg, 0.010 to 4 mg/kg, 0.010 to 3 mg/kg, 0.010 to 2 mg/kg, 0.010 to 1 mg/kg, 0.1 to 50 mg/kg, 0.1 to 40 mg/kg, 0.1 to 30 mg/kg, 0.1 to 20 mg/kg, 0.1 to 10 mg/kg, 0.1 to 5 mg/kg, 0.1 to 4 mg/kg, 0.1 to 3 mg/kg, 0.1 to 2 mg/kg, 0.1 to 1 mg/kg, 1 to 50 mg/kg, 1 to 40 mg/kg, 1 to 30 mg/kg, 1 to 20 mg/kg, 1 to 10 mg/kg, 1 to 5 mg/kg, 1 to 4 mg/kg, 1 to 3 mg/kg, 1 to 2 mg/kg, or 1 to 1 mg/kg body weight. It is to be noted that dosage values may vary with the type and severity of the conditions to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In various embodiments, the total dose administered will achieve a plasma antibody concentration in the range of, e.g., about 1 to 1000 μg/ml, about 1 to 750 μg/ml, about 1 to 500 μg/ml, about 1 to 250 μg/ml, about 10 to 1000 μg/ml, about 10 to 750 μg/ml, about 10 to 500 μg/ml, about 10 to 250 μg/ml, about 20 to 1000 μg/ml, about 20 to 750 μg/ml, about 20 to 500 μg/ml, about 20 to 250 μg/ml, about 30 to 1000 μg/ml, about 30 to 750 μg/ml, about 30 to 500 μg/ml, about 30 to 250 μg/ml.

Toxicity and therapeutic index of the pharmaceutical compositions of the disclosure can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effective dose is the therapeutic index and it can be expressed as the ratio $LD_{50}/ED_{50}$. Compositions that exhibit large therapeutic indices are generally preferred.

The dosing frequency of the administration of the bifunctional antagonist molecule pharmaceutical composition depends on the nature of the therapy and the particular disease being treated. The subject can be treated at regular intervals, such as weekly or monthly, until a desired therapeutic result is achieved. Exemplary dosing frequencies include, but are not limited to: once weekly without break; once weekly, every other week; once every 2 weeks; once every 3 weeks; weakly without break for 2 weeks, then monthly; weakly without break for 3 weeks, then monthly; monthly; once every other month; once every three months; once every four months; once every five months; or once every six months, or yearly.

Combination Therapy

As used herein, the terms "co-administration", "co-administered" and "in combination with", referring to the a bifunctional antagonist molecule of the disclosure and one or more other therapeutic agents, is intended to mean, and does refer to and include the following: simultaneous administration of such combination of a bifunctional antagonist molecule of the disclosure and therapeutic agent(s) to a subject in need of treatment, when such components are formulated together into a single dosage form which releases said components at substantially the same time to said subject; substantially simultaneous administration of such combination of a bifunctional antagonist molecule of the disclosure and therapeutic agent(s) to a subject in need of treatment, when such components are formulated apart from each other into separate dosage forms which are taken at substantially the same time by said subject, whereupon said components are released at substantially the same time to said subject; sequential administration of such combination of a bifunctional antagonist molecule of the disclosure and therapeutic agent(s) to a subject in need of treatment, when such components are formulated apart from each other into separate dosage forms which are taken at consecutive times by said subject with a significant time interval between each administration, whereupon said components are released at substantially different times to said subject; and sequential administration of such combination of a bifunctional antagonist molecule of the disclosure and therapeutic agent(s) to a subject in need of treatment, when such components are formulated together into a single dosage form which releases said components in a controlled manner whereupon they are concurrently, consecutively, and/or overlappingly released at the same and/or different times to said subject, where each part may be administered by either the same or a different route.

In another aspect, the present disclosure relates to methods of treating muscle wasting diseases in a subject, comprising administration of a combination of a) a therapeutically effective amount of a bifunctional antagonist molecule of the present disclosure; and b) a second agent. This combination therapy may be particularly effective against a muscle wasting disease that is resistant or refractory to treatment using the second agent alone. In various embodiments, second agent is selected from growth hormone, ghrelin, IGF1, antagonists to inflammatory cytokines such as TNF-alpha and TNF-alpha, IL-6, IL-1 and their receptors, and other antagonists to myostatin and activin A and their receptors.

In various embodiments, the combination therapy comprises administering a bifunctional antagonist molecule and the second agent composition simultaneously, either in the same pharmaceutical composition or in separate pharmaceutical composition. In various embodiments, a bifunctional antagonist molecule composition and the second agent composition are administered sequentially, i.e., a bifunctional antagonist molecule composition is administered either prior to or after the administration of the second agent composition.

In various embodiments, the administrations of a bifunctional antagonist molecule composition and the second agent composition are concurrent, i.e., the administration period of a bifunctional antagonist molecule composition and the second agent composition overlap with each other.

In various embodiments, the administrations of a bifunctional antagonist molecule composition and the second agent composition are non-concurrent. For example, in various embodiments, the administration of a bifunctional antagonist molecule composition is terminated before the second agent composition is administered. In various embodiments, the administration second agent composition is terminated before a bifunctional antagonist molecule composition is administered.

The following examples are offered to more fully illustrate the disclosure but are not construed as limiting the scope thereof.

Example 1

The bifunctional antagonist molecules of the present disclosure can be prepared according to recombinant DNA techniques that are well known to those of skill in the art. In this example, the preparation of the bifunctional antagonist molecules is generally described.

cDNAs encoding various novel bifunctional antagonistic polypeptides were generated via gene synthesis and subcloned into mammalian expression plasmids. CHO cells were transiently or stably transfected with the mammalian expression plasmids encoding the individual bifunctional polypeptide antagonists. Transiently transfected CHO cells or stably transfected CHO pools were grown in high-density suspension cultures in a CO2 shaking incubator at 32° C. for 6 to 8 days. The culture media were collected after passing through a 0.22 μm filter unit (Millipore Corporation, MA). The recombinantly expressed bifunctional polypeptides were purified from the culture media via Protein A affinity chromatography using an AKTA PFLC system (GE Healthcare).

Example 2

In this example, the human ligand binding activities of several bifunctional antagonist molecules were measured by biolayer interferometry (BLI) using Octet RED96 (FortéBIO, Pall Corporation, USA). Binding analysis was performed by capturing the polypeptide bifunctional antagonists to biosensors. To measure the rate of association and dissociation, the bifunctional antagonists-captured biosensors were dipped in wells containing different concentrations of ligands (such as TNF-α, Activin A, Activin B, Activin AB, myostatin, and GDF-11) diluted in 1× kinetic buffer for 10 min followed by 10-20 min in 1× kinetic buffer. The bifunctional polypeptide antagonists-captured sensors were also submerged in wells containing 1× kinetic buffer to allow single reference subtraction in order to compensate for natural dissociation of the captured bifunctional antagonists. The binding sensorgrams were collected using the 8-channel detection mode on the biosensor. Data were acquired and analyzed using the FortéBIO data acquisition software v11.1 (FortéBIO, Pall Corporation, USA).

As shown in Table 7, the binding data indicate that A101, A102, A103, A105, A109, A110, A305 and A711 are capable of binding to both TNF-α and Activin A with high affinity.

TABLE 7

| Bifunctional Antagonist Molecule | TNF-α Binding Affinity KD (M) | Activin A Binding Affinity KD (M) |
|---|---|---|
| A101 (SEQ ID NOs: 3 & 6) | ~4.9E−10 | ~1.2E−10 |
| A102 (SEQ ID NOs: 4 & 6) | ~1.1E−10 | ~2.3E−10 |
| A103 (SEQ ID NOs: 5 & 6) | ~4.4E−10 | ~3.0E−10 |
| A105 (SEQ ID NO: 65) | ~2.3E−10 | ~2.1E−10 |
| A109 (SEQ ID NOs: 39 & 17) | ~1.0E−10 | ~5.2E−10 |
| A110 (SEQ ID NOs: 41 & 17) | ~1.0E−10 | ~1.6E−10 |
| A305 (SEQ ID NO: 60) | ~1.0E−10 | ~1.4E−10 |
| A711 (SEQ ID NO: 49) | ~1.0E−10 | ~1.3E−10 |

For A101, A102, A103, A104 and A105, binding affinities were analyzed using CHO expression media containing the respective bifunctional polypeptides. For A109, A110, A305 and A711, binding affinities were analyzed using affinity-purified recombinant bifunctional polypeptides.

The ligand binding affinities of A785, a representative bifunctional antagonist of the current invention designed in the form of a bispecific antibody was examined using BLI analysis. As shown in Table 8, A785 is able to bind both TNF-α and activin A with high affinities.

TABLE 8

| | TNF-α Binding Affinity KD (M) | Activin A Binding Affinity KD (M) |
|---|---|---|
| A785 | ~1.0E−12 | ~3.0E−10 |

Example 3

In this example, the neutralizing activities of the bifunctional antagonists were examined by using cell-based NF-κB and Smad2/3 reporter assays capable of sensing TNF-α signaling and Activin signaling.

Smad2/3 signaling assay. An engineered luciferase reporter cell line, 02012-CAGA-luc, capable of sensing Smad2/3 signaling is used to measure activin A, activin B, Activin AB, myostatin, and GDF-11 signaling activities in cell cultures. To measure neutralizing activities of bifunctional antagonists, 2 nM of human ligand (activin A, activin B, Activin AB, myostatin, or GDF-11) was preincubated with increasing concentrations of each bifunctional antagonist at 0.00004 nM, 0.0004 nM, 0.004 nM, 0.04 nM, 0.4 nM, 4 nM, 40 nM and 400 nM for 1 hour at room temperature. Subsequently, the reaction mixtures were added to the 02012-CAGA-luc cell cultures. After incubation for 5 hours in CO2 incubator at 37° C., the luciferase activities of the 02012-CAGA-luc reporter cultures were measured by using LuminoSkan Ascent (Thermo Scientific). The $IC_{50}$ values were analyzed and plotted using Prism software (GraphPad Software).

NF-κB Signaling Assay. To measure TNF-α-neutralizing activity, a stably transfected luciferase reporter cell line K536-NF-κB-luc capable of sensing TNF-α mediated NF-kB signaling was used to quantify the IC50 value of each bifunctional antagonist to block TNF-α-mediated NF-kB signaling. Specifically, to measure TNF-α-neutralizing activity, human TNF-α at the final concentration of 0.02 nM was preincubated with increasing concentrations of individual bifunctional antagonists at 0.00001 nM, 0.0001 nM, 0.001 nM, 0.01 nM, 0.1 nM, 1.0 nM, 10 nM and 100 nM for 1 hour at room temperature. The reaction mixtures were then added to the K536-NF-kB-luc reporter cell cultures. After 5 hours of incubation at 37° C. in a CO2 incubator, the luciferase activity of the K536-NF-kB-luc reporter cultures was measured using Luminoskan Ascent (Thermo Scientific). The cell-based TNF-α-neutralizing $IC_{50}$ values were calculated and plotted using Prism software (GraphPad Software).

Figure 4:
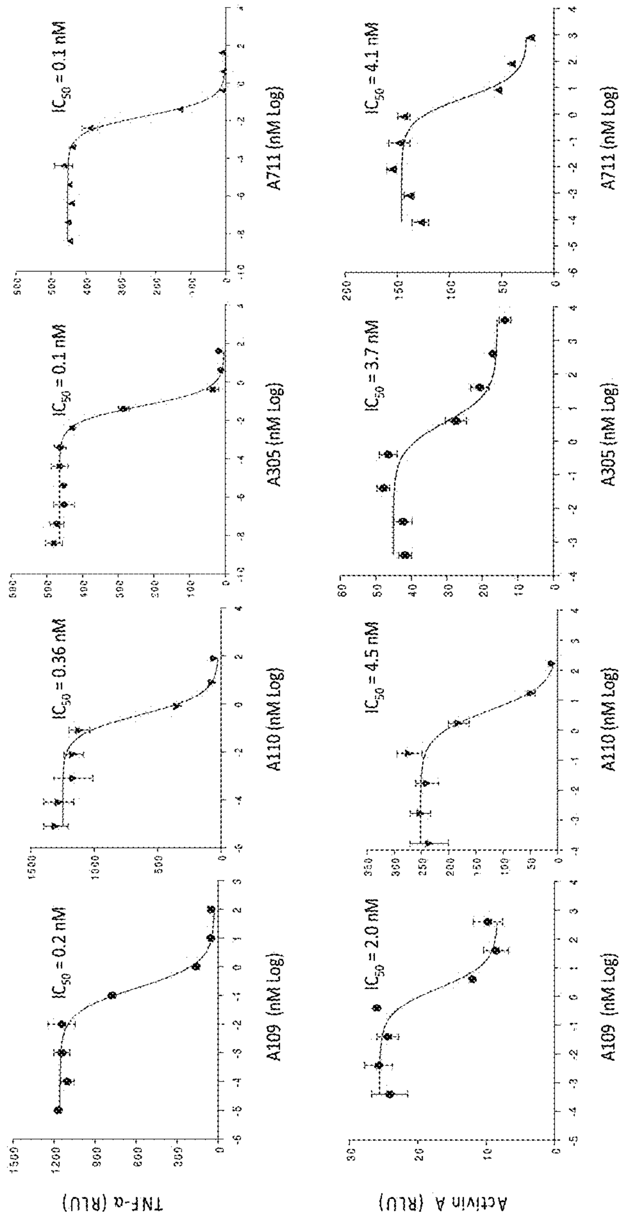
FIG. 4 depicts line graphs showing that A109, A110, A305 and A711 potently neutralize TNF-α and Activin A in Cell-Based Assays. The cell-based TNF-α-neutralizing and Activin-neutralizing $IC_{50}$ values were calculated and plotted using Prism software (GraphPad Software).
Figure 5:
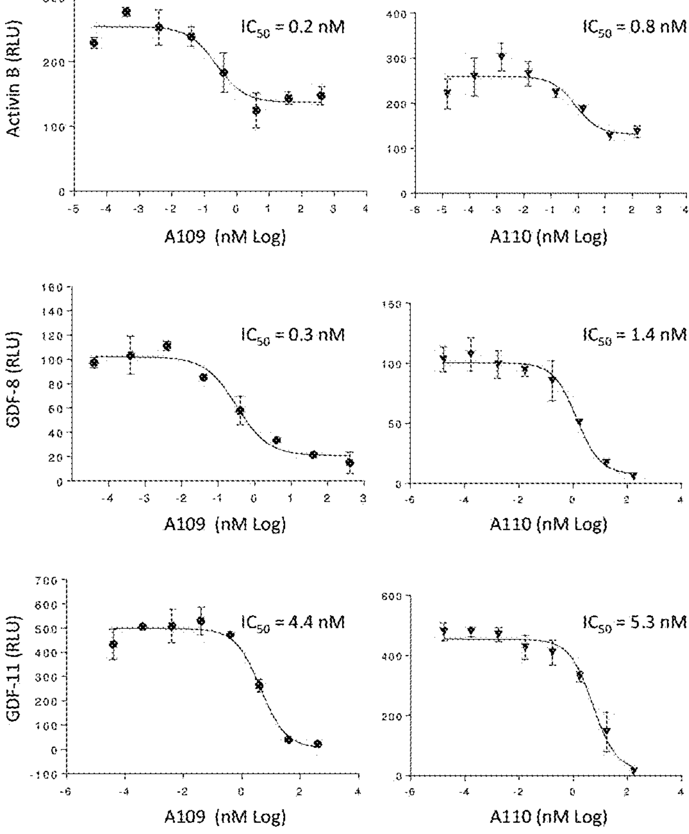
FIG. 5 depicts line graphs showing neutralization of Activin A-Related Ligands Activin B, GDF-8, and GDF-11 by A109 and A110. The cell-based Activin-neutralizing $IC_{50}$ values were calculated and plotted using Prism software (GraphPad Software).

Exemplary data for cell-based neutralizing activities against Activin A and Activin A-related ligands by novel bifunctional antagonist molecules A109, A110, A305 and A711 are shown in FIG. 4 and FIG. 5. A109, A110, A305 and A711 potently inhibited TNF-α-mediated NF-κB signaling with IC50 values ranging between 0.1 nM to 0.36 nM against TNF-α at the concentration of 2 nM (see FIG. 4, upper panels). In parallel, A109, A110, A305 and A711 also potently inhibited Activin A-mediated Smad2/3 signaling with IC50 values ranging between 2.0 to 4.5 nM against Activin A at 2 nM (see FIG. 4, bottom panels). As shown in FIGS. 4, A109 and A110 also strongly neutralized Activin B, GDF-8 and GDF11, ligands that are functionally related to Activin A.

Example 4

Pulmonary arterial hypertension (PAH) is characterized by thickening of pulmonary arterial walls due to proliferation and hypertrophy of pulmonary artery smooth muscle cells as well as increased extracellular matrix deposition. TNF-α and activin A have been shown to be significantly elevated in the lung tissues in patients with PAH and in animal models of PAH. It has been shown that inhibition of either TNF-α or activin A can attenuate pulmonary hypertension. Therefore, TNF-α and activin A are both implicated in the pathogenesis of PAH.

In this example, the ability of A109, a bifunctional antagonist of TNF-α and activin A, to influence pulmonary artery smooth muscle cell remodeling was investigated in comparison with anti-TNF antibody and ActRIIA-Fc by using human primary pulmonary artery smooth muscle cell cultures in the presence of TNF-α and activin A.

Human primary pulmonary artery smooth muscle cells (ATCC) were grown in vascular smooth muscle medium supplemented with 10% FBS in CO2 incubator at 37° C. Upon reaching 80% confluence, the cells were re-plated in medium supplemented with 0.2% FBS and incubated under different conditions with or without addition of various agents as follows: 1) None, 2) TNF-α, 3) activin A, 4) TNF-α+activin A, 5) TNF-α+activin A+anti-TNF antibody, 6) TNF-α+activin A+ActRIIA-Fc, and 7) TNF-α+activin A+A119. After 72 hours of incubation, the cell cultures were photographed with an inverted microscope coupled with a digital camera, and morphometric analysis was performed using ImageJ software.

Figure 6:
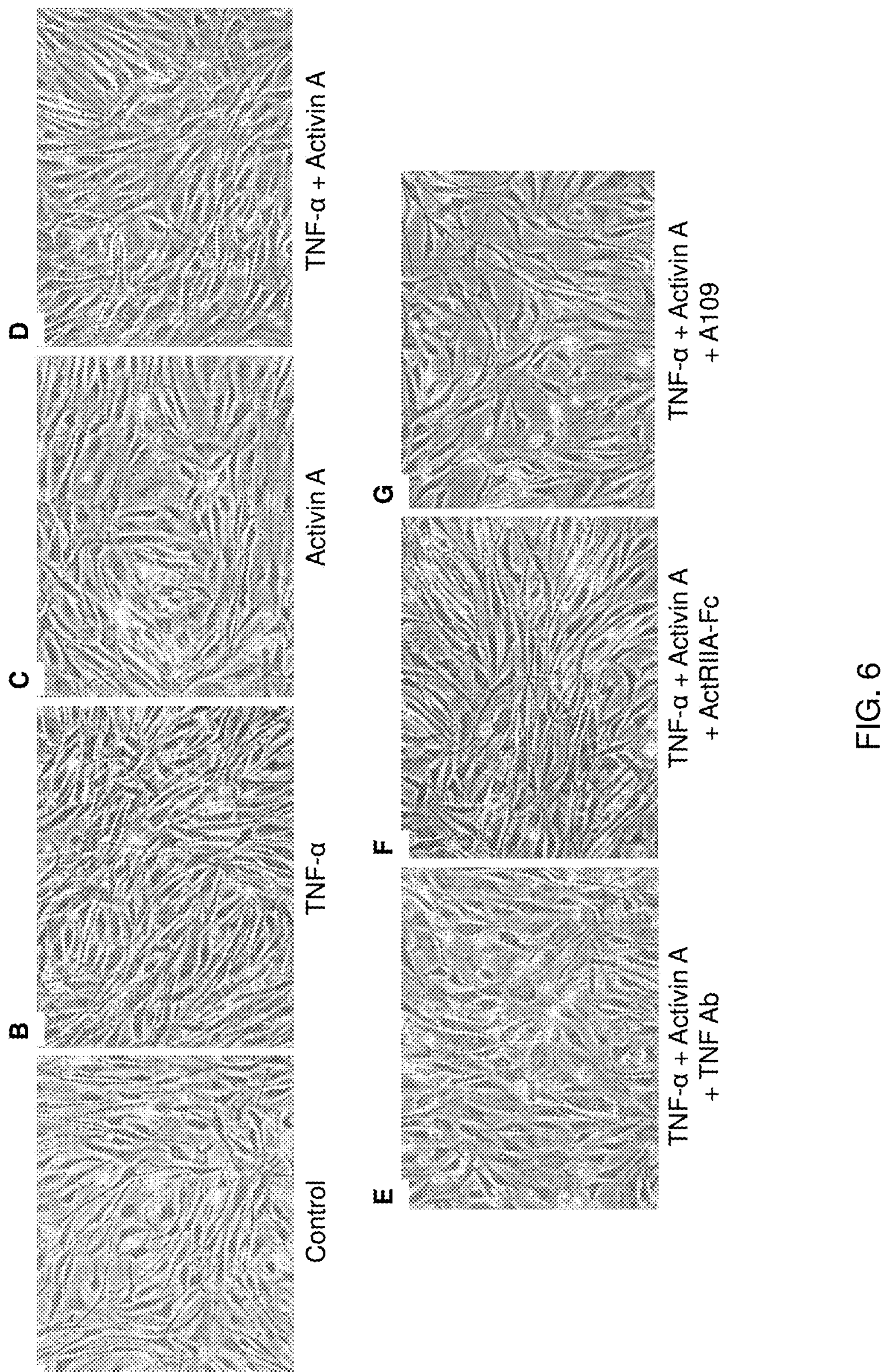
FIG. 6 depicts the changes in cell proliferation and cell morphology of human primary pulmonary artery smooth muscle cells (PASMCs) under different treatment conditions showing that bifunctional antagonist A109 was highly effective in preventing TNFα- and activin A-induced hyperplasia and hypertrophy of PASMCs.
Figure 7:
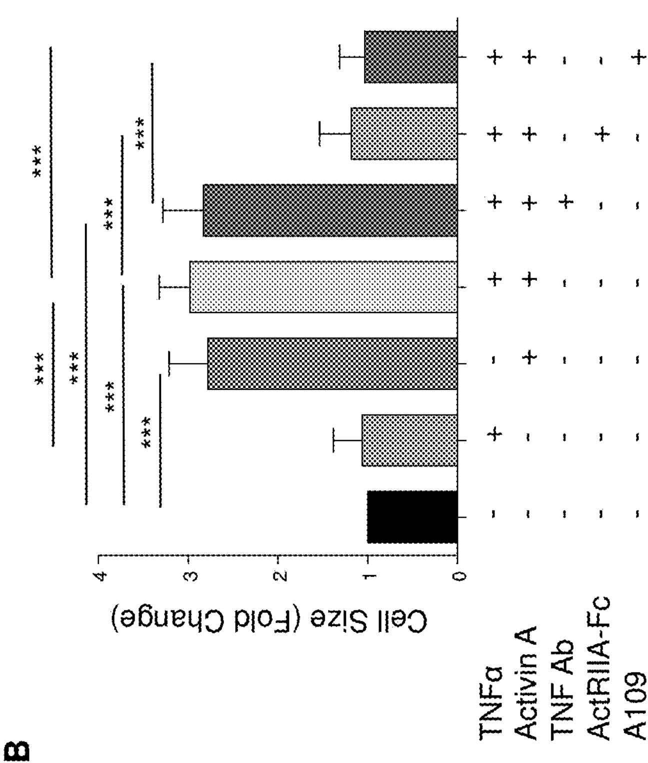
FIG. 7 depicts the bar graphs showing that in the context of elevated TNF-α and activin A, A109 was more effective than anti-TNF antibody or ActRIIA-Fc in preventing both the hyperplasia and the hypertrophy of PASMCs. Morphometric analysis of PASMCs was performed using ImageJ software.
Figure 7:
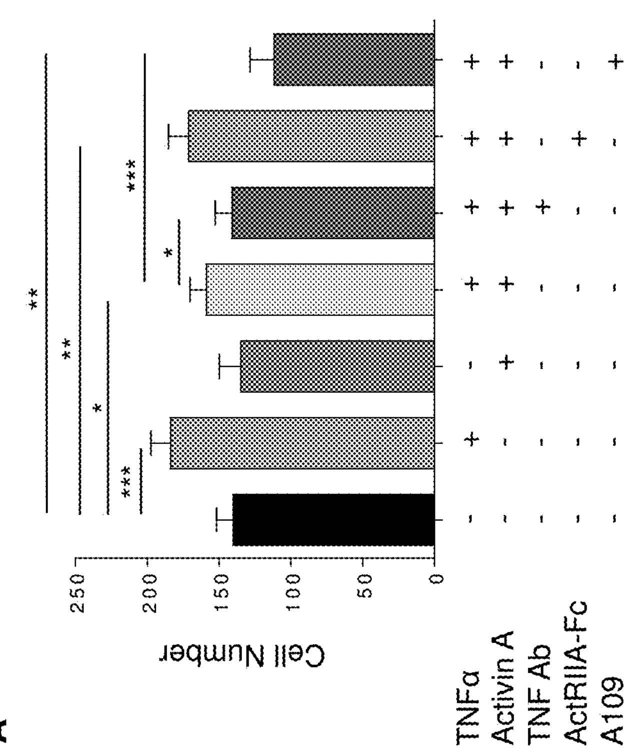

FIG. 6 and FIG. 7 show the effects of TNF-α, activin A, and combination of TNF-α and activin A on cell proliferation and cell size in human primary pulmonary artery smooth muscle cells (PASMCs). Moreover, the figures also show the effect of anti-TNF antibody, ActRIIA-Fc and A109, respectively, on proliferation and size of PASMCs in the context of exogenously added TNF-α and activin A. The data demonstrate that addition of TNF-α to the culture resulted in hyperplasia of the PASMCs due to accelerated cell proliferation (FIG. 6, panel B), addition of activin A to the culture led to hypertrophy of the PASMCs due to enlargement in cell size (FIG. 6, panel C), and addition of TNF-α and activin A in combination to the culture resulted in both hyperplasia and hypertrophy of the PASMCs due to parallel increases in cell proliferation and cell size (FIG. 6, panel D). Therefore, combined exposure to elevated TNF-α and activin A led to a more extensive pathological remodeling of PASMCs characterized by both hyperplasia and hypertrophy. Moreover, in the context of elevated TNF-α and activin A, inhibition of TNF-α by anti-TNF antibody prevented hyperplasia but not hypertrophy of PASMCs (FIG. 6, panel E), inhibition of activin A by ActRIIA-Fc attenuated hypertrophy but not hyperplasia of PASMCs (FIG. 6, panel F), and parallel inhibition of TNF-α and activin A by A109 prevented both hyperplasia and hypertrophy of the PASMCs (FIG. 6, panel G). Morphometric analysis on cell number (FIG. 7, panel A) and cell size (FIG. 7, panel B) demonstrated that only A109 was able to completely prevent both hyperplasia and hypertrophy in the PASMC cultures. Thus, compared to anti-TNF antibody or ActRIIA-Fc, A109 was more effective in preventing the pathological remodeling of PASMCs. The superior ability of A109 to prevent both hyperplasia and hypertrophy of the PASMCs suggests that the novel bifunctional antagonists of TNF-α and activin disclosed in the present invention represent a promising new therapeutic approach to treating PAH.

Example 5

Fibrosis, a pathological process characterized by the replacement of functional tissue with fibrous tissue, may occur in virtually any kind of tissues or organs leading to various fibrotic diseases. As a major fibrotic condition, idiopathic pulmonary fibrosis (IPF) involves extensive injuries in the lung tissue due to sustained inflammation and excessive collagen fibril production and deposition to the extracellular matrix. The expression levels of TNF-α and activin, including activin A and activin B, have been shown to be upregulated in the lung tissues in patients with IPF and in animal models of pulmonary fibrosis. Elevated TNF-α mediates pulmonary inflammation and also plays a role in the transition from pulmonary inflammation to fibrosis, while elevated activin A and activin B can directly promote lung fibrosis by stimulating the overproduction of collagen fibrils.

In this example, A109, a bifunctional antagonist of TNF-α and activin, was evaluated in comparison to anti-TNF antibody and ActRIIA-Fc, respectively, for its ability to counteract fibrosis in a mouse model of bleomycin-induced pulmonary fibrosis.

Bleomycin-induce pulmonary fibrosis mouse model study. All procedures involving animals were approved by the Institutional Committee of Animal Care. Eight-week-old male C57BL/6 mice were purchased from the Jackson Laboratories. Mice were maintained in a 12-h light/dark cycle and with access to water and rodent laboratory chow ad libitum. Mice were acclimated for 1 week before receiving treatment. Bleomycin (Sigma) was dissolved in sterile saline and administered as a single dose of 0.5 mg/kg per animal. Control animals received saline alone. All animals received intratracheal injection (IT) instillations of either bleomycin or saline on day 0. Mice were randomly assigned to the following groups: (1) IT saline (control); (2) IT bleomycin (Bleomycin), (3) IT bleomycin with ActRIIA-Fc treatment (Bleomycin+ActRIIA-Fc); (4) IT bleomycin with TNF antibody treatment (Bleomycin+TNF Ab); (4) IT bleomycin with A109 treatment (Bleomycin+A109). Starting on Day −2, ActRIIA-Fc, anti-TNF and A-109 were given to the individual mouse groups, respectively, once per week via SC administration at the dose between 5 and 10 mg/kg as normalized with the molecular weight of each agent. After two weeks of treatment, the animals were scarified and the right lung tissues were collected in cassettes and fixed in neutral buffered formalin. For histological assessment, the samples were dehydrated in a graded ethanol series, clarified in xylene and embedded in paraffin. Sections of 4-6 μm thickness were cut and stained with Hematoxylin and Eosin (H&E), Masson's Trichrome™ and anti-alpha-SMA antibody coupled with HRP. Fibrotic lung injury was assessed histologically through Ashcroft scoring system (Hübner et al. 2008. PMID: 18476815; DOI: 10.2144/000112729). Ashcroft scores were analyzed at the magnification of 10×.

Figure 8:
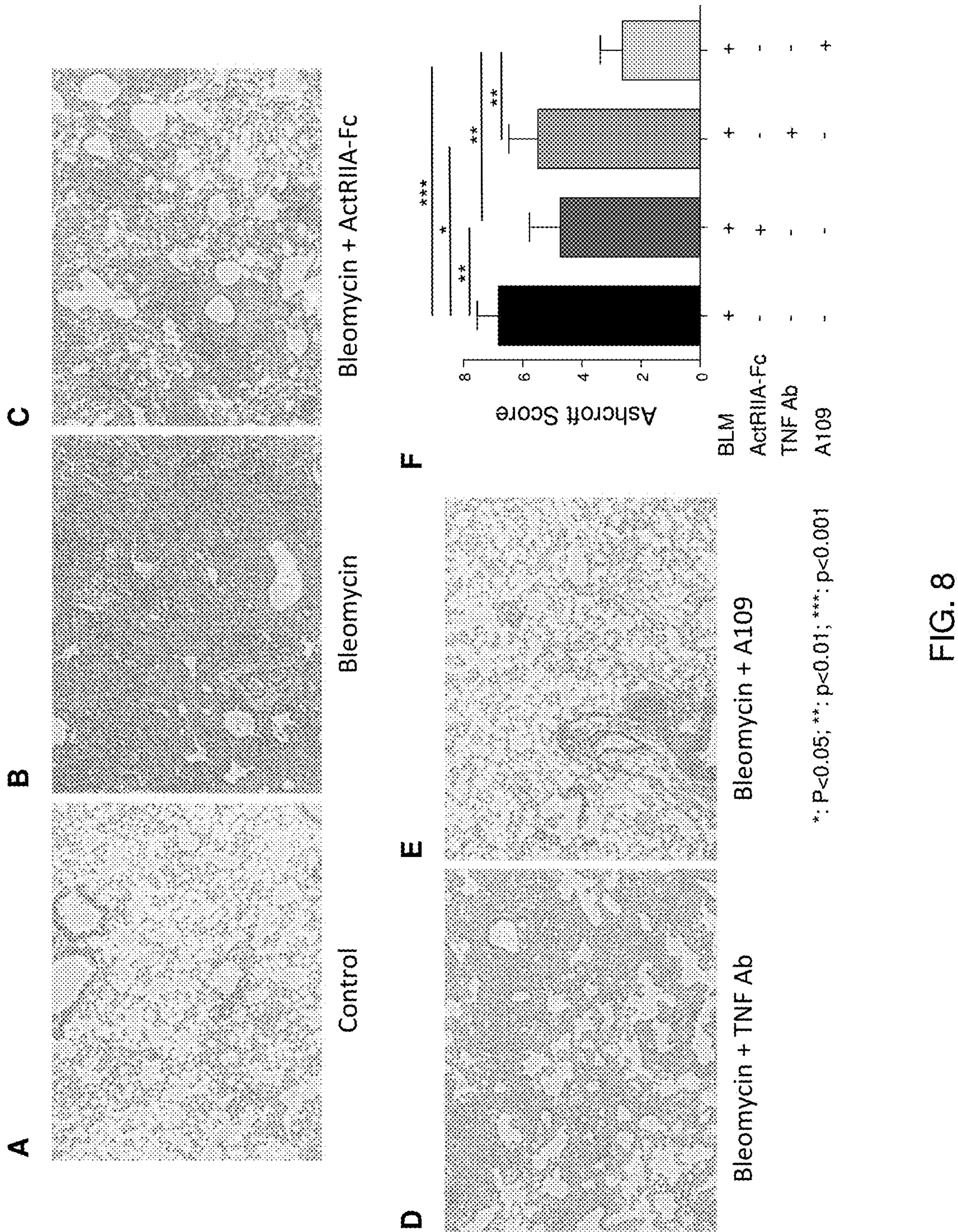
FIG. 8 depicts histological images of H&E-stained lung sections and a bar graph on Ashcraft Scores showing that A109 was more effective than anti-TNF antibody or ActRIIA-Fc in reducing the lung tissue damage and fibrosis in bleomycin-induced pulmonary fibrosis mice.

FIG. 8 shows the histological images of H&E stained lung sections and Ashcraft scores for the lung sections from control and bleomycin animals with or without treatment. The data indicate that treatment with A109 markedly reduced bleomycin-induced lung fibrosis, whereas treatment with TNF antibody or ActRIIA-Fc moderately inhibited bleomycin-induced lung fibrosis. Analysis on Ashcraft scores revealed that A109 treatment resulted in greater reduction of lung fibrosis compared to TNF antibody treatment or ActRIIA-Fc treatment.

Figure 9:
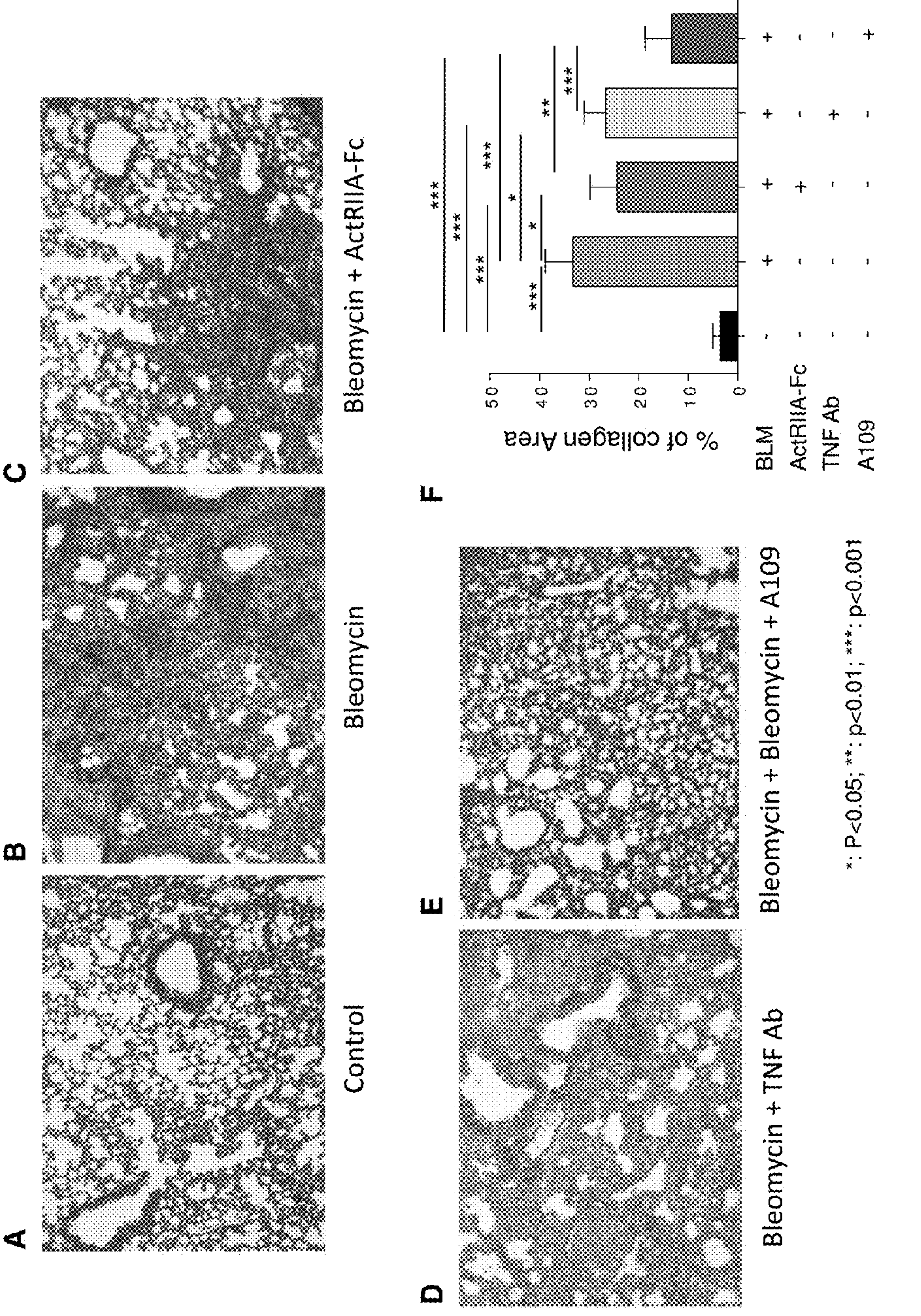
FIG. 9 depicts histology images of Masson's trichrome stained lung sections and a bar graph on quantitative analysis of collagen deposition area showing that A109 attenuated lung fibrosis more effectively than anti-TNF antibody or ActRIIA-Fc in bleomycin-induced pulmonary fibrosis mice.

FIG. 9 depicts the histology images of Masson's trichrome stained lung sections and quantitative analysis of collagen deposition area in the lung sections from control and bleomycin-treated mice. The data indicate that A109 reduced bleomycin-induced collagen deposition more effectively than anti-TNF antibody or ActRIIA-Fc.

Figure 10:
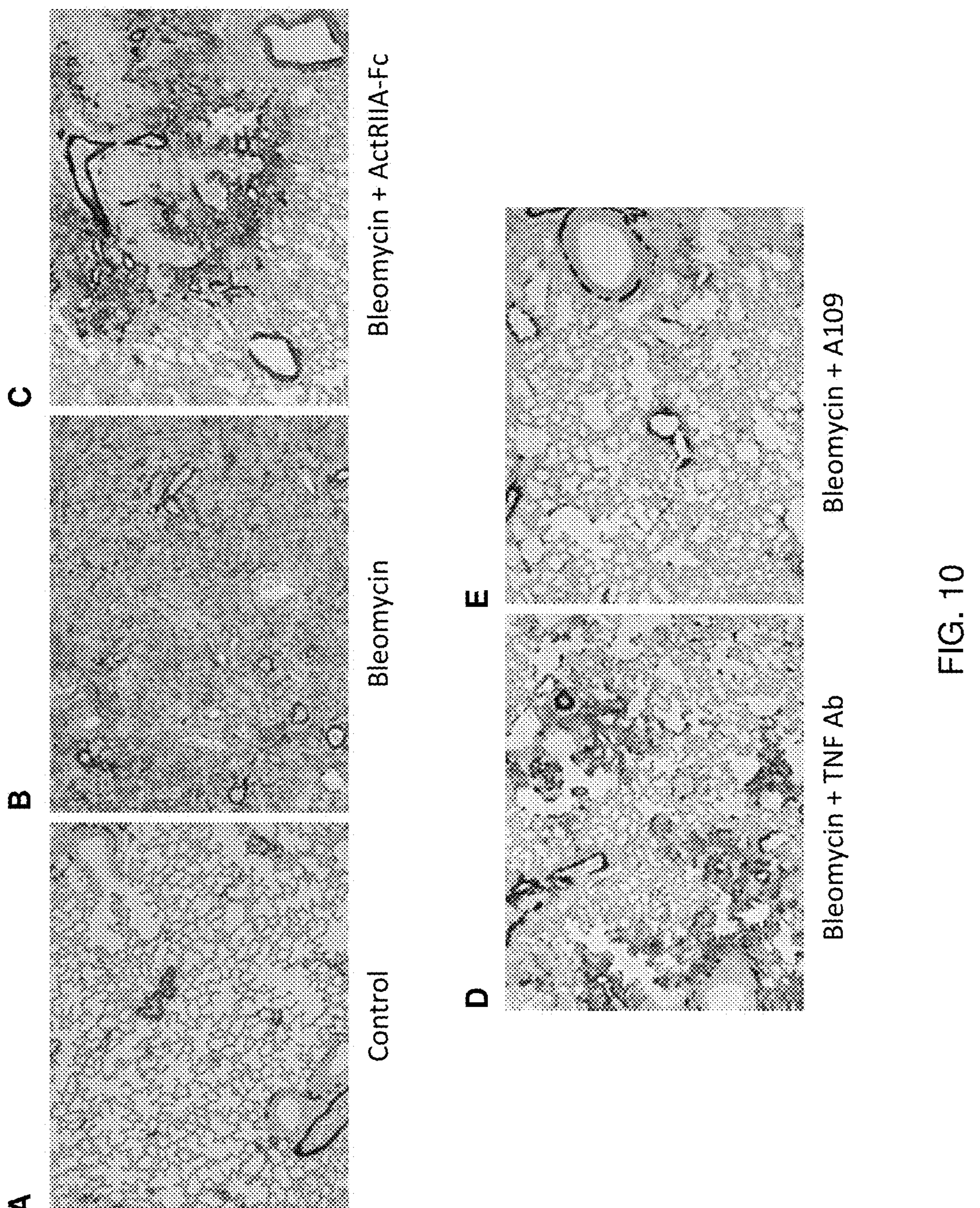
FIG. 10 depicts histology images of αSMA staining in lung sections showing that A109 was more effective than anti-TNF antibody or ActRIIA-Fc in preventing the induction of αSMA in the lung tissues in bleomycin-induced pulmonary fibrosis mice. The lung sections were immunochemically stained with an anti-αSMA antibody and an HRP-labeled secondary antibody.

FIG. 10 shows the immunochemical staining of alpha-smooth muscle actin (αSMA), a marker of fibrosis, in the lung sections from control and bleomycin-treated mice. The data indicates that compared to anti-TNF antibody or ActRIIA-Fc, the bifunctional molecule A109 more effectively attenuated the induction of αSMA immunoreactivity in the bleomycin-treated mice.

Taken together, the data from bleomycin-induced lung fibrosis mice demonstrate that A109, a bifunctional antagonist capable of simultaneously neutralizing TNF-α and activin, is more effective than anti-TNF antibody or ActRIIA-Fc, an activin-neutralizing protein, in counteracting fibrosis. The enhanced anti-fibrosis effect of A109 suggests that the novel bifunctional antagonists of TNF and activin of the present invention represent a promising new approach to treating fibrotic diseases.

Example 6

TNF-α and activin A have been shown to play an importance role in the regulation of bone remodeling. The expression levels of TNF-α as well as activin A are upregulated in bone disorders, and elevated TNF-α and activin A have been both implicated in the pathogenesis of bone loss. In this example, the effect of A109, a novel bifunctional antagonist of activin A and TNF-α, on bone was examined in mice.

Experimental methods. Ten-week-old female CD1 mice were purchased from Envigo. The mice were randomly assigned to two groups (n=6). The treatment group was administered A109 subcutaneously at 30 mg/kg, once per week while the control group received PBS subcutaneously. After 4 weeks of treatment, the animals were euthanized by carbon dioxide inhalation and the right femurs were dissected for imaging by microCT. Skyscan 1172 microCT Instrument and the CTrecon and CTan software from Skyscan were used for the bone imaging analysis. Briefly, femurs were placed in a Styrofoam mold fitted to the rotating stage in the machine. Bones were scanned, and the collection of images was reconstructed for analysis. 3D and 2D microCT imaging analysis were conducted on the trabecular and cortical bones, respectively, to obtain the parameters on bone volume and density.

Figure 11:
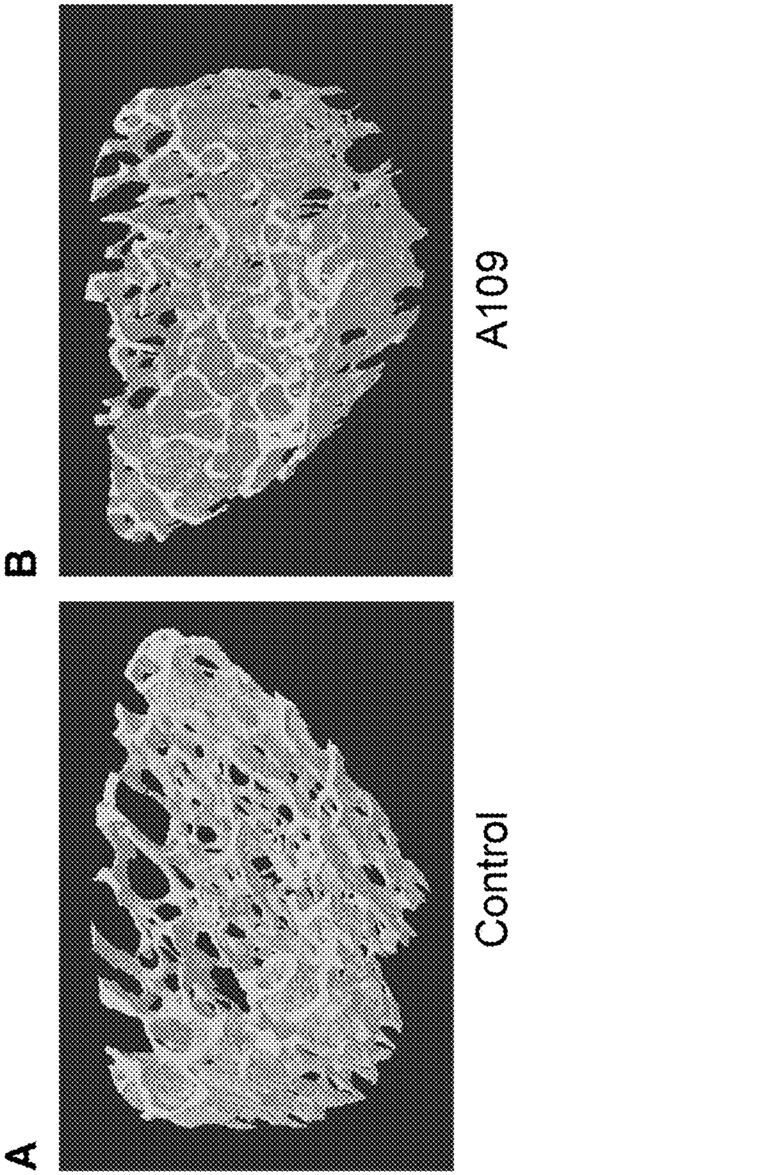
FIG. 11 depicts the representative microCT images of trabecular bone volumes showing that A109 administration enhanced bone mass in normal mice.
Figure 12:
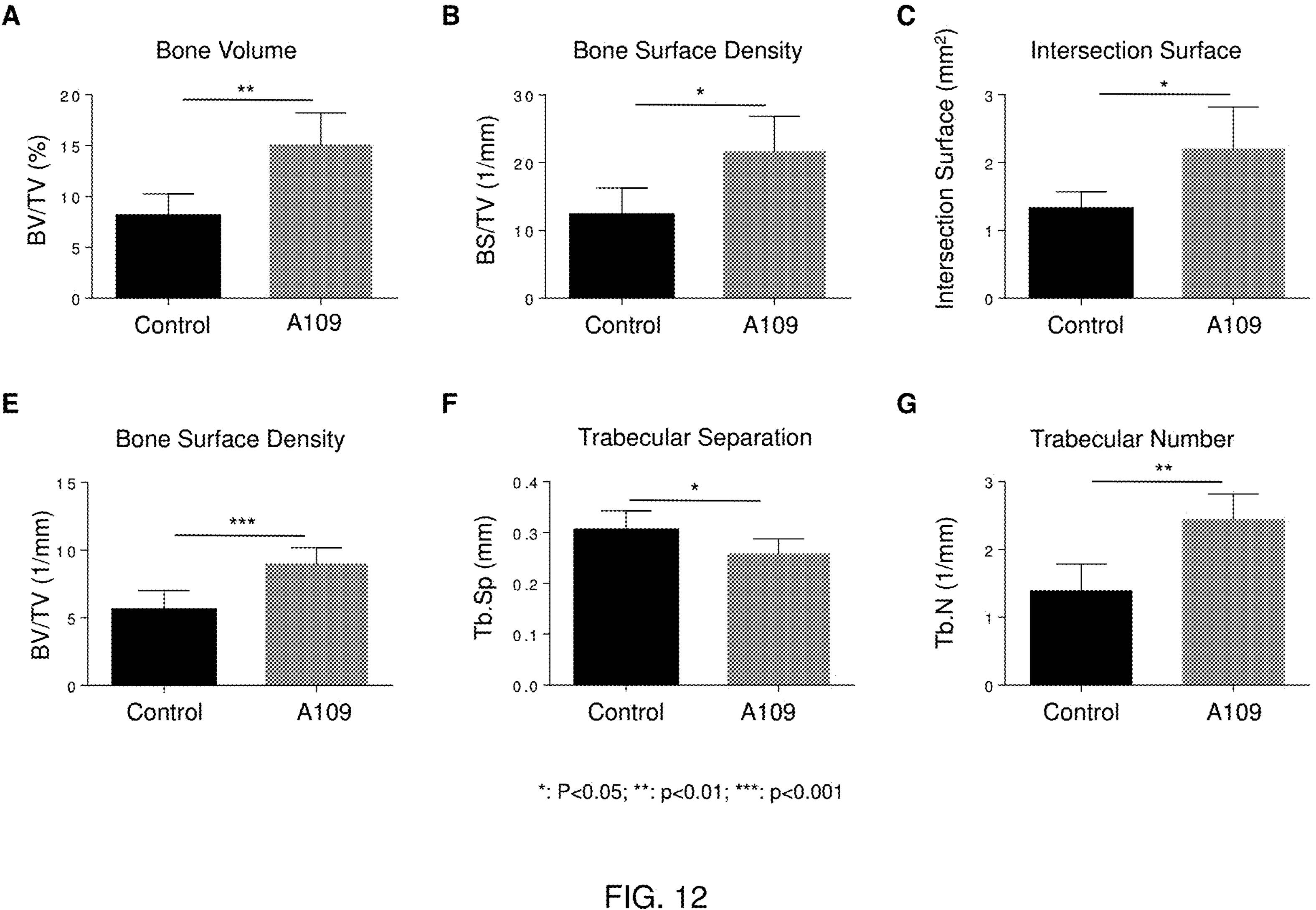
FIG. 12 depicts results of microCT imaging on distal femur bone parameters showing that A109 administration led to marked increases in bone volume and density in CD1 mice.

FIG. 11 shows the representative microCT images of trabecular bone volumes. The data suggest that A109 administration resulted in an enhancement of bone mass in normal mice. Quantitative analysis of the microCT data (FIG. 12) further revealed that A109 administration markedly increased bone volume and density in the CD1 mice.

These results demonstrate that the A109, a novel bifunctional antagonist of activin A and TNF-α, is capable of enhancing bone mass in mice.

All of the articles and methods disclosed and claimed herein can be made and executed without undue experimentation in light of the present invention. While the articles and methods of this invention have been described in terms of preferred embodiments, it will be apparent to those of skill in the art that variations may be applied to the articles and methods without departing from the spirit and scope of the invention. All such variations and equivalents apparent to those skilled in the art, whether now existing or later developed, are deemed to be within the spirit and scope of the invention as defined by the appended claims. All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes. The invention illustratively described herein suitably may be practiced in the absence of any element(s) not specifically disclosed herein. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Sequence Listings

The nucleic and amino acid sequences listed in the accompanying sequence listing are shown using standard letter abbreviations for nucleotide bases and three letter code for amino acids, as defined in 37 C.F.R. 1.822.

SEQ ID NOs: 1-5 are amino acid sequences of various TNF ligands.

SEQ ID NOs: 6-14 are amino acid sequences of various Activin-related ligands.

SEQ ID NOs: 15, 19, 23 and 27 are amino acid sequences of a heavy chain of various antibodies which specifically binds to TNF-α ligand.

SEQ ID NOs: 16, 20, 24 and 28 are amino acid sequences of a heavy chain variable region of various antibodies which specifically binds to TNF-α ligand.

SEQ ID NOs: 17, 21, 25 and 29 are amino acid sequences of a light chain of various antibodies which specifically binds to TNF-α ligand.

SEQ ID NOs: 18, 22, 26 and 30 are amino acid sequences of a light chain variable region of various antibodies which specifically binds to TNF-α ligand.

SEQ ID NOs: 31 and 35 are amino acid sequences of a heavy chain of an antibody which specifically binds to Activin-related ligand.

SEQ ID NOs: 32 and 36 are amino acid sequences of a heavy chain variable region of an antibody which specifically binds to Activin-related ligand.

SEQ ID NOs: 33 and 37 are amino acid sequences of a light chain of an antibody which specifically binds to Activin-related ligand.

SEQ ID NOs: 34 and 38 are amino acid sequences of a light chain variable region of an antibody which specifically binds to Activin-related ligand.

SEQ ID NOs: 39-47 are the amino acid sequences of a heavy chain of a bifunctional antagonist molecule that specifically binds to TNF-α ligand and to Activin or Activin-related ligand.

SEQ ID NOs: 48-56 are the amino acid sequences of various bifunctional antagonist molecules that specifically binds to TNF-α ligand and that specifically binds to Activin or Activin-related ligand.

SEQ ID NOs: 57 and 58 are amino acid sequences of a heavy chain variable region of an antibody which specifically binds to Activin A ligand.

SEQ ID NOs: 59-67 are the amino acid sequences of various bifunctional antagonist molecules that specifically binds to TNF-α ligand and that specifically binds to Activin or Activin-related ligand.

SEQ ID NOs: 68 and 69 are amino acid sequences of a heavy chain variable region of an antibody which specifically binds to Activin A ligand.

SEQ ID NOs: 70 and 72 are amino acid sequences of a heavy chain of a bifunctional antagonist molecule that specifically binds to TNF-α ligand and to Activin or Activin-related ligand.

SEQ ID NOs: 71 and 73 are amino acid sequences of a heavy chain of a bifunctional antagonist molecule that specifically binds to TNF-α ligand and to Activin or Activin-related ligand.

SEQ ID NOS: 74-93 are the amino acid sequences of various peptide linker sequences.

SEQUENCE LISTINGS

```
Human TNFR1 ECD
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTT (SEQ ID NO: 1)
```

-continued

SEQUENCE LISTINGS

Human TNFR2 ECD
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGD (SEQ ID NO: 2)

Human TNFR1/CRD1-TNFR2/CRD2/3/4
IYPSGVIGLVPHLGDREKRDSVCPQGKYIHPQNNSICCTKCHKGTYLYNDCPGPGQDTDCRSC
EDSTYTQLWNWVPECLSCGSRCSSDQVETQACTREQNRICTCRPGWYCALSKQEGCRLCAP
LRKCRPGFGVARPGTETSDVVCKPCAPGTFSNTTSSTDICRPHQICNVVAIPGNASMDAVCTS
TSPTRSMAPGAVHLPQPVSTRSQHTQPTPEPSTAPSTSFLLPMGPSPPAEGSTGD
(SEQ ID NO: 3)

Human TNFR1/CRD1/2/3-TNFR2/CRD4
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCPCAPGTFSNTTSSTDICRPHQICNVVAIPGNASMDAVCTSTSP
TRSMAPGAVHLPQPVSTRSQHTQPTPEPSTAPSTSFLLPMGPSPPAEGSTGD (SEQ ID NO: 4)

TNFR1/ΔCRD4
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVC (SEQ ID NO: 5)

Human ActRIIA-ECD
ETQECLFFNANWEKDRTNQTGVEPCYGDKDKRRHCFATWKNISGSIEIVKQGCWLDDINCYD
RTDCVEKKDSPEVYFCCCEGNMCNEKFSYFPEMEVTQPTSNPVTPKPP (SEQ ID NO: 6)

Human ActRIIB-ECD
ETRECIYYNANWELERTNQSGLERCEGEQDKRLHCYASWRNSSGTIELVKKGCWLDDENCYD
RQECVATEENPQVYFCCCEGNFCNERFTHLPEAGGPEVTYEPPPTAPT (SEQ ID NO: 7)

Human Follistatin 315
GNCWLRQAKNGRCQVLYKTELSKEECCSTGRLSTSWTEEDVNDNTLFKWMIFNGGAPNCIPC
KETCENVDCGPGKKCRMNKKNKPRCVCAPDCSNITWKGPVCGLDGKTYRNECALLKARCKE
QPELEVQYQGRCKKTCRDVFCPGSSTCVVDQTNNAYCVTCNRICPEPASSEQYLCGNDGVTY
SSACHLRKATCLLGRSIGLAYEGKCIKAKSCEDIQCTGGKKCLWDFKVGRGRCSLCDELCPDS
KSDEPVCASDNATYASECAMKEAACSSGVLLEVKHSGSCNSISEDTEEEEEDEDQDYSFPISSI
LEW (SEQ ID NO: 8)

Human Follistatin ΔHBS (modified Follistatin)
GNCWLRQAKNGRCQVLYKTELSKEECCSTGRLSTSWTEEDVNDNTLFKWMIFNGGAPNCIPC
KETCENVDCGPGQSCVVDQTGSPRCVCAPDCSNITWKGPVCGLDGKTYRNECALLKARCKE
QPELEVQYQGRCKKTCRDVFCPGSSTCVVDQTNNAYCVTCNRICPEPASSEQYLCGNDGVTY
SSACHLRKATCLLGRSIGLAYEGKCIKAKSCEDIQCTGGKKCLWDFKVGRGRCSLCDELCPDS
KSDEPVCASDNATYASECAMKEAACSSGVLLEVKHSGSCNSISEDTEEEEEDEDQDYSFPISSI
LEW (SEQ ID NO: 9)

Human Follistatin 288
GNCWLRQAKNGRCQVLYKTELSKEECCSTGRLSTSWTEEDVNDNTLFKWMIFNGGAPNCIPC
KETCENVDCGPGKKCRMNKKNKPRCVCAPDCSNITWKGPVCGLDGKTYRNECALLKARCKE
QPELEVQYQGRCKKTCRDVFCPGSSTCVVDQTNNAYCVTCNRICPEPASSEQYLCGNDGVTY
SSACHLRKATCLLGRSIGLAYEGKCIKAKSCEDIQCTGGKKCLWDFKVGRGRCSLCDELCPDS
KSDEPVCASDNATYASECAMKEAACSSGVLLEVKHSGSCN (SEQ ID NO: 10)

Modified human ActRIIB ECD
ETRECIYYNANWELERTNQSGLERCEGDQDKRLHCYASWRNSSGTIELVKKGCWLDDINCYD
RQECVATKENPQVYFCCCEGNFCNERFTHLPEAGGPEVTYEPPPTAPT (SEQ ID NO: 11)

Modified human ActRIIB ECD
ETRECIYYNANWELERTNQSGLERCYGDKDKRRHCYASWRNSSGTIELVKKGCWLDDENCYD
RQECVATEENPQVYFCCCEGNFCNERFTHLPEAGGPEVTYEPPPTAPT (SEQ ID NO: 12)

Modified human ActRIIB ECD
ETRECIYYNANWELERTNQSGLERCEGEQDKRLHCYASWRNSSGTIELVKKGCWDDDFNCY
DRQECVATEENPQVYFCCCEGNFCNERFTHLPEAGGPEVTYEPPPT (SEQ ID NO: 13)

Modified human ActRIIA ECD
GAILGRSETQECLFYNANWELERTNQTGVEPCEGEKDKRLHCYATWRNISGSIEIVKKGCWLD
DFNCYDRTDCVETEENPQVYFCCCEGNMCNEKFSYFPEMEVTQPTS (SEQ ID NO: 14)

Anti-TNF-α antibody heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNVYVDGVEVHNAKTKPREEQYNSTYRVVSVLTVLH -continued

| SEQUENCE LISTINGS |
|---|

QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGK (SEQ ID NO: 15)

Anti-TNF-α antibody heavy chain variable region amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSS
(SEQ ID NO: 16)

Anti-TNF-α antibody light chain amino acid sequence
DIQMTQSPSSLSASVGDRVTITCRASQGIRNYLAWYQQKPGKAPKLLIYAASTLQSGVPSRFSG
SGSGTDFTLTISSLQPEDVATYYCQRYNRAPYTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC (SEQ ID NO: 17)

Anti-TNF-α antibody light chain variable region amino acid sequence
DIQMTQSPSSLSASVGDRVTITCRASQGIRNYLAWYQQKPGKAPKLLIYAASTLQSGVPSRFSG
SGSGTDFTLTISSLQPEDVATYYCQRYNRAPYTFGQGTKVEIK (SEQ ID NO: 18)

Anti-TNF-α antibody heavy chain amino acid sequence
EVKLEESGGGLVQPGGSMKLSCVASGFIFSNHWMNWVRQSPEKGLEWVAEIRSKSINSATHY
AESVKGRFTISRDDSKSAVYLQMTDLRTEDTGVYYCSRNYYGSTYDYWGQGTTLTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNSTYRVVSVLTVLHQ
DWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYT
QKSLSLSPGK (SEQ ID NO: 19)

Anti-TNF-α antibody heavy chain variable region amino acid sequence
EVKLEESGGGLVQPGGSMKLSCVASGFIFSNHWMNWVRQSPEKGLEWVAEIRSKSINSATHY
AESVKGRFTISRDDSKSAVYLQMTDLRTEDTGVYYCSRNYYGSTYDYWGQGTTLTVSS
(SEQ ID NO: 20)

Anti-TNF-α antibody light chain amino acid sequence
DILLTQSPAILSVSPGERVSFSCRASQFVGSSIHWYQQRTNGSPRLLIKYASESMSGIPSRFSGS
GSGTDFTLSINTVESEDIADYYCQQSHSWPFTFGSGTNLEVKRTVAAPSVFIFPPSDEQLKSGT
ASVVCLLNNFYPREAKVQWKVDNALQSGNSQESVTEQDSKDSTYSLSSTLTLSKADYEKHKVY
ACEVTHQGLSSPVTKSFNRGEC (SEQ ID NO: 21)

Anti-TNF-α antibody light chain variable region amino acid sequence
DILLTQSPAILSVSPGERVSFSCRASQFVGSSIHWYQQRTNGSPRLLIKYASESMSGIPSRFSGS
GSGTDFTLSINTVESEDIADYYCQQSHSWPFTFGSGTNLEVK (SEQ ID NO: 22)

Anti-TNF-α antibody heavy chain amino acid sequence
EVQLVESGGGLVQPGGSLRLSCAASGYVFTDYGMNWVRQAPGKGLEWMGWINTYIGEPIYA
DSVKGRFTFSLDTSKSTAYLQMNSLRAEDTAVYYCARGYRSYAMDYWGQGTLVTVSSASTKG
PSVFPLAPSSKSTSGGTAALGCLVKDYFPEPVTVSWNSGALTSGVHTFPAVLQSSGLYSLSSV
VTVPSSSLGTQTYICNVNHKPSNTKVDKKVEPKSCDKTHTCAA (SEQ ID NO: 23)

Anti-TNF-α antibody heavy chain variable region amino acid sequence
EVQLVESGGGLVQPGGSLRLSCAASGYVFTDYGMNWVRQAPGKGLEWMGWINTYIGEPIYA
DSVKGRFTFSLDTSKSTAYLQMNSLRAEDTAVYYCARGYRSYAMDYWGQGTLVTVSS
(SEQ ID NO: 24)

Anti-TNF-α antibody light chain amino acid sequence
DIQMTQSPSSLSASVGDRVTITCKASQNVGTNVAWYQQKPGKAPKALIYSASFLYSGVPYRFS
GSGSGTDFTLTISSLQPEDFATYYCQQYNIYPLTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKV
YACEVTHQGLSSPVTKSFNRGEC (SEQ ID NO: 25)

Anti-TNF-α antibody light chain variable region amino acid sequence
DIQMTQSPSSLSASVGDRVTITCKASQNVGTNVAWYQQKPGKAPKALIYSASFLYSGVPYRFS
GSGSGTDFTLTISSLQPEDFATYYCQQYNIYPLTFGQGTKVEIK (SEQ ID NO: 26)

Anti-TNF-α antibody heavy chain amino acid sequence
QVQLVESGGGVVQPGRSLRLSCAASGFIFSSYAMHWVRQAPGNGLEWVAFMSYDGSNKKYA
DSVKGRFTISRDNSKNTLYLQMNSLRAEDTAVYYCARDRGIAAGGNYYYYGMDVWGQGTTVT
VSSASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGK (SEQ ID NO: 27)

-continued

SEQUENCE LISTINGS

Anti-TNF-α antibody heavy chain variable region amino acid sequence
QVQLVESGGGVVQPGRSLRLSCAASGFIFSSYAMHWVRQAPGNGLEWVAFMSYDGSNKKYA
DSVKGRFTISRDNSKNTLYLQMNSLRAEDTAVYYCARDRGIAAGGNYYYYGMDVWGQGTTVT
VSS (SEQ ID NO: 28)

Anti-TNF-α antibody light chain amino acid sequence
EIVLTQSPATLSLSPGERATLSCRASQSVYSYLAWYQQKPGQAPRLLIYDASNRATGIPARFSG
SGSGTDFTLTISSLEPEDFAVYYCQQRSNWPPFTFGPGTKVDIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 29)

Anti-TNF-α antibody light chain variable region amino acid sequence
EIVLTQSPATLSLSPGERATLSCRASQSVYSYLAWYQQKPGQAPRLLIYDASNRATGIPARFSG
SGSGTDFTLTISSLEPEDFAVYYCQQRSNWPPFTFGPGTKVDIK (SEQ ID NO: 30)

Anti-Activin antibody heavy chain amino acid sequence
QVQLVQSGAEVKKPGASVKVSCKASGYTFTSYGLSWVRQAPGQGLEWMGWIIPYNGNTNSA
QKLQGRVTMTTDTSTSTAYMELRSLRSDDTAVYFCARDRDYGVNYDAFDIWGQGTMVTVSSA
STKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNVYVDGVEVHNAKTKPREEQYNSTYRVVSVLTV
LHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPGK (SEQ ID NO: 31)

Anti-Activin A antibody heavy chain variable region amino acid sequence
QVQLVQSGAEVKKPGASVKVSCKASGYTFTSYGLSWVRQAPGQGLEWMGWIIPYNGNTNSA
QKLQGRVTMTTDTSTSTAYMELRSLRSDDTAVYFCARDRDYGVNYDAFDIWGQGTMVTVSS
(SEQ ID NO: 32)

Anti-Activin A antibody light chain amino acid sequence
SYEVTQAPSVSVSPGQTASITCSGDKLGDKYACWYQQKPGQSPVLVIYQDSKRPSGIPERFSG
SNSGNTATLTISGTQAMDEADYYCQAWDSSTAVFGGGTKLTVLRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 33)

Anti-Activin A antibody light chain variable region amino acid sequence
SYEVTQAPSVSVSPGQTASITCSGDKLGDKYACWYQQKPGQSPVLVIYQDSKRPSGIPERFSG
SNSGNTATLTISGTQAMDEADYYCQAWDSSTAVFGGGTKLTVL (SEQ ID NO: 34)

Anti-Activin A antibody heavy chain amino acid sequence
QVQLQESGPGLVKPSETLSLTCTVSGGSFSSHFWSWIRQPPGKGLEWIGYILYTGGTSFNPSL
KSRVSMSVGTSKNQFSLKLSSVTAADTAVYYCARARSGITFTGIIVPGSFDIWGQGTMVTVSSA
STKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH
YTQKSLSLSLGK (SEQ ID NO: 35)

Anti-Activin A antibody heavy chain variable region amino acid sequence
QVQLQESGPGLVKPSETLSLTCTVSGGSFSSHFWSWIRQPPGKGLEWIGYILYTGGTSFNPSL
KSRVSMSVGTSKNQFSLKLSSVTAADTAVYYCARARSGITFTGIIVPGSFDIWGQGTMVTVSS
(SEQ ID NO: 36)

Anti-Activin A antibody light chain amino acid sequence
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKRTVAAPSVFIFPPSDEQLKS
GTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO: 37)

Anti-Activin A antibody light chain variable region amino acid sequence
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIK (SEQ ID NO: 38)

A109 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSETQECLFFNANWEKDRTNQTGVEPCYGDKDKRRH
CFATWKNISGSIEIVKQGCWLDDINCYDRTDCVEKKDSPEVYFCCCEGNMCNEKFSYFPEMEV
TQPTSNPVTPKPP (SEQ ID NO: 39)

-continued

| SEQUENCE LISTINGS |
| --- |

A201 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSGAILGRSETQECLFYNANWELERTNQTGVEPCEGE
KDKRLHCYATWRNISGSIEIVKKGCWLDDFNCYDRTDCVETEENPQVYFCCCEGNMCNEKFS
YFPEMEVTQPTS (SEQ ID NO: 40)

A110 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSGNCWLRQAKNGRCQVLYKTELSKEECCSTGRLST
SWTEEDVNDNTLFKWMIFNGGAPNCIPCKETCENVDCGPGQSCVVDQTGSPRCVCAPDCSNI
TWKGPVCGLDGKTYRNECALLKARCKEQPELEVQYQGRCKKTCRDVFCPGSSTCVVDQTNN
AYCVTCNRICPEPASSEQYLCGNDGVTYSSACHLRKATCLLGRSIGLAYEGKCIKAKSCEDIQC
TGGKKCLWDFKVGRGRCSLCDELCPDSKSDEPVCASDNATYASECAMKEAACSSGVLLEVKH
SGSCNSISEDTEEEEEDEDQDYSFPISSILEW (SEQ ID NO: 41)

A301 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSGNCWLRQAKNGRCQVLYKTELSKEECCSTGRLST
SWTEEDVNDNTLFKWMIFNGGAPNCIPCKETCENVDCGPGKKCRMNKKNKPRCVCAPDCSNI
TWKGPVCGLDGKTYRNECALLKARCKEQPELEVQYQGRCKKTCRDVFCPGSSTCVVDQTNN
AYCVTCNRICPEPASSEQYLCGNDGVTYSSACHLRKATCLLGRSIGLAYEGKCIKAKSCEDIQC
TGGKKCLWDFKVGRGRCSLCDELCPDSKSDEPVCASDNATYASECAMKEAACSSGVLLEVKH
SGSCNSISEDTEEEEEDEDQDYSFPISSILEW (SEQ ID NO: 42)

A304 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSGNCWLRQAKNGRCQVLYKTELSKEECCSTGRLST
SWTEEDVNDNTLFKWMIFNGGAPNCIPCKETCENVDCGPGKKCRMNKKNKPRCVCAPDCSNI
TWKGPVCGLDGKTYRNECALLKARCKEQPELEVQYQGRCKKTCRDVFCPGSSTCVVDQTNN
AYCVTCNRICPEPASSEQYLCGNDGVTYSSACHLRKATCLLGRSIGLAYEGKCIKAKSCEDIQC
TGGKKCLWDFKVGRGRCSLCDELCPDSKSDEPVCASDNATYASECAMKEAACSSGVLLEVKH
SGSCN (SEQ ID NO: 43)

A410 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSETRECIYYNANWELERTNQSGLERCEGEQDKRLHC
YASWRNSSGTIELVKKGCWLDDFNCYDRQECVATEENPQVYFCCCEGNFCNERFTHLPEAG
GPEVTYEPPPTAPT (SEQ ID NO: 44)

A401 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP -continued

SEQUENCE LISTINGS

SDIAVEWESNGQPENNYKTTPPVLDSDGSFFLYSKLTVDKSRWQQGNVFSCSVMHEALHNHY
TQKSLSLSPGKGGGGSGGGGSGGGGSETRECIYYNANWELERTNQSGLERCEGDQDKRLH
CYASWRNSSGTIELVKKGCWLDDINCYDRQECVATKENPQVYFCCCEGNFCNERFTHLPEAG
GPEVTYEPPPTAPT (SEQ ID NO: 45)

A404 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSETRECIYYNANWELERTNQSGLERCYGDKDKRRH
CYASWRNSSGTIELVKKGCWLDDFNCYDRQECVATEENPQVYFCCCEGNFCNERFTHLPEA
GGPEVTYEPPPTAPT (SEQ ID NO: 46)

A407 Heavy chain amino acid sequence
EVQLVESGGGLVQPGRSLRLSCAASGFTFDDYAMHWVRQAPGKGLEWVSAITWNSGHIDYA
DSVEGRFTISRDNAKNSLYLQMNSLRAEDTAVYYCAKVSYLSTASSLDYWGQGTLVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHY
TQKSLSLSPGKGGGGSGGGGSGGGGSETRECIYYNANWELERTNQSGLERCEGEQDKRLHC
YASWRNSSGTIELVKKGCWDDDFNCYDRQECVATEENPQVYFCCCEGNFCNERFTHLPEAG
GPEVTYEPPPT (SEQ ID NO: 47)

A710 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSETQECLFFNANWEKDRTNQTGVEPCYGDKDKRRHCFATWKNISG
SIEIVKQGCWLDDINCYDRTDCVEKKDSPEVYFCCCEGNMCNEKFSYFPEMEVTQPTSNPVTP
KPP (SEQ ID NO: 48)

A711 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSETRECIYYNANWELERTNQSGLERCEGEQDKRLHCYASWRNSSG
TIELVKKGCWLDDFNCYDRQECVATEENPQVYFCCCEGNFCNERFTHLPEAGGPEV
TYEPPPTAPT (SEQ ID NO: 49)

A713 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSETRECIYYNANWELERTNQSGLERCEGDQDKRLHCYASWRNSSG
TIELVKKGCWLDDINCYDRQECVATKENPQVYFCCCEGNFCNERFTHLPEAGGPEVTYEPPPT
APT (SEQ ID NO: 50)

A714 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSETRECIYYNANWELERTNQSGLERCYGDKDKRRHCYASWRNSSG
TIELVKKGCWLDDFNCYDRQECVATEENPQVYFCCCEGNFCNERFTHLPEAGGPEVTYEPPP
TAPT (SEQ ID NO: 51)

-continued

SEQUENCE LISTINGS

A715 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSETRECIYYNANWELERTNQSGLERCEGEQDKRLHCYASWRNSSG
TIELVKKGCWDDDFNCYDRQECVATEENPQVYFCCCEGNFCNERFTHLPEAGGPEVTYEPPP
T (SEQ ID NO: 52)

A716 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSGAILGRSETQECLFYNANWELERTNQTGVEPCEGEKDKRLHCYAT
WRNISGSIEIVKKGCWLDDFNCYDRTDCVETEENPQVYFCCCEGNMCNEKFSYFPEMEVTQP
TS (SEQ ID NO: 53)

A712 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSGNCWLRQAKNGRCQVLYKTELSKEECCSTGRLSTSWTEEDVNDN
TLFKWMIFNGGAPNCIPCKETCENVDCGPGQSCVVDQTGSPRCVCAPDCSNITWKGPVCGLD
GKTYRNECALLKARCKEQPELEVQYQGRCKKTCRDVFCPGSSTCVVDQTNNAYCVTCNRICP
EPASSEQYLCGNDGVTYSSACHLRKATCLLGRSIGLAYEGKCIKAKSCEDIQCTGGKKCLWDF
KVGRGRCSLCDELCPDSKSDEPVCASDNATYASECAMKEAACSSGVLLEVKHSGSCNSISED
TEEEEEDEDQDYSFPISSILEW (SEQ ID NO: 54)

A717 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSGNCWLRQAKNGRCQVLYKTELSKEECCSTGRLSTSWTEEDVNDN
TLFKWMIFNGGAPNCIPCKETCENVDCGPGKKCRMNKKNKPRCVCAPDCSNITWKGPVCGLD
GKTYRNECALLKARCKEQPELEVQYQGRCKKTCRDVFCPGSSTCVVDQTNNAYCVTCNRICP
EPASSEQYLCGNDGVTYSSACHLRKATCLLGRSIGLAYEGKCIKAKSCEDIQCTGGKKCLWDF
KVGRGRCSLCDELCPDSKSDEPVCASDNATYASECAMKEAACSSGVLLEVKHSGSCNSISED
TEEEEEDEDQDYSFPISSILEW (SEQ ID NO: 55)

A718 amino acid sequence
IYPSGVIGLVPHLGDREKRDSVCPQGKYIHPQNNSICCTKCHKGTYLYNDCPGPGQDTDCREC
ESGSFTASENHLRHCLSCSKCRKEMGQVEISSCTVDRDTVCGCRKNQYRHYWSENLFQCFN
CSLCLNGTVHLSCQEKQNTVCTCHAGFFLRENECVSCSNCKKSLECTKLCLPQIENVKGTEDS
GTTGGGGSGGGGSGGGGSEPKSCDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPG
KGGGGSGGGGSGGGGSGNCWLRQAKNGRCQVLYKTELSKEECCSTGRLSTSWTEEDVNDN
TLFKWMIFNGGAPNCIPCKETCENVDCGPGKKCRMNKKNKPRCVCAPDCSNITWKGPVCGLD
GKTYRNECALLKARCKEQPELEVQYQGRCKKTCRDVFCPGSSTCVVDQTNNAYCVTCNRICP
EPASSEQYLCGNDGVTYSSACHLRKATCLLGRSIGLAYEGKCIKAKSCEDIQCTGGKKCLWDF
KVGRGRCSLCDELCPDSKSDEPVCASDNATYASECAMKEAACSSGVLLEVKHSGSCN
(SEQ ID NO: 56)

A719 Heavy chain amino acid sequence
QVQLVQSGAEVKKPGASVKVSCKASGYTFTSYGLSWVRQAPGQGLEWMGWIIPYNGNTNSA
QKLQGRVTMTTDTSTSTAYMELRSLRSDDTAVYFCARDRDYGVNYDAFDIWGQGTMVTVSSA
STKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPSCPAPEFLGGPSVFLFPPKP
KDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH -continued

SEQUENCE LISTINGS

YTQKSLSLSLGKGGGGSGGGGSGGGGSIYPSGVIGLVPHLGDREKRDSVCPQGKYIHPQNNS
ICCTKCHKGTYLYNDCPGPGQDTDCRECESGSFTASENHLRHCLSCSKCRKEMGQVEISSCT
VDRDTVCGCRKNQYRHYWSENLFQCFNCSLCLNGTVHLSCQEKQNTVCTCHAGFFLRENEC
VSCSNCKKSLECTKLCLPQIENVKGTEDSGTT (SEQ ID NO: 57)

A720 Heavy chain amino acid sequence
QVQLQESGPGLVKPSETLSLTCTVSGGSFSSHFWSWIRQPPGKGLEWIGYILYTGGTSFNPSL
KSRVSMSVGTSKNQFSLKLSSVTAADTAVYYCARARSGITFTGIIVPGSFDIWGQGTMVTVSSA
STKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH
YTQKSLSLSLGKGGGGSGGGGSGGGGSIYPSGVIGLVPHLGDREKRDSVCPQGKYIHPQNNS
ICCTKCHKGTYLYNDCPGPGQDTDCRECESGSFTASENHLRHCLSCSKCRKEMGQVEISSCT
VDRDTVCGCRKNQYRHYWSENLFQCFNCSLCLNGTVHLSCQEKQNTVCTCHAGFFLRENEC
VSCSNCKKSLECTKLCLPQIENVKGTEDSGTT (SEQ ID NO: 58)

A211 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSETQECLFFNANWEKDRTNQTGVEPCYGDKDKRRHCFATWKNISGSIEIVKQGCWLDDINC
YDRTDCVEKKDSPEVYFCCCEGNMCNEKFSYFPEMEVTQPTSNPVTPKPP (SEQ ID NO: 59)

A305 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSETRECIYYNANWELERTNQSGLERCEGEQDKRLHCYASWRNSSGTIELVKKGCWLDDFNC
YDRQECVATEENPQVYFCCCEGNFCNERFTHLPEAGGPEV TYEPPPTAPT (SEQ ID NO: 60)

A213 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSETRECIYYNANWELERTNQSGLERCEGDQDKRLHCYASWRNSSGTIELVKKGCWLDDINC
YDRQECVATKENPQVYFCCCEGNFCNERFTHLPEAGGPEVTYEPPPTAPT (SEQ ID NO: 61)

A214 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSETRECIYYNANWELERTNQSGLERCYGDKDKRRHCYASWRNSSGTIELVKKGCWLDDEN
CYDRQECVATEENPQVYFCCCEGNFCNERFTHLPEAGGPEVTYEPPPTAPT (SEQ ID NO: 62)

A215 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSETRECIYYNANWELERTNQSGLERCEGEQDKRLHCYASWRNSSGTIELVKKGCWDDDFN
CYDRQECVATEENPQVYFCCCEGNFCNERFTHLPEAGGPEVTYEPPPT (SEQ ID NO: 63)

-continued

SEQUENCE LISTINGS

A216 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSGAILGRSETQECLFYNANWELERTNQTGVEPCEGEKDKRLHCYATWRNISGSIEIVKKGCW
LDDFNCYDRTDCVETEENPQVYFCCCEGNMCNEKFSYFPEMEVTQPTS (SEQ ID NO: 64)

A105 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSGNCWLRQAKNGRCQVLYKTELSKEECCSTGRLSTSWTEEDVNDNTLFKWMIFNGGAPNCI
PCKETCENVDCGPGQSCVVDQTGSPRCVCAPDCSNITWKGPVCGLDGKTYRNECALLKARC
KEQPELEVQYQGRCKKTCRDVFCPGSSTCVVDQTNNAYCVTCNRICPEPASSEQYLCGNDGV
TYSSACHLRKATCLLGRSIGLAYEGKCIKAKSCEDIQCTGGKKCLWDFKVGRGRCSLCDELCP
DSKSDEPVCASDNATYASECAMKEAACSSGVLLEVKHSGSCNSISEDTEEEEEDEDQDYSFPI
SSILEW (SEQ ID NO: 65)

A217 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSGNCWLRQAKNGRCQVLYKTELSKEECCSTGRLSTSWTEEDVNDNTLFKWMIFNGGAPNCI
PCKETCENVDCGPGKKCRMNKKNKPRCVCAPDCSNITWKGPVCGLDGKTYRNECALLKARC
KEQPELEVQYQGRCKKTCRDVFCPGSSTCVVDQTNNAYCVTCNRICPEPASSEQYLCGNDGV
TYSSACHLRKATCLLGRSIGLAYEGKCIKAKSCEDIQCTGGKKCLWDFKVGRGRCSLCDELCP
DSKSDEPVCASDNATYASECAMKEAACSSGVLLEVKHSGSCNSISEDTEEEEEDEDQDYSFPI
SSILEW (SEQ ID NO: 66)

A218 amino acid sequence
LPAQVAFTPYAPEPGSTCRLREYYDQTAQMCCSKCSPGQHAKVFCTKTSDTVCDSCEDSTYT
QLWNWVPECLSCGSRCSSDQVETQACTREQNRICTCRPGWYCALSKQEGCRLCAPLRKCRP
GFGVARPGTETSDVVCKPCAPGTFSNTTSSTDICRPHQICNVVAIPGNASMDAVCTSTSPTRS
MAPGAVHLPQPVSTRSQHTQPTPEPSTAPSTSFLLPMGPSPPAEGSTGDGGGGSGGGGSGG
GGSEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGKGGGGSGGGGSGGG
GSGNCWLRQAKNGRCQVLYKTELSKEECCSTGRLSTSWTEEDVNDNTLFKWMIFNGGAPNCI
PCKETCENVDCGPGKKCRMNKKNKPRCVCAPDCSNITWKGPVCGLDGKTYRNECALLKARC
KEQPELEVQYQGRCKKTCRDVFCPGSSTCVVDQTNNAYCVTCNRICPEPASSEQYLCGNDGV
TYSSACHLRKATCLLGRSIGLAYEGKCIKAKSCEDIQCTGGKKCLWDFKVGRGRCSLCDELCP
DSKSDEPVCASDNATYASECAMKEAACSSGVLLEVKHSGSCN (SEQ ID NO: 67)

A219 Heavy chain amino acid sequence
QVQLVQSGAEVKKPGASVKVSCKASGYTFTSYGLSWVRQAPGQGLEWMGWIIPYNGNTNSA
QKLQGRVTMTTDTSTSTAYMELRSLRSDDTAVYFCARDRDYGVNYDAFDIWGQGTMVTVSSA
STKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPSCPAPEFLGGPSVFLFPPKP
KDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH
YTQKSLSLSLGKGGGGSGGGGSGGGGSLPAQVAFTPYAPEPGSTCRLREYYDQTAQMCCSK
CSPGQHAKVFCTKTSDTVCDSCEDSTYTQLWNWVPECLSCGSRCSSDQVETQACTREQNRI
CTCRPGWYCALSKQEGCRLCAPLRKCRPGFGVARPGTETSDVVCKPCAPGTFSNTTSSTDIC
RPHQICNVVAIPGNASMDAVCTSTSPTRSMAPGAVHLPQPVSTRSQHTQPTPEPSTAPSTSFL
LPMGPSPPAEGSTGD (SEQ ID NO: 68)

A220 Heavy chain amino acid sequence
QVQLQESGPGLVKPSETLSLTCTVSGGSFSSHFWSWIRQPPGKGLEWIGYILYTGGTSFNPSL
KSRVSMSVGTSKNQFSLKLSSVTAADTAVYYCARARSGITFTGIIVPGSFDIWGQGTMVTVSSA -continued

SEQUENCE LISTINGS

STKGPSVFPLAPCSRSTSESTAALGCLVKDYFPEPVTVSWNSGALTSGVHTFPAVLQSSGLYS
LSSVVTVPSSSLGTKTYTCNVDHKPSNTKVDKRVESKYGPPCPPCPAPEFLGGPSVFLFPPKP
KDTLMISRTPEVTCVVVDVSQEDPEVQFNWYVDGVEVHNAKTKPREEQFNSTYRVVSVLTVLH
QDWLNGKEYKCKVSNKGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEGNVFSCSVMHEALHNH
YTQKSLSLSLGKGGGGSGGGGSGGGGSLPAQVAFTPYAPEPGSTCRLREYYDQTAQMCCSK
CSPGQHAKVFCTKTSDTVCDSCEDSTYTQLWNWVPECLSCGSRCSSDQVETQACTREQNRI
CTCRPGWYCALSKQEGCRLCAPLRKCRPGFGVARPGTETSDVVCKPCAPGTFSNTTSSTDIC
RPHQICNVVAIPGNASMDAVCTSTSPTRSMAPGAVHLPQPVSTRSQHTQPTPEPSTAPSTSFL
LPMGPSPPAEGSTGD (SEQ ID NO: 69)

A785 Heavy chain amino acid sequence
QVQLVQSGAEVKKPGASVKVSCKASGYTFTSYGLSWVRQAPGQGLEWMGWIIPYNGNTNSA
QKLQGRVTMTTDTSTSTAYMELRSLRSDDTAVYFCARDRDYGVNYDAFDIWGQGTMVTVSSG
GGGSGGGGSGGGGSEVQLVESGGGLVQPGRSLRLSCAASGFTFDDYAMHWVRQAPGKGLE
WVSAITWNSGHIDYADSVEGRFTISRDNAKNSLYLQMNSLRAEDTAVYYCAKVSYLSTASSLDY
WGQGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 70)

A785 Light chain amino acid sequence
SYEVTQAPSVSVSPGQTASITCSGDKLGDKYACWYQQKPGQSPVLVIYQDSKRPSGIPERFSG
SNSGNTATLTISGTQAMDEADYYCQAWDSSTAVFGGGTKLTVLGGGGGGGGSGGGGSDIQ
MTQSPSSLSASVGDRVTITCRASQGIRNYLAWYQQKPGKAPKLLIYAASTLQSGVPSRFSGSG
SGTDFTLTISSLQPEDVATYYCQRYNRAPYTFGQGTKVEIKRTVAAPSVFIFPPSDEQLKSGTAS
VVCLLNNFYPREAKVQWKVDNALQSGNSQESVTEQDSKDSTYSLSSTLTLSKADYEKHKVYA
CEVTHQGLSSPVTKSFNRGEC (SEQ ID NO: 71)

A786 Heavy chain amino acid sequence
QVQLQESGPGLVKPSETLSLTCTVSGGSFSSHFWSWIRQPPGKGLEWIGYILYTGGTSFNPSL
KSRVSMSVGTSKNQFSLKLSSVTAADTAVYYCARARSGITFTGIIVPGSFDIWGQGTMVTVSSG
GGGSGGGGSGGGGSEVQLVESGGGLVQPGRSLRLSCAASGFTFDDYAMHWVRQAPGKGLE
WVSAITWNSGHIDYADSVEGRFTISRDNAKNSLYLQMNSLRAEDTAVYYCAKVSYLSTASSLDY
WGQGTLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKKVEPKSCDKTHTCPPCPAP
ELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSRDELT
KNQVSLTCLVKGFYPSDIAVEWESNGQPENNYKTTPPVLDSDGSFFLYSKLTVDKSRWQQGN
VFSCSVMHEALHNHYTQKSLSLSPGK (SEQ ID NO: 72)

A786 Light chain amino acid sequence
EIVLTQSPGTLSLSPGERATLSCRASQSVSSSYLAWYQQKPGQAPRLLIYGASSRATGIPDRFS
GSGSGTDFTLTISRLEPEDFAVYYCQQYGSSPWTFGQGTKVEIKGGGGSGGGGSGGGGSDIQ
MTQSPSSLSASVGDRVTITCRASQGIRNYLAWYQQKPGKAPKLLIYAASTLQSGVPSRFSGSG
SGTDFTLTISSLQPEDVATYYCQRYNRAPYTFGQGTKVEIKRTVAAPSVFIFPPSDEQLKSGTAS
VVCLLNNFYPREAKVQWKVDNALQSGNSQESVTEQDSKDSTYSLSSTLTLSKADYEKHKVYA
CEVTHQGLSSPVTKSFNRGEC (SEQ ID NO: 73)

Peptide linker sequence GGGSGGGSGGGS (SEQ ID NO: 74)

Peptide linker sequence GGGS (SEQ ID NO: 75)

Peptide linker sequence GSSGGSGGSGGSG (SEQ ID NO: 76)

Peptide linker sequence GSSGT (SEQ ID NO: 77)

Peptide linker sequence GGGGSGGGGSGGGS (SEQ ID NO: 78)

Peptide linker sequence AEAAAKEAAAKEAAAKA (SEQ ID NO: 79)

Peptide linker sequence GGGGSGGGGSGGGGSGGGGS (SEQ ID NO: 80)

Peptide linker sequence GGGSGGGS (SEQ ID NO: 81)

Peptide linker sequence GS (SEQ ID NO: 82)

Peptide linker sequence GGS (SEQ ID NO: 83)

Peptide linker sequence GGGGS (SEQ ID NO: 84)

Peptide linker sequence GGSG (SEQ ID NO: 85)

Peptide linker sequence SGGG (SEQ ID NO: 86)

-continued

| SEQUENCE LISTINGS |
|---|
| Peptide linker sequence GSGS (SEQ ID NO: 87) |
| Peptide linker sequence GSGSGS (SEQ ID NO: 88) |
| Peptide linker sequence GSGSGSGS (SEQ ID NO: 89) |
| Peptide linker sequence GSGSGSGSGS (SEQ ID NO: 90) |
| Peptide linker sequence GSGSGSGSGSGS (SEQ ID NO: 91) |
| Peptide linker sequence GGGGSGGGGS (SEQ ID NO: 92) |
| Peptide linker sequence GGGGGGGGSGGGGS (SEQ ID NO: 93) |

What is claimed is:

1. An isolated bifunctional antagonist molecule comprising a first molecule that is an antibody specifically binding to TNF-α and a second molecule that is a polypeptide specifically binding to an Activin or Activin-related ligand, wherein the bifunctional antagonist molecule simultaneously neutralizes TNF-α signaling and Activin signaling in a potent manner; and wherein the bifunctional molecule comprises the heavy chain amino acid sequence set forth in SEQ ID NO: 39 and the light chain amino acid sequence set forth in SEQ ID NO: 17.

2. A pharmaceutical composition comprising a therapeutically effective amount of the bifunctional antagonist molecule of claim 1 in admixture with a pharmaceutically acceptable carrier.

3. A method of treating pulmonary hypertension in a subject, comprising administering to said subject a therapeutically effective amount of the composition of claim 2.

4. An isolated nucleic acid molecule comprising a polynucleotide encoding a bifunctional antagonist molecule according to claim 1.

5. A recombinant vector comprising the nucleic acid molecule of claim 4.

6. A host cell comprising the recombinant vector of claim 5.

7. A method for producing a bifunctional antagonist molecule according to claim 1, comprising the steps of: a) transforming a host cell with a vector comprising a nucleic acid molecule encoding said bifunctional antagonist molecule, b) culturing the host cell under conditions suitable for the expression of the bifunctional antagonist molecule, and c) recovering the bifunctional antagonist molecule from the culture.

* * * * *